# United States Patent
Lain et al.

(10) Patent No.: US 11,795,157 B2
(45) Date of Patent: *Oct. 24, 2023

(54) TETRAHYDROINDAZOLES AND MEDICAL USES THEREOF

(71) Applicant: Genase Therapeutics B.V., Oss (NL)

(72) Inventors: Sonia Lain, Stockholm (SE); Catherine Drummond, Memphis, TN (US); Ingeborg Van Leeuwen, Solna. Stockholm (SE); Martin Haraldsson, Täby (SE); Lars Johansson, Bromma (SE); Lars Sandberg, Enskede (SE); Ulrika Yngve, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 17/144,673

(22) Filed: Jan. 8, 2021

(65) Prior Publication Data
US 2021/0230141 A1 Jul. 29, 2021

Related U.S. Application Data

(63) Continuation of application No. 15/772,650, filed as application No. PCT/GB2016/053383 on Nov. 1, 2016, now Pat. No. 10,889,564.

(30) Foreign Application Priority Data

Nov. 2, 2015 (SE) .................................. 1551410-2
Jun. 21, 2016 (GB) .................................. 1610823

(51) Int. Cl.
| | |
|---|---|
| C07D 401/12 | (2006.01) |
| C07D 403/12 | (2006.01) |
| C07D 405/12 | (2006.01) |
| C07D 409/12 | (2006.01) |
| A61K 31/416 | (2006.01) |
| A61K 31/4439 | (2006.01) |
| C07D 413/12 | (2006.01) |
| C07D 471/04 | (2006.01) |
| A61K 45/06 | (2006.01) |
| A61K 31/422 | (2006.01) |
| A61K 31/427 | (2006.01) |
| A61K 31/437 | (2006.01) |
| A61K 31/497 | (2006.01) |
| A61K 31/5377 | (2006.01) |
| C07D 413/14 | (2006.01) |
| A61K 31/4709 | (2006.01) |
| A61K 31/423 | (2006.01) |
| A61P 31/14 | (2006.01) |
| A61P 35/00 | (2006.01) |
| A61K 31/506 | (2006.01) |
| C07D 417/12 | (2006.01) |

(52) U.S. Cl.
CPC .......... *C07D 401/12* (2013.01); *A61K 31/416* (2013.01); *A61K 31/422* (2013.01); *A61K 31/423* (2013.01); *A61K 31/427* (2013.01); *A61K 31/437* (2013.01); *A61K 31/4439* (2013.01); *A61K 31/4709* (2013.01); *A61K 31/497* (2013.01); *A61K 31/506* (2013.01); *A61K 31/5377* (2013.01); *A61K 45/06* (2013.01); *A61P 31/14* (2018.01); *A61P 35/00* (2018.01); *C07D 403/12* (2013.01); *C07D 405/12* (2013.01); *C07D 409/12* (2013.01); *C07D 413/12* (2013.01); *C07D 413/14* (2013.01); *C07D 417/12* (2013.01); *C07D 471/04* (2013.01)

(58) Field of Classification Search
CPC . A61K 31/416; A61K 31/4439; A61K 31/506
See application file for complete search history.

(56) References Cited

U.S. PATENT DOCUMENTS 10,889,564 B2    1/2021 Lain et al.

FOREIGN PATENT DOCUMENTS

| | | |
|---|---|---|
| LV | 14476 | 2/2012 |
| WO | 2012/082689 A1 | 6/2012 |
| WO | 2013/078413 A1 | 5/2013 |
| WO | 2015/155680 A2 | 10/2015 |

OTHER PUBLICATIONS

Bartkova et al., Immunochemical analysis of the p53 oncoprotein in matched primary and metastatic human tumours. Eur J Cancer. 1993;29A(6):881-6.
Berkson et al., Pilot screening programme for small molecule activators of p53. Int J Cancer. Jul. 10, 2005;115(5):701-10.
Berstein, Metformin in obesity, cancer and aging: addressing controversies. Aging (Albany NY). May 2012;4(5):320-9.
Blaydes et al., DNA damage triggers DRB-resistant phosphorylation of human p53 at the CK2 site. Oncogene. Aug. 27, 1998;17(8):1045-52.

(Continued)

*Primary Examiner* — Kamal A Saeed
(74) *Attorney, Agent, or Firm* — McCarter & English LLP; Steven G. Davis

(57) ABSTRACT

There is herein provided a compound of formula I

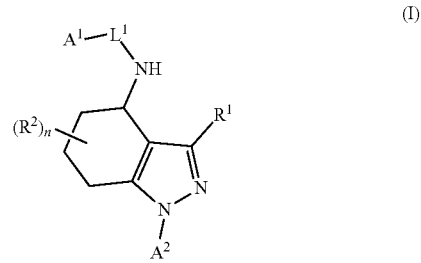

or a pharmaceutically acceptable salt thereof, for use in the treatment of cancer and/or the treatment or prevention of a viral infection, wherein $A^1$, $A^2$, $L^1$, $R^1$, $R^2$ and n have meanings as provided in the description.

12 Claims, 10 Drawing Sheets

(56) References Cited

OTHER PUBLICATIONS

Breedveld et al., Leflunomide: mode of action in the treatment of rheumatoid arthritis. Ann Rheum Dis. Nov. 2000;59(11):841-9.
Brown et al., Awakening guardian angels: drugging the p53 pathway. Nat Rev Cancer. Dec. 2009;9(12):862-73.
Brown et al., Stapled peptides with improved potency and specificity that activate p53. ACS Chem Biol. Mar. 15, 2013;8(3):506-12.
Bunz et al., Requirement for p53 and p21 to sustain G2 arrest after DNA damage. Science. Nov. 20, 1998;282(5393):1497-501.
Chabner et al., Purification and properties of cytidine deaminase from normal and leukemic granulocytes. J Clin Invest. Mar. 1974;53(3):922-31.
Charrier et al., Discovery of potent and selective inhibitors of ataxia telangiectasia mutated and Rad3 related (ATR) protein kinase as potential anticancer agents. J Med Chem. Apr. 14, 2011;54(7):2320-30.
Chen et al., Mapping of the p53 and mdm-2 interaction domains. Mol Cell Biol. Jul. 1993;13(7):4107-14.
Cheok et al., Cyclin-dependent kinase inhibitors sensitize tumor cells to nutlin-induced apoptosis: a potent drug combination. Mol Cancer Res. Nov. 2007;5(11):1133-45.
Choong et al., Specific activation of the p53 pathway by low dose actinomycin D: a new route to p53 based cyclotherapy. Cell Cycle. Sep. 1, 2009;8(17):2810-8.
Contente et al., A promoter that acquired p53 responsiveness during primate evolution. Cancer Res. Apr. 15, 2003;63(8):1756-8.
Ding et al., Structure-based design of spiro-oxindoles as potent, specific small-molecule inhibitors of the MDM2-p53 interaction. J Med Chem. Jun. 15, 2006;49(12):3432-5.
Drummond et al., Action of SN 28049, a new DNA binding topoisomerase II-directed antitumour drug: comparison with doxorubicin and etoposide. Invest New Drugs. Oct. 2011;29(5):1102-10.
Duursma et al., p53-Dependent regulation of Cdc6 protein stability controls cellular proliferation. Mol Cell Biol. Aug. 2005;25(16):6937-47.
Foote et al., Discovery of 4-{4-[(3R)-3-Methylmorpholin-4-yl]-6-[1-(methylsulfonyl)cyclopropyl]pyrimidin-2-yl}-1H-indole (AZ20): a potent and selective inhibitor of ATR protein kinase with monotherapy in vivo antitumor activity. J Med Chem. Mar. 14, 2013;56(5):2125-38.
Fredersdorf et al., Characterization of a Panel of Novel Anti-p21Waf1/Cip1 Monoclonal Antibodies and Immunochemical Analysis of p21Waf1/Cip1 Expression in Normal Human Tissue. American Journal of Pathology. Mar. 1996;148(3):825-35.
Ge et al., Differential gene expression, GATA1 target genes, and the chemotherapy sensitivity of Down syndrome megakaryocytic leukemia. Blood. Feb. 15, 2006;107(4):1570-81.
Ge et al., GATA1, cytidine deaminase, and the high cure rate of Down syndrome children with acute megakaryocytic leukemia. J Natl Cancer Inst. Feb. 2, 2005;97(3):226-31.
Ge et al., The role of cytidine deaminase and GATA1 mutations in the increased cytosine arabinoside sensitivity of Down syndrome myeloblasts and leukemia cell lines. Cancer Res. Jan. 15, 2004;64(2):728-35.
Girardelli et al., NLRP1 polymorphisms in patients with asbestos-associated mesothelioma. Infectious Agents and Cancer. 2012;7:25, 7 pages.
Gottifredi et al., p53 accumulates but is functionally impaired when DNA synthesis is blocked. Proc Natl Acad Sci U S A. Jan. 30, 2001;98(3):1036-41.
Guo et al., Identification, synthesis, and pharmacological evaluation of tetrahydroindazole based ligands as novel antituberculosis agents. J Med Chem. Jan. 28, 2010;53(2):649-59.
Hardcastle et al., Isoindolinone-based inhibitors of the MDM2-p53 protein-protein interaction. Bioorg Med Chem Lett. Mar. 1, 2005;15(5):1515-20.
Harris et al., High throughput screening identifies ATP-competitive inhibitors of the NLRP1 inflammasome. Bioorg Med Chem Lett. Jul. 15, 2015;25(14):2739-43.
Hastak et al., DNA synthesis from unbalanced nucleotide pools causes limited DNA damage that triggers ATR-CHK1-dependent p53 activation. Proc Natl Acad Sci U S A. Apr. 29, 2008;105(17):6314-9.
Hateboer et al., Cell cycle-regulated expression of mammalian CDC6 is dependent on E2F. Mol Cell Biol. Nov. 1998;18(11):6679-97.
Ji et al., Vemurafenib synergizes with nutlin-3 to deplete survivin and suppresses melanoma viability and tumor growth. Clin Cancer Res. Aug. 15, 2013;19(16):4383-91.
Khoo et al., Drugging the p53 pathway: understanding the route to clinical efficacy. Nat Rev Drug Discov. Mar. 2014;13(3):217-36.
Kolb et al., Inflammasomes in cancer: a double-edged sword. Protein Cell. Jan. 2014;5(1):12-20.
Lain et al., Discovery, in vivo activity, and mechanism of action of a small-molecule p53 activator. Cancer Cell. May 2008;13(5):454-63.
Lau et al., Divergent S phase checkpoint activation arising from prereplicative complex deficiency controls cell survival. Mol Biol Cell. Sep. 2009;20(17):3953-64.
Li et al., Abnormal MDMX degradation in tumor cells due to ARF deficiency. Oncogene. Aug. 9, 2012;31(32):3721-32.
Li et al., Activation of p53 by SIRT1 inhibition enhances elimination of CML leukemia stem cells in combination with matinib. Cancer Cell. Feb. 14, 2012;21(2):266-81.
Lin et al., Inhibitors of the aminoglycoside 6'-N-acetyltransferase type Ib [AAC(6')-Ib] identified by in silico molecular docking. Bioorg Med Chem Lett. Oct. 15, 2013;23(20):5694-8.
Linke et al., A reversible, p53-dependent G0/G1 cell cycle arrest induced by ribonucleotide depletion in the absence of detectable DNA damage. Genes Dev. Apr. 15, 1996;10(8):934-47.
Lu et al., Discordance between accumulated p53 protein level and its transcriptional activity in response to u.v. radiation. Oncogene. Jul. 18, 1996;13(2):413-8.
Lu et al., Restoring p53 function in human melanoma cells by inhibiting MDM2 and cyclin B1/CDK1-phosphorylated nuclear iASPP. Cancer Cell. May 13, 2013;23(5):618-33.
Lyons et al., Effects of Brequinar and Ciprofloxacin on De Novo Nucleotide Biosynthesis in Mouse L1210 Leukemia. Biochemistry International. Dec. 1990;22(6):939-949.
Marshall et al., SIRT1 promotes N-Myc oncogenesis through a positive feedback loop involving the effects of MKP3 and ERK on N-Myc protein stability. PLoS Genet. Jun. 2011;7(6):e1002135.
Martinez Molina et al., Monitoring drug target engagement in cells and tissues using the cellular thermal shift assay. Science. Jul. 5, 2013;341(6141):84-7.
Matsuoka et al., Multiple domains of the mouse p19ARF tumor suppressor are involved in p53-independent apoptosis. Biochem Biophys Res Commun. Feb. 21, 2003;301(4):1000-10.
Mccarthy et al., Synthesis and biological characterisation of sirtuin inhibitors based on the tenovins. Bioorg Med Chem. Mar. 1, 2012;20(5):1779-93.
Menssen et al., The c-MYC oncoprotein, the NAMPT enzyme, the SIRT1-inhibitor DBC1, and the SIRT1 deacetylase form a positive feedback loop. Proc Natl Acad Sci U S A. Jan. 24, 2012;109(4):E187-96.
Polyak et al., A model for p53-induced apoptosis. Nature. Sep. 18, 1997;389(6648):300-5.
Porté et al., Three-dimensional structure and enzymatic function of proapoptotic human p53-inducible quinone oxidoreductase PIG3. J Biol Chem. Jun. 19, 2009;284(25):17194-205.
Pérignon et al., Cytidine deaminase activity of human normal and malignant lymphoid cells. Clin Chim Acta. Apr. 15, 1985;147(2):67-74.
Pérignon et al., Synergistic toxicity of pyrazofurin and cytidine in cytidine deaminase deficient lymphoid cells (Raji). Int J Immunopharmacol. 1986;8(4):427-31.
Rao et al., Coamplification of Myc/Pvt1 and homozygous deletion of Nlrp1 locus are frequent genetics changes in mouse osteosarcoma. Genes Chromosomes Cancer. Dec. 2015;54(12):796-808.

(56) References Cited

OTHER PUBLICATIONS

Ray-Coquard et al., Effect of the MDM2 antagonist RG7112 on the P53 pathway in patients with MDM2-amplified, well-differentiated or dedifferentiated liposarcoma: an exploratory proof-of-mechanism study. Lancet Oncol. Nov. 2012;13(11):1133-40.

Rossner et al., What's in a picture? The temptation of image manipulation. J Cell Biol. Jul. 5, 2004;166(1):11-5.

Saville et al., Regulation of p53 by the ubiquitin-conjugating enzymes UbcH5B/C in vivo. J Biol Chem. Oct. 1, 2004;279(40):42169-81.

Shu et al., RNPC1, an RNA-binding protein and a target of the p53 family, is required for maintaining the stability of the basal and stress-induced p21 transcript. Genes Dev. Nov. 1, 2006;20(21):2961-72.

Smart et al., Effects on normal fibroblasts and neuroblastoma cells of the activation of the p53 response by the nuclear export inhibitor leptomycin B. Oncogene. Dec. 2, 1999;18(51):7378-86.

Staples et al., Characterization, chemical optimization and anti-tumour activity of a tubulin poison identified by a p53-based phenotypic screen. Cell Cycle. Nov. 1, 2008;7(21):3417-27.

Stott et al., The alternative product from the human CDKN2A locus, p14(ARF), participates in a regulatory feedback loop with p53 and MDM2. EMBO J. Sep. 1, 1998;17(17):5001-14.

Sullivan et al., ATM and MET kinases are synthetic lethal with nongenotoxic activation of p53. Nat Chem Biol. Jul. 2012;8(7):646-54.

Toledo et al., A cell-based screen identifies ATR inhibitors with synthetic lethal properties for cancer-associated mutations. Nat Struct Mol Biol. Jun. 2011;18(6):721-7.

Toledo et al., ATR signaling can drive cells into senescence in the absence of DNA breaks. Genes Dev. Feb. 1, 2008;22(3):297-302.

Turks et al., A Facile Synthesis of 4-Acylamino-Tetrahydroindazoles via the Ritter Reaction. Tetrahedron. 2012;68(31):6131-40.

Vassilev et al., In vivo activation of the p53 pathway by small-molecule antagonists of MDM2. Science. Feb. 6, 2004;303(5659):844-8.

Vojtesek et al., An immunochemical analysis of the human nuclear phosphoprotein p53. New monoclonal antibodies and epitope mapping using recombinant p53. J Immunol Methods. Jul. 6, 1992;151(1-2):237-44.

Weber et al., p53-independent functions of the p19(ARF) tumor suppressor. Genes Dev. Sep. 15, 2000;14(18):2358-65.

White et al., DHODH modulates transcriptional elongation in the neural crest and melanoma. Nature. Mar. 24, 2011;471(7339):518-22.

Williams et al., The NLRP1 inflammasome attenuates colitis and colitis-associated tumorigenesis. J Immunol. Apr. 1, 2015;194(7):3369-80.

Xirodimas et al., Different effects of p14ARF on the levels of ubiquitinated p53 and Mdm2 in vivo. Oncogene. Aug. 16, 2001;20(36):4972-83.

Xu et al., MDM2 expression is repressed by the RNA-binding protein RNPC1 via mRNA stability. Oncogene. Apr. 25, 2013;32(17):2169-78.

Yarbrough et al., Human Tumor Suppressor ARF Impedes S-Phase Progression Independent of p53, Cancer Res. Feb. 15, 2002;62:1171-7.

Yuan et al., Activation of stress response gene SIRT1 by BCR-ABL promotes leukemogenesis. Blood. Feb. 23, 2012;119(8):1904-14.

Zimmerman et al., Diminished origin-licensing capacity specifically sensitizes tumor cells to replication stress. Mol Cancer Res. Apr. 2013;11(4):370-80.

International Search Report and Written Opinion for Application No. PCT/GB2016/053383, dated Feb. 1, 2017.

TETRAHYDROINDAZOLES AND MEDICAL USES THEREOF

RELATED APPLICATION INFORMATION

This application is a continuation of U.S. patent application Ser. No. 15/772,650, filed May 1, 2018, which is a 371 of International Patent Application PCT/GB2016/053383, filed Nov. 1, 2016, which claims priority to GB Patent Application No.: 1610823.5, filed Jun. 21, 2016, and to Swedish Patent Application No.: 1551410-2, filed Nov. 2, 2015. The contents of these applications are herein incorporated by reference.

FIELD OF THE INVENTION

The present invention relates to novel treatments, and novel compounds and compositions that are of use in such treatments. In particular, the present invention relates to certain tetrahydroindazoles, which are useful in the treatment of cancers and/or the treatment or prevention of viral infections.

BACKGROUND OF THE INVENTION

The listing or discussion of an apparently prior-published document in this specification should not necessarily be taken as an acknowledgement that the document is part of the state of the art or is common general knowledge.

During the last decade a number of small molecules and peptides that activate p53 tumor suppressor functions in a DNA damage independent manner have been identified (see, for example, C. J. Brown et al., *Nature reviews: Cancer*, 9, 862 (2009)). Some of these compounds impair the interaction of p53 with mdm2 and/or mdmx (also called mdm4), two important negative regulators of p53 (see Hoe, C. S. et al., *Nat Rev Drug Discov.* 13, 217 (2014)).

There are several chemically distinct classes of mdm2/p53 binding antagonists and of these nutlin-3 is the most easily available and commonly used to protect p53 from degradation (see L. T. Vassilev et al., *Science.* 303, 844 (2004); I. R. Hardcastle et al., *Bioorganic & medicinal chemistry letters*, 15, 1515 (2005); K. Ding et al., *Journal of medicinal chemistry*, 49, 3432 (2006); and C. J. Brown et al., *ACS chemical biology*, 8, 506 (2013)). A derivative of nutlin-3, RG7112 (Roche), has recently completed Phase I clinical trials (see 1. Ray-Coquard et al., *The Lancet Oncology*, 13, 1133 (2012). Although mdm2/p53 binding antagonists have cytotoxic effects, they also have a reversible cytostatic effect that is likely to limit their efficacy. To some extent, this cytostatic effect could be due to a strong induction of p21 (waf1/cip1) by these compounds.

In the last few years, a series of reports have demonstrated that the efficacy of nutlin-3 at tumor cell killing is increased when administered in combination with other targeted small molecules such as the ATM kinase inhibitor KU-55933 and the BRAFV$^{600E}$ inhibitor vemurafenib (see K. D. Sullivan et al., *Nature Chemical Biology*, 8, 646 (2012); Z. Ji et al., *Clinical cancer research: an official journal of the American Association for Cancer Research*, 19, 4383 (2013); and M. Lu et al., *Cancer Cell*, 23, 618 (2013)).

Previous disclosures have utilized a series of phenotypic screens searching for novel p53 activators. These screens were carried out using a murine fibroblast cell line (T22 RGCΔFos-LacZ cells) and led to the identification of compounds that, as described for nutlin-3, activate p53 in all TP53 wild-type cells tested (see S. Lain et al., *Cancer Cell*, 13, 454 (2008); G. M. Marshall et al., *PLoS genetics*, 7, e1002135 (2011); H. Yuan et al., *Blood*, 119, 1904 (2012); A. Menssen et al., *Proc Natl Acad Sci USA*, 109, E187 (2012)).

Targeted therapeutics such as mdm2/p53 binding antagonists and BCR/ABL tyrosine kinase inhibitors can reduce cancer growth but rarely lead to the complete eradication of malignant cells. Thus, there exists a need to identify compounds capable of increasing pro-apoptotic functions of tumour suppressors that may increase the chance of achieving a cure in cancer patients.

Severe acute respiratory syndrome (SARS), Middle East respiratory syndrome (MERS), Western/Eastern equine encephalitis (WEE/EEE), and Ebola, as well as pandemic influenza (e.g. H1N1) are lethal and transmissible through travelers. The fast spread of these diseases constitute a major threat to public health worldwide and will require broad-spectrum antiviral agents to prevent pandemic scale outbreaks and allow time for the development of effective vaccines, when possible ("Broad-spectrum antiviral agents," Jun-Da Zhu, WenMeng, Xiao-JiaWang and Hwa-Chain, R. Wang, Frontiers in Microbiology, doi: 10.3389/fmicb.2015.00517).

International patent application WO 2013/078413 discloses heterocyclic compounds for use in modulating lipid storage and in treating neurodegenerative disorders.

Latvian patent application LV 14476 describes certain 4,5,6,7-tetrahydroindazoles as analgesics.

Lin, D. L. et al., *Bioorganic &Medicinal Chemistry Letters*, 23(20), 5694-5698 (2013) describes inhibitors of the aminoglycoside 6'-N-acetyltransferase type that are identified by in silico molecular docking.

Turks, M. et al., *Tetrahedron*, 68(31), 6131-6140 (2012) describes synthetic procedures for preparing 6,6-dimethyl-4,5,6,7-tetrahydroindazoles. However, no use is ascribed to such compounds.

Guo, S. et al., *Journal of Medicinal Chemistry*, 53(2), 649-659 (2010) describes the identification, synthesis and pharmacological evaluation of tetrahydroindazole-based ligands as possible anti-tuberculosis agents.

DESCRIPTION OF THE INVENTION

We have now surprisingly found compounds that are able to activate p53 in a cell background dependent manner. We have also found that such compounds may act as potent inhibitors of de novo pyrimidine synthesis through inhibition of dihydroorotate dehydrogenase (DHODH). Unexpectedly, we have found that this mechanism can induce p53 synthesis before DNA damage occurs and lead to cell death in a subset of cancer cells, whilst having significantly weaker effects on other cell types including normal cells.

Further, it is thought that such compounds are able to impair viral replication, which renders them of use in treating or preventing viral infections.

Compounds for Novel Medical Uses

In a first aspect of the invention, there is provided a compound of formula I

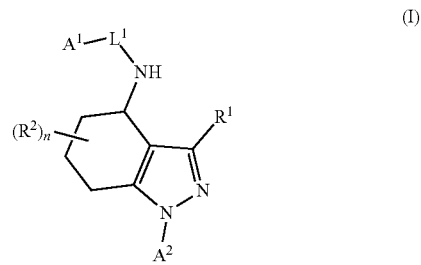

or a pharmaceutically acceptable salt thereof, for use in the treatment of cancer and/or the treatment or prevention of a viral infection, wherein:

$A^1$ represents aryl optionally substituted by one or more groups independently selected from $G^1$ or heteroaryl optionally substituted by one or more groups independently selected from $G^2$;

$A^2$ represents aryl optionally substituted by one or more groups independently selected from $G^3$ or heteroaryl optionally substituted by one or more groups independently selected from $G^4$;

$L^1$ represents —C(O)—, —C(O)N($R^3$)—, —C(O)O—, —S(O)$_j$— or —S(O)$_k$N($R^4$)—;

$R^1$ represents H or $C_{1-3}$ alkyl optionally substituted by one or more halo;

$R^2$ represents F;

$R^3$ and $R^4$ each independently represents H or $C_{1-3}$ alkyl optionally substituted by one or more halo;

each $G^1$ independently represents halo, $R^{a1}$, —CN, -$A^{a1}$-C($Q^{a1}$)$R^b$, $A^{b1}$-C($Q^{b1}$)N($R^{c1}$)$R^{d1}$-$A^{c1}$-C($Q^{c1}$)O$R^{e1}$, -$A^{d1}$-S(O)$_p$$R^{f1}$, -$A^{e1}$-S(O)$_q$N($R^{g1}$)$R^{h1}$, -$A^{f1}$-S(O)$_p$O$R^{i1}$, —$N_3$, —N($R^{j1}$)$R^{k1}$, —N(H)CN, —NO$_2$, —ONO$_2$, —O$R^{l1}$ or —S$R^{m1}$;

each $Q^{a1}$ to $Q^{c1}$ independently represents =O, =S, =N$R^{n1}$ or =N(O$R^{o1}$);

each $A^{a1}$ to $A^{f1}$ independently represents a single bond, —N($R^{p1}$)— or —O—;

each $G^2$ independently represents halo, $R^{a2}$, —CN, -$A^{a2}$-C($Q^{a2}$)$R^{b2}$-$A^{b2}$-C($Q^{b2}$)N($R^{c2}$)$R^{d2}$, -$A^{c2}$-C($Q^{c2}$)O$R^{e2}$, -$A^{d2}$-S(O)$_p$$R^{f2}$, -$A^{e2}$-S(O)$_q$N($R^{g2}$)$R^{h2}$, -$A^{f1}$-S(O)$_p$O$R^{i2}$, —$N_3$, —N($R^{j2}$)$R^{k2}$, —N(H)CN, —NO$_2$, —ONO$_2$, —O$R^{l2}$ or —S$R^{m2}$;

each $Q^{a2}$ to $Q^{c2}$ independently represents =O, =S, =N$R^{n2}$ or =N(O$R^{o2}$);

each $A^{a2}$ to $A^{f2}$ independently represents a single bond, —N($R^{p2}$)— or —O—;

each $G^3$ independently represents halo, $R^{a3}$, —CN, -$A^{a3}$-C($Q^{a3}$)$R^{b3}$, -$A^{b3}$-C($Q^{b3}$)N($R^{c3}$)$R^{d3}$-$A^{c3}$-C($Q^{c3}$)O$R^{e3}$, -$A^{d3}$-S(O)$_p$$R^{f3}$, -$A^{e3}$-S(O)$_q$N($R^{g3}$)$R^{h3}$, -$A^{f3}$-S(O)$_p$O$R^{i3}$, —$N_3$, —N($R^{j3}$)$R^{k3}$, —N(H)CN, —NO$_2$, —ONO$_2$, —O$R^{l3}$ or —S$R^{m3}$;

each $Q^{a3}$ to $Q^{c3}$ independently represents =O, =S, =N$R^{n3}$ or =N(O$R^{o3}$);

each $A^{a3}$ to $A^{f3}$ independently represents a single bond, —N($R^{p3}$)— or —O—;

each $G^4$ independently represents halo, $R^{a4}$, —CN, -$A^{a4}$-C($Q^{a4}$)$R^{b4}$, $A^{b4}$-C($Q^{b4}$)N($R^{c4}$)$R^{d4}$, -$A^{c4}$-C($Q^{c4}$)O$R^{e4}$, -$A^{d4}$-S(O)$_p$$R^{f4}$, -$A^{e4}$-S(O)$_q$N($R^{g4}$)$R^{h4}$, -$A^{f4}$-S(O)$_p$O$R^4$, —$N_3$, —N($R^4$)$R^{k4}$, —N(H)CN, —NO$_2$, —ONO$_2$, —O$R^{l4}$ or —S$R^{m4}$;

each $Q^{a4}$ to $Q^{c4}$ independently represents =O, =S, =N$R^{n4}$ or =N(O$R^{o4}$);

each $A^{a4}$ to $A^{f4}$ independently represents a single bond, —N($R^{p4}$)— or —O—;

each $R^{a1}$ and $R^{f1}$ independently represents $C_{1-6}$ alkyl optionally substituted by one or more groups independently selected from $G^{5a}$, heterocycloalkyl optionally substituted by one or more groups independently selected from $G^{5b}$, aryl optionally substituted by one or more groups independently selected from $G^{5c}$, or heteroaryl optionally substituted by one or more groups independently selected from $G^{5d}$;

each $R^{p1}$ independently represents H or $C_{1-6}$ alkyl optionally substituted by one or more halo;

each $R^{b1}$, $R^{c1}$, $R^{d1}$, $R^{e1}$, $R^{g1}$, $R^{h1}$, $R^{i1}$, $R^{j1}$, $R^{k1}$, $R^{l1}$, $R^{m1}$, $R^{n1}$ and $R^{o1}$ independently represents H, $C_{1-6}$ alkyl optionally substituted by one or more groups independently selected from $G^{5a}$, heterocycloalkyl optionally substituted by one or more groups independently selected from $G^{5b}$, aryl optionally substituted by one or more groups independently selected from $G^{5c}$, or heteroaryl optionally substituted by one or more groups independently selected from $G^{5d}$; or alternatively any of $R^{o1}$ and $R^{d1}$, $R^{g1}$ and $R^{h1}$ and/or $R^{j1}$ and $R^{k1}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl optionally substituted by one or more halo, and =O;

each $R^{a2}$ and $R^{f2}$ independently represents $C_{1-6}$ alkyl optionally substituted by one or more groups independently selected from $G^{6a}$, heterocycloalkyl optionally substituted by one or more groups independently selected from $G^{6b}$, aryl optionally substituted by one or more groups independently selected from $G^{6c}$, or heteroaryl optionally substituted by one or more groups independently selected from $G^{6d}$;

each $R^{p2}$ independently represents H or $C_{1-6}$ alkyl optionally substituted by one or more F;

each $R^{b2}$, $R^{c2}$, $R^{d2}$, $R^{e2}$, $R^{g2}$, $R^{h2}$, $R^{i2}$, $R^{j2}$, $R^{k2}$, $R^{l2}$, $R^{m2}$, $R^{n2}$ and $R^{o2}$ independently represents H, $C_{1-6}$alkyl optionally substituted by one or more groups independently selected from $G^{6a}$, heterocycloalkyl optionally substituted by one or more groups independently selected from $G^{6b}$, aryl optionally substituted by one or more groups independently selected from $G^{6c}$, or heteroaryl optionally substituted by one or more groups independently selected from $G^{6d}$; or alternatively any of $R^{c2}$ and $R^{d2}$, $R^{g2}$ and $R^{h2}$ and/or $R^{j2}$ and $R^{k2}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl optionally substituted by one or more halo, and =O;

each $R^{a3}$ and $R^{f3}$ independently represents $C_{1-6}$ alkyl optionally substituted by one or more groups independently selected from $G^{7a}$, heterocycloalkyl optionally substituted by one or more groups independently selected from $G^{7b}$, aryl optionally substituted by one or more groups independently selected from $G^{7c}$, or heteroaryl optionally substituted by one or more groups independently selected from $G^{7d}$;

each $R^{p3}$ independently represents H or $C_{1-6}$ alkyl optionally substituted by one or more F;

each $R^{b3}$, $R^{c3}$, $R^{d3}$, $R^{e3}$, $R^{f3}$, $R^{h3}$, $R^{i3}$, $R^{j3}$, $R^{k3}$, $R^{l3}$, $R^{m3}$, $R^{n3}$ and $R^{o3}$ independently represents H, $C_{1-6}$alkyl optionally substituted by one or more groups independently selected from $G^{7a}$, heterocycloalkyl optionally substituted by one or more groups independently selected from $G^{7b}$, aryl optionally substituted by one or more groups independently selected from $G^{7c}$, or heteroaryl optionally substituted by one or more groups independently selected from $G^{7d}$; or alternatively any of $R^{c3}$ and $R^{d3}$, $R^{g3}$ and $R^{h3}$ and/or $R^{j3}$ and $R^{k3}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl optionally substituted by one or more halo, and =O;

each $R^{a4}$ and $R^{f4}$ independently represents $C_{1-6}$ alkyl optionally substituted by one or more groups independently selected from $G^{8a}$, or heterocycloalkyl optionally substituted by one or more groups independently selected from $G^{8b}$, aryl optionally substituted by one or more groups independently selected from $G^{8c}$, or heteroaryl optionally substituted by one or more groups independently selected from $G^{8d}$;

each $R^{p4}$ independently represents H or $C_{1-6}$ alkyl optionally substituted by one or more F;

each $R^{b4}$, $R^{c4}$, $R^{d4}$, $R^{e4}$, $R^{g4}$, $R^{h4}$, $R^{i4}$, $R^{j4}$, $R^{k4}$, $R^{l4}$, $R^{m4}$, $R^{n4}$ and $R^{o4}$ independently represents H, $C_{1-6}$alkyl optionally substituted by one or more groups independently selected from $G^{8a}$ or heterocycloalkyl optionally substituted by one or more groups independently selected from $G^{8b}$; or alternatively any of $R^{c4}$ and $R^{d4}$, $R^{g4}$ and $R^{h4}$ and/or $R^{j4}$ and $R^{k4}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl optionally substituted by one or more halo, and =O;

each $G^{5a}$, $G^{5b}$, $G^{6a}$, $G^{6b}$, $G^{7a}$, $G^{7b}$, $G^{8a}$ and $G^{8b}$ independently represents halo, —CN, —N($R^{b5}$)$R^{c5}$, —OR$^{d5}$, —SR$^{e5}$ or =O;

each $G^{5c}$, $G^{5d}$, $G^{6c}$, $G^{6d}$, $G^{7c}$, $G^{7d}$, $G^{8c}$ and $G^{8d}$ independently represents halo, $R^{a5}$, —CN, —N($R^{b5}$)$R^{c5}$, —OR$^{d5}$, —SR$^{e5}$ or =O;

each $R^{a5}$ independently represents $C_{1-6}$ alkyl optionally substituted by one or more F;

each $R^{b5}$, $R^{c5}$, $R^{d5}$ and $R^{e5}$ independently represents H or $C_{1-6}$ alkyl optionally substituted by one or more F;

or $R^{b5}$ and $R^{c5}$ are linked together to form, along with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each j independently represents 0, 1 or 2;

each k, p and q independently represents 1 or 2; and n represents 0 to 7, which compounds (including pharmaceutically acceptable salts) may be referred to herein as compounds of the first aspect of the invention.

The skilled person will understand that references herein to compounds of particular aspects of the invention will include references to all embodiments and particular forms thereof, which embodiments and particular forms may be taken in combination to form further embodiments.

Unless indicated otherwise, all technical and scientific terms used herein have the same meaning as commonly understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxyethanesulphonate, 1- or 2-naphthalene-sulphonate or 1,5-naphthalenedisulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

For the avoidance of doubt, compounds of the first aspect of the invention may exist as solids, and thus the scope of the invention includes all amorphous, crystalline and part crystalline forms thereof, and may also exist as oils. Where compounds of the first aspect of the invention exist in crystalline and part crystalline forms, such forms may include solvates, which are included in the scope of the invention. Compounds of the first aspect of the invention may also exist in solution.

Compounds of the first aspect of the invention may contain double bonds and may thus exist as E (entgegen) and Z (zusammen) geometric isomers about each individual double bond. All such isomers and mixtures thereof are included within the scope of the invention.

Compounds of the first aspect of the invention may also exhibit tautomerism. All tautomeric forms and mixtures thereof are included within the scope of the invention.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution); for example, with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

In particular, compounds of the first aspect of the invention may exhibit stereoisomerism at the carbon marked with an asterisk (*) in the compound of formula I below, with compounds of the first aspect of the invention existing in the R- and S-configurations at that carbon (which configuration may be determined by those skilled in the art).

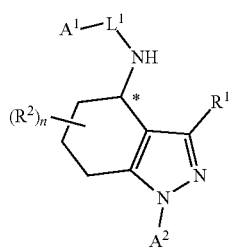

As used herein, references to halo and/or halogen groups will each independently refer to fluoro, chloro, bromo and iodo (for example, fluoro (F) and chloro (Cl)).

Unless otherwise specified, $C_{1-z}$ alkyl groups (where z is the upper limit of the range) defined herein may be straight-chain or, when there is a sufficient number (i.e. a minimum of two or three, as appropriate) of carbon atoms, be branched-chain, and/or cyclic (so forming a $C_{3-z}$-cycloalkyl group). When there is a sufficient number (i.e. a minimum of four) of carbon atoms, such groups may also be part cyclic. Part cyclic alkyl groups that may be mentioned include cyclopropylmethyl and cyclohexylethyl. When there is a sufficient number of carbon atoms, such groups may also be multicyclic (e.g. bicyclic or tricyclic) or spirocyclic. Such alkyl groups may also be saturated or, when there is a sufficient number (i.e. a minimum of two) of carbon atoms, be unsaturated (forming, for example, a $C_{2-z}$ alkenyl or a $C_{2-z}$ alkynyl group).

As used herein, the term aryl includes references to $C_{6-14}$ (e.g. $C_{6-10}$) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl and the like, such as phenyl). For the avoidance of doubt, the point of attachment of substituents on aryl groups may be via any carbon atom of the ring system.

As used herein, the term heteroaryl (or heteroaromatic) includes references to 5- to 14- (e.g. 5- to 10-) membered heteroaromatic groups containing one or more heteroatoms selected from oxygen, nitrogen and/or sulphur. Such heteroaryl groups may comprise one, two, or three rings, of which at least one is aromatic (e.g. a heteroaryl group may comprise two rings, one of which is aromatic). Substituents on heteroaryl/heteroaromatic groups may, where appropriate, be located on any atom in the ring system including a heteroatom. The point of attachment of heteroaryl/heteroaromatic groups may be via any atom in the ring system including (where appropriate) a heteroatom. In particular, bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocycloalkyl ring. Examples of heteroaryl/heteroaromatic groups that may be mentioned include pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, pyrazolopyrimidinyl, indazolyl, pyrimidinyl, quinolinyl, isoquinolinyl, quinazolinyl, benzofuranyl, benzothiophenyl, benzoimidazolyl, benzoxazolyl, benzothiazolyl, benzotriazolyl and purinyl. The oxides of heteroaryl/heteroaromatic groups are also embraced within the scope of the invention (e.g. the N-oxide). As stated above, heteroaryl includes polycyclic (e.g. bicyclic) groups in which one ring is aromatic (and the other(s) may or may not be aromatic). Hence, other heteroaryl groups that may be mentioned include e.g. benzo[1,3]dioxolyl, benzo[1,4]dioxinyl, dihydrobenzo[d]isothiazole, 3,4-dihydrobenz[1,4]oxazinyl, dihydrobenzothiophenyl, indolinyl, 5H,6H,7H-pyrrolo[1,2-b]pyrimidinyl, tetrahydro-1,2-benzisoxazolyl, 1,2,3,4-tetrahydroquinolinyl, thiochromanyl and the like.

As used herein, the term heterocycloalkyl may refer to non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten and, most preferably, between three and eight, e.g. a 5- or 6-membered heterocycloalkyl group). Further, such heterocycloalkyl groups may be saturated or unsaturated containing one or more double and/or triple bonds, forming for example a $C_{2-z}$ (e.g. $C_{4-z}$) heterocycloalkenyl (where z is the upper limit of the range) or a $C_{7-z}$ heterocycloalkynyl group. $C_{2-z}$ heterocycloalkyl groups that may be mentioned include 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, 2,3-dihydroisothiazolyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, isothiazolidinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulpholanyl, 3-sulpholenyl, tetrahydropyranyl, tetrahydrofuryl, tetrahydropyridyl (such as 1,2,3,4-tetrahydropyridyl and 1,2,3,6-tetrahydropyridyl), thietanyl, thiiranyl, thiolanyl, tetrahydrothiopyranyl, thiomorpholinyl, trithianyl (including 1,3,5-trithianyl), tropanyl and the like. Substituents on heterocycloalkyl groups may, where appropriate, be located on any atom in the ring system including a heteroatom. Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a further heteroatom (such as a nitrogen atom), or an atom on any fused carbocyclic ring that may be present as part of the ring system. Heterocycloalkyl groups may also be in the N- or S-oxidised form.

At each occurrence when mentioned herein, particular heterocycloalkyl groups that may be mentioned include 3- to 8-membered heterocycloalkyl groups (e.g. a 4- to 6-membered heterocycloalkyl group).

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulphur (e.g. oxygen, nitrogen and sulphur).

For the avoidance of doubt, references to polycyclic (e.g. bicyclic) groups (e.g. when employed in the context of heterocycloalkyl groups) will refer to ring systems wherein more than two scissions would be required to convert such rings into a straight chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of heterocycloalkyl groups) may refer to groups in which the second ring of a two-ring system is formed between two adjacent atoms of the first ring, and may also refer to groups in which two non-adjacent atoms are linked by either an alkylene or heteroalkylene chain (as appropriate), which later groups may be referred to as bridged.

For the avoidance of doubt, when an aryl or an heteroaryl group is substituted with a group via a double bond, such as =O, it is understood that the aryl or heteroaryl group is partly aromatic, i.e. the aryl or heteroaryl group consists of at least two rings where at least one ring is not aromatic.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more $R^4$ groups are present, those $R^4$ groups may be the same or different. Similarly, where two or more $R^4$ groups are present and each represent $R^{a2}$, the $R^{2a}$ groups in question may be the same or different. Likewise, when more than one $R^{a1}$ is present and each independently represents $C_{1-6}$ alkyl substituted by one or more $G^{1a}$ group, the identities of each $G^{1a}$ are in no way interdependent.

For the avoidance of doubt, when a term such as "$A^{a1}$ to $A^{f1}$" is employed herein, this will be understood by the skilled person to mean $A^{a1}$, $A^{b1}$, $A^{c1}$, $A^{d1}$, $A^{e1}$ and $A^{f1}$ inclusively. Unless otherwise stated, the same reasoning will apply to other such terms used herein.

The skilled person will appreciate that compounds of the invention that are the subject of this invention include those that are stable. That is, compounds of the invention include those that are sufficiently robust to survive isolation, e.g. from a reaction mixture, to a useful degree of purity.

All embodiments of the invention and particular features mentioned herein may be taken in isolation or in combination with any other embodiments and/or particular features mentioned herein (hence describing more particular embodiments and particular features as disclosed herein) without departing from the disclosure of the invention.

In particular embodiments of the first aspect of the invention, $A^1$ represents phenyl optionally substituted by one or more (such as one, two or three, e.g. one or two) groups independently selected from $G^1$ or heteroaryl optionally substituted by one or more (such as one, two or three, e.g. one or two) groups independently selected from $G^2$.

In more particular embodiments, $A^1$ represents heteroaryl optionally substituted by one or more (such as one, two or three, e.g. one or two) groups independently selected from $G^2$.

In yet more particular embodiments, $A^1$ represents a mono- or bi-cyclic heteroaryl optionally substituted by one or more (e.g. one or two groups) groups (i.e. $G^2$ groups) independently selected from halo, $R^{a2}$, —C(O)O$R^{e2}$, —O$R^{l2}$ and —S$R^{m2}$.

In yet more particular embodiments, $A^1$ represents a mono- or bi-cyclic heteroaryl optionally substituted by one or more (e.g. one or two) groups (i.e. $G^2$ groups) independently selected from halo (e.g. F), $C_{1-3}$ alkyl optionally substituted by one or more fluoro (such as —CF$_3$), —C(O)OH, —C(O)O$C_{1-3}$ alkyl, —OH, —O$C_{1-3}$ alkyl, —SH and —S$C_{1-3}$ alkyl (such as F, $C_{1-2}$ alkyl, —OH and —SCH$_3$).

In yet more particular embodiments, $A^1$ represents a mono- or bi-cyclic heteroaryl optionally substituted by one or more (e.g. one or two) groups (i.e. $G^2$ groups) independently selected from halo (e.g. F), $C_{1-3}$ alkyl, —CF$_3$, —C(O)OH, —C(O)O$C_{1-3}$ alkyl, —OH, —O$C_{1-3}$ alkyl, —SH and —S$C_{1-3}$ alkyl (such as F, $C_{1-2}$ alkyl, —OH and —SCH$_3$).

In yet more particular embodiments, $A^1$ represents a mono- or bi-cyclic heteroaryl optionally substituted by one or more (e.g. one or two) groups (i.e. $G^2$ groups) independently selected from halo (e.g. F), $C_{1-3}$ alkyl, —C(O)OH, —C(O)O$C_{1-3}$ alkyl, —OH, —O$C_{1-3}$ alkyl, —SH and —S$C_{1-3}$ alkyl (such as F, $C_{1-2}$ alkyl, —OH and —SCH$_3$).

For example, $A^1$ may represent a bi-cyclic heteroaryl (for example, a 9-membered bi-cyclic heteroaryl, such as tetrahydro-1,2-benzisoxazolyl, e.g. tetrahydro-1,2-benzisoxazol-3-yl) optionally substituted by one or two groups (i.e. $G^2$ groups) independently selected from halo, $R^{a2}$, —C(O)O$R^{e2}$, —O$R^{l2}$ and —S$R^{m2}$ (such as one or two groups independently selected from halo (e.g. F), $C_{1-3}$ alkyl, —C(O)OH, —C(O)O$C_{1-3}$ alkyl, —OH, —O$C_{1-3}$ alkyl, —SH and —S$C_{1-3}$ alkyl, e.g. one or two groups (i.e. $G^2$ groups) independently selected from F, $C_{1-2}$ alkyl, —OH and —SCH$_3$). For the avoidance of doubt, such bi-cyclic heteroaryl (for example, a 9-membered bi-cyclic heteroaryl, such as tetrahydro-1,2-benzisoxazolyl, e.g. tetrahydro-1,2-benzisoxazol-3-yl) groups may be unsubstituted.

Further, $A^1$ may represent a mono-cyclic heteroaryl (for example, a 6-membered mono-cyclic heteroaryl, such pyridinyl, e.g. pyridine-2-yl) optionally substituted by one or two groups (i.e. $G^2$ groups) independently selected from halo, $R^{a2}$, —C(O)O$R^{e2}$, —O$R^{l2}$ and —S$R^{m2}$ (such as one or two groups independently selected from halo (e.g. F), $C_{1-3}$ alkyl, —C(O)OH, —C(O)O$C_{1-3}$ alkyl, —OH, —O$C_{1-3}$ alkyl, —SH and —S$C_{1-3}$ alkyl, e.g. one or two groups selected from F, $C_{1-3}$ alkyl, —C(O)OH and —C(O)O$C_{1-3}$ alkyl, for example one —C(O)O$C_{1-3}$ alkyl or —C(O)OH group). For the avoidance of doubt, such mono-cyclic heteroaryl (for example, a 6-membered mono-cyclic heteroaryl, such pyridinyl, e.g. pyridine-2-yl) groups may be unsubstituted.

In particular embodiments, the mono- or bi-cyclic heteroaryl representing $A^1$ may be a 5- or 6-membered monocyclic or a 9- or 10-membered bicyclic heteroaryl (e.g. a 5- or 6-membered monocyclic or a 9-membered bicyclic heteroaryl). In particular, the mono- or bi-cyclic heteroaryl may be selected from pyridinyl (e.g. pyridine-2-yl and pyridine-3-yl), pyrazinyl (e.g. pyrazin-2-yl), benzofuranyl (e.g. benzofuran-3-yl), thiozolyl (e.g. thiozol-4-yl), thiophenyl (e.g. thiophen-2-yl), isoxazolyl (e.g. isoxazol-3-yl), 4,5,6,7-tetrahydrobenzo[c]isoxazolyl (e.g. 4,5,6,7-tetrahydrobenzo[c]isoxazo-3-yl), 1,3-benzoxazolyl (e.g. 1,3-benzoxazol-2-yl) and 1,2-benzisoxazolyl (e.g. 1,2-benzisoxazol-3-yl).

In alternative embodiments, the mono- or bi-cyclic heteroaryl representing $A^1$ may be a 5- or 6-membered monocyclic or a 9- or 10- (e.g. 9-) membered bicyclic heteroaryl.

In particular, the mono- or bi-cyclic heteroaryl may be selected from tetrahydro-2,1-benzisoxazolyl (e.g. tetrahydro-2,1-benzisoxazol-3-yl), benzoxazoyl (e.g. 1,3-benzisoxazol-3-yl or 1,2-benzisoxazol-3-yl), pyrazinyl, indazolyl, quinolinyl, 5H,6H,7H,8H-imidazo[1,5-a]pyridine-3-yl, imidazo[1,5-a]pyridin-3-yl, pyridinyl (e.g. pyridine-2-yl), thiozolyl (e.g. thiozol-4-yl), isoxazolyl (e.g. isoxazol-3-yl) and tetrahydro-1,2-benzisoxazolyl (e.g. tetrahydro-1,2-benzisoxazol-3-yl). More particularly, the mono- or bi-cyclic heteroaryl may be selected from pyridinyl (e.g. pyridine-2-yl), thiozolyl (e.g. thiozol-4-yl), isoxazolyl (e.g. isoxazol-3-yl) and tetrahydro-1,2-benzisoxazolyl (e.g. tetrahydro-1,2-benzisoxazol-3-yl).

In particular embodiments of the first aspect of the invention, $A^2$ represents phenyl optionally substituted by one or more (preferably one, two or three, e.g. one or two) groups independently selected from $G^3$ or a 5- or 6-membered heteroaryl optionally substituted by one or more (preferably one, two or three, e.g. one or two) groups independently selected from $G^4$.

In more particular embodiments of the first aspect of the invention, $A^2$ represents aryl optionally substituted by one or more (preferably one, two or three, e.g. one or two) groups independently selected from $G^3$.

In yet more particular embodiments of the first aspect of the invention, $A^2$ represents phenyl optionally substituted by one or more (preferably one, two or three, e.g. one or two) groups independently selected from $G^3$.

In more particular embodiments, $A^2$ represents phenyl optionally substituted by one or more (e.g. one or two) groups (i.e. $G^3$ groups) independently selected from halo, $R^{a3}$ and —$OR^{i3}$.

In further embodiments, $G^3$ represents a group selected from halo, -$A^{c3}$-C($Q^{c3}$)$OR^{e3}$ (e.g. —C(O)$OR^{e3}$, such as wherein $R^{e3}$ represents $C_{1-3}$ alkyl), $R^{a3}$ and —$OR^{i3}$.

In yet further embodiments, $G^3$ represents a group selected from halo, -$A^{a3}$-C($Q^{a3}$)$R^{b3}$ (e.g. —C(O)heteroaryl, for example —C(O)-morpholinyl, such as —C(O)-morpholin-4-yl) or -$A^{c3}$-C($Q^{c3}$)$OR^{e3}$ (e.g. —C(O)$OR^{e3}$, such as wherein $R^{e3}$ represents $C_{1-3}$ alkyl), $R^{a3}$ and —$OR^{i3}$.

In alternative embodiments, $G^3$ represents a group selected from halo, —$R^{a3}$ and —$OR^{i3}$.

More particularly, $A^2$ may represent phenyl optionally substituted by one or more (e.g. one or two) groups (i.e. $G^3$ groups) independently selected from halo (e.g. F), —C(O)$OC_{1-3}$ alkyl (such as —C(O)$OCH_2CH_3$), and $C_{1-4}$ alkyl (such as —$CH_3$ and —C($CH_3$)$_3$). For example, $A^2$ may represent phenyl optionally substituted by one or two groups (i.e. $G^3$ groups) independently selected from F, —$CH_3$, —C(O)$OCH_2CH_3$ and —C($CH_3$)$_3$, such as phenyl substituted by one or two F.

Alternatively, $A^2$ may represent phenyl optionally substituted by one or more (e.g. one or two) groups (i.e. $G^3$ groups) independently selected from halo (e.g. F), —C(O)-morpholinyl (such as —C(O)-morpholin-4-yl), —C(O)$OC_{1-3}$ alkyl (such as —C(O)$OCH_2CH_3$), and $C_{1-4}$ alkyl (such as —$CH_3$ and —C($CH_3$)$_3$).

In more particular embodiments, $A^2$ is unsubstituted in at least the 2-position (i.e. relative to the point of attachment to the essential tetrahydroindazole, as depicted in formula I, wherein the skilled person will understand that the point of attachment is referred to as the 1-position).

Thus, in certain embodiments, the group representing $A^2$ may be depicted as

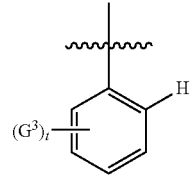

wherein $G^3$ is as defined herein (i.e. as defined in any embodiment of the first aspect of the invention, or any combination thereof, such as where $G^3$ represents a group independently selected from halo, $R^a$ and —$OR^{i3}$, e.g. a group selected from F, —$CH_3$ and —C($CH_3$)$_3$ (for example, a F group), t represents 0 to 5 (e.g. 0 to 2) and the bond dissected by the wavy line indicates the point of attachment to the essential tetrahydroindazole group.

More particularly, $A^2$ may be phenyl substituted with one or two substituents which are present at the 3-, 4-, 5- and/or 6-position(s). For example, $A^2$ may be phenyl substituted only in the 6-position (and therefore unsubstituted in the 2-, 3-, 4- and 5-positions), only in the 4- and 6-positions, or only in the 3- and 4-positions.

In particular embodiments of the first aspect of the invention, $L^1$ represents —C(O)N($R^3$)—, —C(O)O—, —S(O)$_2$N($R^4$)—, —C(O)— or —S(O)$_2$— (such as —C(O)— or —S(O)$_2$—).

In more particular embodiments, $L^1$ represents —C(O)—.

In particular embodiments of the first aspect of the invention, $R^1$ represents H or $C_{1-3}$ alkyl (e.g. $C_1$ alkyl) optionally substituted by one or more F (e.g. H or —$CH_3$).

More particularly, $R^1$ may represent H.

In particular embodiments of the first aspect of the invention, $R^2$ is not present at the point of attachment of the —NH-$L^1$-$A^1$ group to the tetrahydroindazole (i.e. H is present at that position), in which case n represents 0 to 6.

In more particular embodiments of the first aspect of the invention, n represents 0 to 2, in particular wherein, when n represents 2, each $R^2$ is present on the same carbon atom.

In particular embodiments of the first aspect of the invention, n represents 0.

In particular embodiments of the first aspect of the invention, $R^3$ and $R^4$ each independently represents H or $C_{1-3}$ alkyl optionally substituted by one or more F.

In more particular embodiments, $R^3$ represents H. In more particular embodiments, $R^4$ represents H. Thus, in yet more particular embodiments, $R^3$ and $R^4$ each represent H.

In particular embodiments of the first aspect of the invention:
each $G^1$ independently represents —CN, -$A^{a1}$-C($Q^{a1}$)$R^{b1}$, $A^{b1}$-C($Q^{b1}$)N($R^{c1}$)$R^{d1}$-$A^{c1}$-C($Q^{c1}$)$OR^{e1}$, -$A^{d1}$-S(O)$_p$$R^{f1}$, -$A^{e1}$-S(O)$_q$N($R^{g1}$)$R^{h1}$, -$A^{f1}$-S(O)$_p$$OR^{i1}$, —$N_3$, —N($R^{j1}$)$R^{k1}$, —N(H)CN, —$NO_2$, —$ONO_2$, halo, $R^{a1}$, —$OR^{i1}$ or —$SR^{m1}$ (such as halo, $R^{a1}$, —C(O)$OR^{e1}$, —$OR^{i1}$ and —$SR^{m1}$);
each $Q^{a1}$ to $Q^{c1}$ independently represents =O, =S, =N$R^{n1}$ or =N($OR^{o1}$) (such as =O); and/or (e.g. and)
each $A^{a1}$ to $A^{f1}$ independently represents a single bond, —N($R^{p1}$)— or —O—.

In particular embodiments of the first aspect of the invention:
each $G^2$ independently represents —CN, -$A^{a2}$-C($Q^{a2}$)$R^{b2}$-$A^{b2}$-C($Q^{b2}$)N($R^{c2}$)$R^{d2}$, -$A^{c2}$-C($Q^{c2}$)$OR^{e2}$, -$A^{d2}$-S(O)$_p$$R^{f2}$, $A^{e2}$-S(O)$_q$N($R^{g2}$)$R^{h2}$, -$A^{f1}$-S(O)$_p$$OR^{i2}$, —$N_3$, —N($R^{j2}$)$R^{k2}$, —N(H)CN, —NO$_2$, —ONO$_2$, halo, R$^{a2}$, —OR$^{l2}$ or —SR$^{m2}$ (such as halo, R$^{a2}$, —C(O)OR$^{e2}$, —OR$^{l2}$ or —SR$^{m2}$);

each Q$^{a2}$ to Q$^{c2}$ independently represents =O, =S, =NR$^{n2}$ or =N(OR$^{o2}$) (such as =O); and/or (e.g. and)

each A$^{a2}$ to A$^{f2}$ independently represents a single bond, —N(R$^{p2}$)— or —O—.

In particular embodiments, each G$^2$ independently represents halo, R$^{a2}$, —C(O)OR$^{e2}$, —OR$^{l2}$ and —SR$^{m2}$.

In more particular embodiments, each G$^2$ independently represents halo (e.g. F), C$_{1-3}$ alkyl, —C(O)OH, —C(O)OC$_{1-3}$ alkyl, —OH, —OC$_{1-3}$ alkyl, —SH and —SC$_{1-3}$ alkyl (such as F, C$_{1-2}$ alkyl, —OH and —SCH$_3$).

In particular embodiments of the first aspect of the invention:

each G$^3$ independently represents —CN, -A$^{a3}$-C(Q$^{a3}$)R$^{b3}$, A$^{b3}$-C(Q$^{b3}$)N(R$^{c3}$)R$^{d3}$-A$^3$-C(Q$^{c3}$)OR$^{e3}$, -A$^{d3}$-S(O)$_p$R$^{f3}$, -A$^{e3}$-S(O)$_q$N(R$^{g3}$)R$^{h3}$, -A$^{f3}$-S(O)$_p$OR$^{i3}$, —N$_3$, —N(R$^{j3}$)R$^{k3}$, —N(H)CN, —NO$_2$, —ONO$_2$, halo, R$^{a3}$, —OR$^{l3}$ or —SR$^{m3}$ (such as halo, R$^{a3}$, —OR$^{l3}$ or —SR$^{m3}$);

each Q$^{a3}$ to Q$^{c3}$ independently represents =O, =S, =NR$^{n3}$ or =N(OR$^{o3}$) (such as =O); and/or each A$^{a3}$ to A$^{f3}$ independently represents a single bond, —N(R$^{p3}$)— or —O—.

In more particular embodiments, each G$^3$ independently represents halo, R$^{a3}$ or —OR$^{l3}$.

In yet more particular embodiments, each G$^3$ independently represents halo (e.g. F) or C$_{1-4}$ alkyl, such as F, —CH$_3$ or —C(CH$_3$)$_3$.

In yet more particular embodiments, each G$^3$ independently represents F or —CH$_3$, such as F.

In particular embodiments of the first aspect of the invention:

each G$^4$ independently represents —CN, -A$^{a4}$-C(Q$^{a4}$)R$^{b4}$, A$^{b4}$-C(Q$^{b4}$)N(R$^{c4}$)R$^{d4}$-A$^4$-C(Q$^{c4}$)OR$^{e4}$, -A$^{d4}$-S(O)$_p$R$^{f4}$, -A$^{e4}$-S(O)$_q$N(R$^{g4}$)R$^{h4}$, -A$^{f4}$-S(O)$_p$OR$^{i4}$, —N$_3$, —N(R$^{j4}$)R$^{k4}$, —N(H)CN, —NO$_2$, —ONO$_2$, halo, R$^{a4}$, —OR$^{l4}$ or —SR$^{m4}$ (such as halo, R$^4$, —OR$^{l4}$ or —SR$^{m4}$);

each Q$^{a4}$ to Q$^{c4}$ independently represents =O, =S, =NR$^{n4}$ or =N(OR$^{o4}$) (such as =O); and/or (e.g. and)

each A$^{a4}$ to A$^{f4}$ independently represents a single bond, —N(R$^{p4}$)— or —O—.

In particular embodiments, p represents 2 and/or (e.g. and) q represents 2.

In a particular embodiment of the first aspect of the invention, the compound of formula I is not N-(1-(2,4-difluorophenyl)-4,5,6,7-tetrahydro-1H-indazol-4-yl)picolinamide.

Particular compounds of the first aspect of the invention that may be mentioned include the compounds of the examples provided herein, and pharmaceutically acceptable salts thereof.

More particular compounds of the first aspect of the invention that may be mentioned include:

N-(1-(2-Fluorophenyl)-4,5,6,7-tetrahydro-1H-indazol-4-yl)picolinamide;

(S)—N-(1-(2-Fluorophenyl)-4,5,6,7-tetrahydro-1H-indazol-4-yl)picolinamide;

(R)—N-(1-(2-fluorophenyl)-4,5,6,7-tetrahydro-1H-indazol-4-yl)picolinamide;

N-[1-(2-fluorophenyl)-4,5,6,7-tetrahydro-1H-indazol-4-yl]-1,3-thiazole-4-carboxamide;

N-(1-(2,4-difluorophenyl)-4,5,6,7-tetrahydro-1H-indazol-4-yl)-4,5,6,7-tetrahydrobenzo[c]isoxazole-3-carboxamide;

N-[1-(3,4-dimethylphenyl)-4,5,6,7-tetrahydro-1H-indazol-4-yl]-5-methyl-3-isoxazolecarboxamide;

Methyl 6-({[1-(2-fluorophenyl)-4,5,6,7-tetrahydro-1H-indazol-4-yl]amino}carbonyl) nicotinate;

N-(1-(2-fluorophenyl)-4,5,6,7-tetrahydro-1H-indazol-4-yl)-4,5,6,7-tetrahydrobenzo[c]isoxazole-3-carboxamide;

Methyl 6-({[1-(3,5-difluorophenyl)-4,5,6,7-tetrahydro-1H-indazol-4-yl]amino}carbonyl)nicotinate;

N-[1-(2,4-difluorophenyl)-4,5,6,7-tetrahydro-1H-indazol-4-yl]-5-ethyl-3-isoxazolecarboxamide;

N-[1-(2,4-difluorophenyl)-4,5,6,7-tetrahydro-1H-indazol-4-yl]-2-(methylthio)-1,3-thiazole-4-carboxamide;

(R)—N-[1-(2,4-difluorophenyl)-4,5,6,7-tetrahydro-1H-indazol-4-yl]-4,5,6,7-tetrahydro-1,2-benzisoxazole-3-carboxamide;

N-[(4R)-1-(2,4-difluorophenyl)-4,5,6,7-tetrahydro-1H-indazol-4-yl]-4,5,6,7-tetrahydro-2,1-benzoxazole-3-carboxamide;

N-[(4R)-1-(2-fluorophenyl)-4,5,6,7-tetrahydro-1H-indazol-4-yl]-4,5,6,7-tetrahydro-1,2-benzoxazole-3-carboxamide;

N-[(4R)-1-(2-fluorophenyl)-4,5,6,7-tetrahydro-1H-indazol-4-yl]-4,5,6,7-tetrahydro-2,1-benzoxazole-3-carboxamide;

N-[(4R)-1-(2-fluorophenyl)-4,5,6,7-tetrahydro-1H-indazol-4-yl]-5-methylpyrazine-2-carboxamide;

N-[(4R)-1-(2-methylphenyl)-4,5,6,7-tetrahydro-1H-indazol-4-yl]-4,5,6,7-tetrahydro-2,1-benzoxazole-3-carboxamide;

N-[(4R)-1-(2-methylphenyl)-4,5,6,7-tetrahydro-1H-indazol-4-yl]-1-benzofuran-2-carboxamide;

3-methyl-N-[(4R)-1-(2-methylphenyl)-4,5,6,7-tetrahydro-1H-indazol-4-yl]-1-benzofuran-2-carboxamide;

N-[(4R)-1-(2-methylphenyl)-4,5,6,7-tetrahydro-1H-indazol-4-yl]pyridine-2-carboxamide; 3-methyl-N-[(4R)-1-(2-methylphenyl)-4,5,6,7-tetrahydro-1H-indazol-4-yl]thiophene-2-carboxamide;

N-[(4R)-1-(2-methylphenyl)-4,5,6,7-tetrahydro-1H-indazol-4-yl]pyridine-2-carboxamide; 2-hydroxy-N-[(4R)-1-(2-methylphenyl)-4,5,6,7-tetrahydro-1H-indazol-4-yl]pyridine-3-carboxamide;

N-(1-phenyl-4,5,6,7-tetrahydro-1H-indazol-4-yl)-4,5,6,7-tetrahydro-1,2-benzoxazole-3-carboxamide;

N-(1-phenyl-4,5,6,7-tetrahydro-1H-indazol-4-yl)pyridine-2-carboxamide;

5-methyl-N-[(4R)-1-(2-methylphenyl)-4,5,6,7-tetrahydro-1H-indazol-4-yl]pyridine-2-carboxamide; 4-methyl-N-[(4R)-1-(2-methylphenyl)-4,5,6,7-tetrahydro-1H-indazol-4-yl]pyridine-2-carboxamide;

3-methyl-N-[(4R)-1-(2-methylphenyl)-4,5,6,7-tetrahydro-1H-indazol-4-yl]pyridine-2-carboxamide;

N-(1-phenyl-4,5,6,7-tetrahydro-1H-indazol-4-yl)-4,5,6,7-tetrahydro-2,1-benzoxazole-3-carboxamide;

N-[(4R)-1-(2-fluorophenyl)-4,5,6,7-tetrahydro-1H-indazol-4-yl]-1,2-benzoxazole-3-carboxamide;

N-[1-(2-methylphenyl)-4,5,6,7-tetrahydro-1H-indazol-4-yl]-4,5,6,7-tetrahydro-1,2-benzoxazole-3-carboxamide;

N-[1-(3-methylphenyl)-4,5,6,7-tetrahydro-1H-indazol-4-yl]-4,5,6,7-tetrahydro-1,2-benzoxazole-3-carboxamide;

N-[1-(2,3-dimethylphenyl)-4,5,6,7-tetrahydro-1H-indazol-4-yl]-4,5,6,7-tetrahydro-1,2-benzoxazole-3-carboxamide;

Ethyl 3-[4-(4,5,6,7-tetrahydro-1,2-benzoxazole-3-amido)-4,5,6,7-tetrahydro-1H-indazol-1-yl]benzoate; and N-[(4R)-1-(2-fluorophenyl)-4,5,6,7-tetrahydro-1H-indazol-4-yl]-1,3-benzoxazole-2-carboxamide, and pharmaceutically acceptable salts thereof.

Yet more particular compounds of the first aspect of the invention that may be mentioned include:

N-(1-(2-Fluorophenyl)-4,5,6,7-tetrahydro-1H-indazol-4-yl)picolinamide;

(S)—N-(1-(2-Fluorophenyl)-4,5,6,7-tetrahydro-1H-indazol-4-yl)picolinamide;

(R)—N-(1-(2-fluorophenyl)-4,5,6,7-tetrahydro-1H-indazol-4-yl)picolinamide;
N-[1-(2-fluorophenyl)-4,5,6,7-tetrahydro-1H-indazol-4-yl]-1,3-thiazole-4-carboxamide;
N-(1-(2,4-difluorophenyl)-4,5,6,7-tetrahydro-1H-indazol-4-yl)-4,5,6,7-tetrahydrobenzo[c]isoxazole-3-carboxamide;
N-[1-(3,4-dimethylphenyl)-4,5,6,7-tetrahydro-1H-indazol-4-yl]-5-methyl-3-isoxazolecarboxamide;
Methyl 6-({[1-(2-fluorophenyl)-4,5,6,7-tetrahydro-1H-indazol-4-yl]amino}carbonyl) nicotinate
N-(1-(2-fluorophenyl)-4,5,6,7-tetrahydro-1H-indazol-4-yl)-4,5,6,7-tetrahydrobenzo[c]isoxazole-3-carboxamide;
Methyl 6-({[1-(3,5-difluorophenyl)-4,5,6,7-tetrahydro-1H-indazol-4-yl]amino}carbonyl) nicotinate;
N-[1-(2,4-difluorophenyl)-4,5,6,7-tetrahydro-1H-indazol-4-yl]-5-ethyl-3-isoxazolecarboxamide;
N-[1-(2,4-difluorophenyl)-4,5,6,7-tetrahydro-1H-indazol-4-yl]-2-(methylthio)-1,3-thiazole-4-carboxamide;
N-[(4R)-1-(2-fluorophenyl)-4,5,6,7-tetrahydro-1H-indazol-4-yl]-4,5,6,7-tetrahydro-1,2-benzoxazole-3-carboxamide;
N-[(4R)-1-(2-fluorophenyl)-4,5,6,7-tetrahydro-1H-indazol-4-yl]-4,5,6,7-tetrahydro-2,1-benzoxazole-3-carboxamide;
N-[(4R)-1-(2-fluorophenyl)-4,5,6,7-tetrahydro-1H-indazol-4-yl]-5-methylpyrazine-2-carboxamide;
N-[(4R)-1-(2-methylphenyl)-4,5,6,7-tetrahydro-1H-indazol-4-yl]-4,5,6,7-tetrahydro-2,1-benzoxazole-3-carboxamide;
N-[(4R)-1-(2-methylphenyl)-4,5,6,7-tetrahydro-1H-indazol-4-yl]-1-benzofuran-2-carboxamide;
3-methyl-N-[(4R)-1-(2-methylphenyl)-4,5,6,7-tetrahydro-1H-indazol-4-yl]-1-benzofuran-2-carboxamide;
N-[(4R)-1-(2-methylphenyl)-4,5,6,7-tetrahydro-1H-indazol-4-yl]pyridine-2-carboxamide;
3-methyl-N-[(4R)-1-(2-methylphenyl)-4,5,6,7-tetrahydro-1H-indazol-4-yl]thiophene-2-carboxamide;
N-[(4R)-1-(2-methylphenyl)-4,5,6,7-tetrahydro-1H-indazol-4-yl]pyridine-2-carboxamide;
2-hydroxy-N-[(4R)-1-(2-methylphenyl)-4,5,6,7-tetrahydro-1H-indazol-4-yl]pyridine-3-carboxamide;
N-(1-phenyl-4,5,6,7-tetrahydro-1H-indazol-4-yl)-4,5,6,7-tetrahydro-1,2-benzoxazole-3-carboxamide;
N-(1-phenyl-4,5,6,7-tetrahydro-1H-indazol-4-yl)pyridine-2-carboxamide;
5-methyl-N-[(4R)-1-(2-methylphenyl)-4,5,6,7-tetrahydro-1H-indazol-4-yl]pyridine-2-carboxamide;
4-methyl-N-[(4R)-1-(2-methylphenyl)-4,5,6,7-tetrahydro-1H-indazol-4-yl]pyridine-2-carboxamide;
3-methyl-N-[(4R)-1-(2-methylphenyl)-4,5,6,7-tetrahydro-1H-indazol-4-yl]pyridine-2-carboxamide;
N-(1-phenyl-4,5,6,7-tetrahydro-1H-indazol-4-yl)-4,5,6,7-tetrahydro-2,1-benzoxazole-3-carboxamide;
N-[(4R)-1-(2-fluorophenyl)-4,5,6,7-tetrahydro-1H-indazol-4-yl]-1,2-benzoxazole-3-carboxamide;
N-[1-(2-methylphenyl)-4,5,6,7-tetrahydro-1H-indazol-4-yl]-4,5,6,7-tetrahydro-1,2-benzoxazole-3-carboxamide;
N-[1-(3-methylphenyl)-4,5,6,7-tetrahydro-1H-indazol-4-yl]-4,5,6,7-tetrahydro-1,2-benzoxazole-3-carboxamide;
N-[1-(2,3-dimethylphenyl)-4,5,6,7-tetrahydro-1H-indazol-4-yl]-4,5,6,7-tetrahydro-1,2-benzoxazole-3-carboxamide;
Ethyl 3-[4-(4,5,6,7-tetrahydro-1,2-benzoxazole-3-amido)-4,5,6,7-tetrahydro-1H-indazol-1-yl]benzoate; and
N-[(4R)-1-(2-fluorophenyl)-4,5,6,7-tetrahydro-1H-indazol-4-yl]-1,3-benzoxazole-2-carboxamide,
and pharmaceutically acceptable salts thereof.

Yet more particular compounds of formula I that may be mentioned include:
N-(1-(2-fluorophenyl)-4,5,6,7-tetrahydro-1H-indazol-4-yl)picolinamide;
N-(1-(2,4-difluorophenyl)-4,5,6,7-tetrahydro-1H-indazol-4-yl)-4,5,6,7-tetrahydrobenzo[c]isoxazole-3-carboxamide; and
N-(1-(2-fluorophenyl)-4,5,6,7-tetrahydro-1H-indazol-4-yl)-4,5,6,7-tetrahydrobenzo[c]isoxazole-3-carboxamide,
and pharmaceutically acceptable salts thereof.

Yet more particular compounds of formula I that may be mentioned include:
N-(1-(2-fluorophenyl)-4,5,6,7-tetrahydro-1H-indazol-4-yl)picolinamide,
and pharmaceutically acceptable salts thereof.

Yet more particular compounds of formula I that may be mentioned include:
N-(1-(2-fluorophenyl)-4,5,6,7-tetrahydro-1H-indazol-4-yl)-4,5,6,7-tetrahydrobenzo[c]isoxazole-3-carboxamide,
and pharmaceutically acceptable salts thereof.

As described wherein, compounds of the first aspect of the invention may exist as stereoisomers. In particular, compounds of the first aspect of the invention may exist as stereoisomers at the position marked with an asterisk in formula I as depicted herein above, at which position the skilled person will understand that compounds of the first aspect of the invention may exist in the R- or S-configuration.

For the avoidance of doubt, the skilled person will understand that, where the carbon marked with an asterisk in formula I as depicted herein above is the only stereo centre in the compound of formula I, the compound of formula I may exist in the form of two enantiomers having differing configurations at that stereo centre, which enantiomers may be referred to as the R- and S-enantiomers (indicating the configuration at that position, as understood by one skilled in the art).

In particular, compounds of the first aspect of the invention may exists as mixtures (e.g. about equal mixtures) of stereoisomers, i.e. mixtures of each possible stereoisomer. In particular, where compounds of the invention exist as R- and S-enantiomers (i.e. in the R- and S-configurations at the carbon marked with an asterisk in the compound of formula I as depicted above), the compound of the first aspect of the invention may be a mixture of those enantiomers, particularly an about equal mixture (e.g. a racemic mixture).

In other embodiments, the compound of the first aspect of the invention may exist in either the R- or S-configuration at the marked carbon (e.g. as either the R- or S-enantiomer), in which case the compound may exist in the substantial absence of compounds of the alternative configuration (e.g. in greater than 60%, such as greater than 70%, greater than 80% or greater than 90% (e.g. greater than 99%, such as greater than or equal to 99.9%) purity relative to the alternative configuration.

For example, where the compound of the first aspect of the invention exists as either the R- or S-enantiomer as described herein above, that compound may have an enantiomeric excess (e.e.) as understood by one skilled in the art, of greater than greater than 60%, such as greater than 70%, greater than 80% or greater than 90% (e.g. greater than 99%, such as greater than or equal to 99.9%).

In particular, the compound of the first aspect of the invention may exist as the R-enantiomer as described herein above.

Thus, in a particular embodiment of the first aspect of the invention, the compound of formula I is a compound of formula Ia

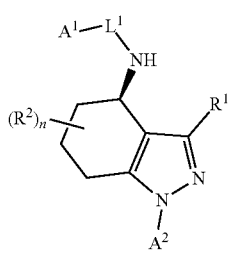

(Ia)

wherein $A^1$, $A^2$, $L^1$, $R^1$, $R^2$ and n are as defined in the first aspect of the invention (including all embodiments and combinations of embodiments thereof).

For the avoidance of doubt, there is therefore provided in a particular embodiment of the first aspect of the invention a compound of formula Ia, or a pharmaceutically acceptable salt thereof, for use on the treatment of cancer.

In particular, the compound of formula Ia is provided in the substantial absence of the compound of formula I, or pharmaceutically acceptable salt thereof, in the alternative configuration, e.g. a compound of formula Ib

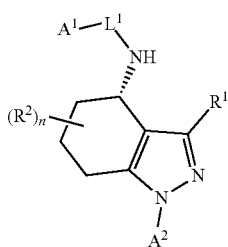

(Ib)

wherein $A^1$, $A^2$, $L^1$, $R^1$, $R^2$ and n are as defined in the first aspect of the invention (including all embodiments and combinations of embodiments thereof), or a pharmaceutically acceptable salt thereof.

In particular, the compound of formula Ia, or a pharmaceutically acceptable salt thereof, may be provided in greater than 60%, such as greater than 70%, greater than 80% or greater than 90% (e.g. greater than 99%, such as greater than or equal to 99.9%) purity relative to the compound of Ib or a pharmaceutically acceptable salt thereof (e.g. where present in greater than 90% purity, the compounds of formula Ia, or a pharmaceutically acceptable salt thereof, will make up greater than 90% of the combined amount of compounds of formula Ia and Ib, and pharmaceutically acceptable salts thereof).

In alternative embodiments, references to the R-enantiomer or compound of formula Ia may be replaced with references to the S-enantiomer or compound of formula Ib, and vice versa.

For example, the compound of the first aspect of the invention may be provided as a compound of formula Ib, or a pharmaceutically acceptable salt thereof, in greater than 60%, such as greater than 70%, greater than 80% or greater than 90% (e.g. greater than 99%, such as greater than or equal to 99.9%) purity relative to the compound of Ia or a pharmaceutically acceptable salt thereof.

In an alternative first aspect of the invention, there is provided a method of treating cancer and/or treating or preventing a viral infection comprising administering to a patient in need thereof a therapeutically effective amount of a compound of formula I, or a pharmaceutically acceptable salt thereof, as defined in the first aspect of the invention (including all embodiments and combinations of embodiments thereof).

In a further alternative first aspect of the invention, there is provided a compound of formula I, or a pharmaceutically acceptable salt thereof, as defined in the first aspect of the invention (including all embodiments and combinations of embodiments thereof) for use in the manufacture of a medicament for the treatment of cancer and/or the treatment or prevention of a viral infection.

The skilled person will understand that references to the treatment of a particular condition (or, similarly, to treating that condition) take their normal meaning in the field of medicine. In particular, the terms may refer to achieving a reduction in the severity of one or more clinical symptom associated with the condition. For example, in the case of a cancer, the term may refer to achieving a reduction of the amount of cancerous cells present (e.g. in the case of a cancer forming a solid tumour, indicated by a reduction in tumour volume). Similarly, in the case of a viral infection, the term may refer to achieving a reduction in the viral load (i.e. the number of viral units present in a given amount of plasma in the relevant patient, e.g. the number of viral units per mL of plasma).

The skilled person will understand that references to the prevention of a particular condition (and, similarly, to preventing that condition) take their normal meaning in the field of medicine, and include references to the prophylaxis of the condition (and vice-versa). In particular, the term may refer to achieving a reduction in the likelihood of the patient (or a healthy subject) developing the condition (for example, at least a 10% reduction, such as at least a 20%, 30% or 40% reduction, e.g. at least a 50% reduction).

As used herein, references to patients will refer to a living subject being treated, including mammalian (e.g. human) patients. Thus, in particular embodiments of the first aspect of the invention, the treatment is in a mammal (e.g. a human).

As used herein, the term therapeutically effective amount will refer to an amount of a compound that confers a therapeutic effect on the treated patient. The effect may be objective (i.e. measurable by some test or marker) or subjective (i.e. the subject gives an indication of and/or feels an effect).

Although compounds of the first aspect of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the first aspect of the invention are included within the scope of the invention.

For the avoidance of doubt, the compounds of the first aspect of the invention are useful because they possess pharmacological activity, and/or are metabolised in the body following oral or parenteral administration to form compounds that possess pharmacological activity. In particular, as described herein, compounds of the first aspect of the invention are useful in the treatment of cancer, which term will be readily understood by one of skill in the art.

In a particular embodiment of all aspects of the invention, references to the treatment of cancer and/or the treatment or prevention of a viral infection will refer in particular to the treatment of cancer.

In an alternative embodiment of all aspects of the invention, references to the treatment of cancer and/or the treatment or prevention of a viral infection will refer in particular to the treatment or prevention (more particularly, the treatment) of a viral infection.

In particular embodiments of the first aspect of the invention, the cancer is a cancer selected from the list consisting of:
soft tissue cancers, such as sarcoma, myxoma, rhabdomyoma, fibroma, lipoma and teratoma;
lung cancers, such as bronchogenic carcinoma, alveolar or bronchiolar carcinoma, bronchial adenoma, sarcoma, lymphoma, chondromatous hamartoma, mesothelioma; gastrointestinal cancers, such as esophageal cancers, stomach cancers, pancreatic cancers, small bowel cancers, large bowel cancers (e.g. colon cancer);
genitourinary tract cancers, such as cancer of the kidney, bladder and urethra, prostate, testis;
liver cancers, such as hepatoma, cholangiocarcinoma, hepatoblastoma, angiosarcoma, hepatocellular adenoma, hemangioma;
bone cancers, such as osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors;
cancers of the head and/or nervous system, such as cancers of the skull, meninges, brain, spinal cord;
gynecological cancers, such as cancers of the uterus, cervix, ovaries, cancers of the vulva, vagina, fallopian tubes;
haematologic cancers, such as cancers of the blood and bone marrow (e.g. leukemia, such as acute myeloid leukemia, chronic myeloid leukemia), Hodgkin's disease, non-Hodgkin's lymphoma and Burkitt's lymphoma;
skin cancers, such as malignant melanoma, basal cell carcinoma, squamous cell carcinoma, Kaposi's sarcoma, moles dysplastic nevi, lipoma, angioma, dermatofibroma, keloids; neurofibromatosis and adrenal glands; and neuroblastomas.

As used herein, references to cancerous cells and the like will include references to a cell afflicted by any one of the above-identified conditions.

More particular cancers that may be mentioned include those corresponding to the cell lines used in the examples provided herein. For example, particular cancers that may be mentioned include:
colon cancer;
skin cancer (e.g. as defined herein, such as malignant melanoma);
lymphomas;
leukemia (such as chronic myeloid leukemia); and
sarcomas (such as those described herein).

In more particular embodiments, the cancer is selected from the group consisting of a skin cancer (such as malignant melanoma) and a haematologic cancer (such as chronic myeloid leukemia). For example, the cancer may be a skin cancer as known to those skilled in the art, such as a skin cancer as described herein.

More particularly, the cancer may be chronic myeloid leukemia (CML) or malignant melanoma. Most particularly, the cancer may be malignant melanoma.

In particular embodiments of the first aspect of the invention, references to a viral infection will refer to an infection caused by one or more virus selected from severe acute respiratory syndrome (SARS), Middle East respiratory syndrome (MERS), Western/Eastern equine encephalitis (WEE/EEE), Ebola and influenza, such as pandemic influenza (e.g. H1N1).

The skilled person will understand that treatment with compounds of the first aspect of the invention may further comprise (i.e. be combined with) further (i.e. additional/other) treatment(s) for the same condition.

For example, when used in the treatment of cancers, treatment with compounds of the invention may be combined with other means for the treatment of cancer, such as treatment with one or more other therapeutic agent that is useful in the treatment of cancer (including treatment with cell-based therapies, such as immunotherapies) and/or one or more physical method used in the treatment of cancer (such as treatment through surgery and/or radiotherapy), as known to those skilled in the art.

Thus, treatment with compounds of the first aspect of the invention may further comprise (i.e. be combined with) further (i.e. additional/other) treatment(s) for cancer (such treatment with an additional agent for the treatment of a cancer as described herein, e.g. malignant melanoma).

In particular, treatment with compounds of the invention may be performed in combination with (e.g. in a patent who is also being treated with) one or more (e.g. one) additional compounds (i.e. therapeutic agents) that:
(i) are capable of reducing levels of nucleosides and/or nucleotides within a cell (e.g. a cancerous cell); and/or
(ii) are activators of p53 (such as inhibitors of MDM2), both of which are described herein below.

Similarly, when used in the treatment or prevention of viral infections, treatment or prevention using compounds of the invention may be performed in combination with one or more other therapeutic agent that is useful in the treatment or prevention of a viral infection, as known to those skilled in the art.

Novel Compounds and Uses

As described herein, compounds of the first aspect of the invention may exist as stereoisomers. Further, certain stereoisomers of compounds of the invention may be novel.

In a second aspect of the invention, there is provided a compound of formula Ia

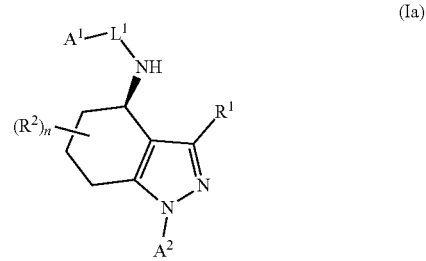

or a pharmaceutically acceptable salt thereof, wherein $A^1$, $A^2$, $L^1$, $R^1$, $R^2$ and n are as defined in the first aspect of the invention (including all embodiments and combinations of embodiments thereof).

In particular embodiments, the compound of formula Ia, or a pharmaceutically acceptable salt thereof, may be provided in greater than 60%, such as greater than 70%, greater than 80% or greater than 90% (e.g. greater than 99%, such as greater than or equal to 99.9%) purity relative to a compound of Ib, as defined herein, or a pharmaceutically acceptable salt thereof (e.g. where present in greater than 90% purity, the compounds of formula Ia, or a pharmaceutically acceptable salt thereof, will make up greater than 90% of the combined amount of compounds of formula Ia and Ib, and pharmaceutically acceptable salts thereof).

In a particular embodiment of the second aspect of the invention, the compound of formula Ia is not (R)—N-(1-(2,4-difluorophenyl)-4,5,6,7-tetrahydro-1H-indazol-4-yl)picolinamide.

Particular compounds of the second aspect of the invention that may be mentioned include:
- (S)—N-(1-(2-fluorophenyl)-4,5,6,7-tetrahydro-1H-indazol-4-yl)picolinamide;
- (R)—N-(1-(2-fluorophenyl)-4,5,6,7-tetrahydro-1H-indazol-4-yl)picolinamide;
- (R)—N-[1-(2,4-difluorophenyl)-4,5,6,7-tetrahydro-1H-indazol-4-yl]-4,5,6,7-tetrahydro-1,2-benzisoxazole-3-carboxamide;
- N-[(4R)-1-(2,4-difluorophenyl)-4,5,6,7-tetrahydro-1H-indazol-4-yl]-4,5,6,7-tetrahydro-2,1-benzoxazole-3-carboxamide;
- N-[(4R)-1-(2-fluorophenyl)-4,5,6,7-tetrahydro-1H-indazol-4-yl]-4,5,6,7-tetrahydro-1,2-benzoxazole-3-carboxamide;
- N-[(4R)-1-(2-fluorophenyl)-4,5,6,7-tetrahydro-1H-indazol-4-yl]-4,5,6,7-tetrahydro-2,1-benzoxazole-3-carboxamide;
- N-[(4R*)-1-(2-fluorophenyl)-4,5,6,7-tetrahydro-1H-indazol-4-yl]-5-methylpyrazine-2-carboxamide;
- N-[(4R)-1-(2-methylphenyl)-4,5,6,7-tetrahydro-1H-indazol-4-yl]-4,5,6,7-tetrahydro-2,1-benzoxazole-3-carboxamide;
- N-[(4R)-1-(2-methylphenyl)-4,5,6,7-tetrahydro-1H-indazol-4-yl]-1-benzofuran-2-carboxamide;
- 3-methyl-N-[(4R)-1-(2-methylphenyl)-4,5,6,7-tetrahydro-1H-indazol-4-yl]-1-benzofuran-2-carboxamide;
- N-[(4R)-1-(2-methylphenyl)-4,5,6,7-tetrahydro-1H-indazol-4-yl]pyridine-2-carboxamide;
- 3-methyl-N-[(4R)-1-(2-methylphenyl)-4,5,6,7-tetrahydro-1H-indazol-4-yl]thiophene-2-carboxamide;
- N-[(4R)-1-(2-methylphenyl)-4,5,6,7-tetrahydro-1H-indazol-4-yl]pyridine-2-carboxamide;
- 2-hydroxy-N-[(4R)-1-(2-methylphenyl)-4,5,6,7-tetrahydro-1H-indazol-4-yl]pyridine-3-carboxamide;
- 5-methyl-N-[(4R)-1-(2-methylphenyl)-4,5,6,7-tetrahydro-1H-indazol-4-yl]pyridine-2-carboxamide;
- 4-methyl-N-[(4R)-1-(2-methylphenyl)-4,5,6,7-tetrahydro-1H-indazol-4-yl]pyridine-2-carboxamide;
- 3-methyl-N-[(4R)-1-(2-methylphenyl)-4,5,6,7-tetrahydro-1H-indazol-4-yl]pyridine-2-carboxamide;
- N-[(4R)-1-(2-fluorophenyl)-4,5,6,7-tetrahydro-1H-indazol-4-yl]-1,2-benzoxazole-3-carboxamide; and
- N-[(4R)-1-(2-fluorophenyl)-4,5,6,7-tetrahydro-1H-indazol-4-yl]-1,3-benzoxazole-2-carboxamide, and pharmaceutically acceptable salts thereof.

More particular compounds of the second aspect of the invention that may be mentioned include:
- (S)—N-(1-(2-fluorophenyl)-4,5,6,7-tetrahydro-1H-indazol-4-yl)picolinamide;
- (R)—N-(1-(2-fluorophenyl)-4,5,6,7-tetrahydro-1H-indazol-4-yl)picolinamide;
- N-[(4R)-1-(2-fluorophenyl)-4,5,6,7-tetrahydro-1H-indazol-4-yl]-4,5,6,7-tetrahydro-1,2-benzoxazole-3-carboxamide;
- N-[(4R)-1-(2-fluorophenyl)-4,5,6,7-tetrahydro-1H-indazol-4-yl]-4,5,6,7-tetrahydro-2,1-benzoxazole-3-carboxamide;
- N-[(4R*)-1-(2-fluorophenyl)-4,5,6,7-tetrahydro-1H-indazol-4-yl]-5-methylpyrazine-2-carboxamide;
- N-[(4R)-1-(2-methylphenyl)-4,5,6,7-tetrahydro-1H-indazol-4-yl]-4,5,6,7-tetrahydro-2,1-benzoxazole-3-carboxamide;
- N-[(4R)-1-(2-methylphenyl)-4,5,6,7-tetrahydro-1H-indazol-4-yl]-1-benzofuran-2-carboxamide;
- 3-methyl-N-[(4R)-1-(2-methylphenyl)-4,5,6,7-tetrahydro-1H-indazol-4-yl]-1-benzofuran-2-carboxamide;
- N-[(4R)-1-(2-methylphenyl)-4,5,6,7-tetrahydro-1H-indazol-4-yl]pyridine-2-carboxamide;
- 3-methyl-N-[(4R)-1-(2-methylphenyl)-4,5,6,7-tetrahydro-1H-indazol-4-yl]thiophene-2-carboxamide;
- N-[(4R)-1-(2-methylphenyl)-4,5,6,7-tetrahydro-1H-indazol-4-yl]pyridine-2-carboxamide;
- 2-hydroxy-N-[(4R)-1-(2-methylphenyl)-4,5,6,7-tetrahydro-1H-indazol-4-yl]pyridine-3-carboxamide;
- 5-methyl-N-[(4R)-1-(2-methylphenyl)-4,5,6,7-tetrahydro-1H-indazol-4-yl]pyridine-2-carboxamide;
- 4-methyl-N-[(4R)-1-(2-methylphenyl)-4,5,6,7-tetrahydro-1H-indazol-4-yl]pyridine-2-carboxamide;
- 3-methyl-N-[(4R)-1-(2-methylphenyl)-4,5,6,7-tetrahydro-1H-indazol-4-yl]pyridine-2-carboxamide;
- N-[(4R)-1-(2-fluorophenyl)-4,5,6,7-tetrahydro-1H-indazol-4-yl]-1,2-benzoxazole-3-carboxamide; and
- N-[(4R)-1-(2-fluorophenyl)-4,5,6,7-tetrahydro-1H-indazol-4-yl]-1,3-benzoxazole-2-carboxamide, and pharmaceutically acceptable salts thereof.

Yet more particular compounds of formula Ia that may be mentioned (in relation to the first and second aspects of the invention, and all aspects of the invention referring thereto) include:
- (R)—N-(1-(2-fluorophenyl)-4,5,6,7-tetrahydro-1H-indazol-4-yl)picolinamide;
- (R)—N-[1-(2,4-difluorophenyl)-4,5,6,7-tetrahydro-1H-indazol-4-yl]-4,5,6,7-tetrahydro-1,2-benzisoxazole-3-carboxamide;
- N-[(4R)-1-(2,4-difluorophenyl)-4,5,6,7-tetrahydro-1H-indazol-4-yl]-4,5,6,7-tetrahydro-2,1-benzoxazole-3-carboxamide; and
- (R)—N-[1-(2-fluorophenyl)-4,5,6,7-tetrahydro-1H-indazol-4-yl]-4,5,6,7-tetrahydro-1,2-benzisoxazole-3-carboxamide, and pharmaceutically acceptable salts thereof.

More particular compounds of formula Ia that may be mentioned (in relation to the first and second aspects of the invention, and all aspects of the invention referring thereto) include:
- (R)—N-(1-(2-fluorophenyl)-4,5,6,7-tetrahydro-1H-indazol-4-yl)picolinamide, and pharmaceutically acceptable salts thereof.

Yet more particular compounds of formula Ia that may be mentioned (in relation to the first and second aspects of the invention, and all aspects of the invention referring thereto) include:
- N-[(4R)-1-(2,4-difluorophenyl)-4,5,6,7-tetrahydro-1H-indazol-4-yl]-4,5,6,7-tetrahydro-2,1-benzoxazole-3-carboxamide, and pharmaceutically acceptable salts thereof.

Further compounds of the second aspect of the invention that may be mentioned include:
- (R)—N-(1-(2-methylphenyl)-4,5,6,7-tetrahydro-1H-indazol-4-yl)-4,5,6,7-tetrahydrobenzo[d]isoxazole-3-carboxamide;

N-[(4R)-1-(2-fluorophenyl)-4,5,6,7-tetrahydro-1H-indazol-4-yl]-1H-indole-2-carboxamide;
4-chloro-N-[(4R)-1-(2-fluorophenyl)-4,5,6,7-tetrahydro-1H-indazol-4-yl]pyridine-2-carboxamide;
4-bromo-N-[(4R)-1-(2-fluorophenyl)-4,5,6,7-tetrahydro-1H-indazol-4-yl]pyridine-2-carboxamide;
(R)—N-(1-(2-fluorophenyl)-4,5,6,7-tetrahydro-1H-indazol-4-yl)-4-methoxyquinoline-2-carboxamide;
N-[(4R)-1-(2-fluorophenyl)-4,5,6,7-tetrahydro-1H-indazol-4-yl]-4-(trifluoromethyl)pyridine-2-carboxamide;
N-[(4R)-1-(2-fluorophenyl)-4,5,6,7-tetrahydro-1H-indazol-4-yl]-5-(trifluoromethyl)pyridine-2-carboxamide;
N-[(4R)-1-(2-fluorophenyl)-4,5,6,7-tetrahydro-1H-indazol-4-yl]-5-methylpyridine-2-carboxamide;
(R)—N-(1-(2-fluorophenyl)-4,5,6,7-tetrahydro-1H-indazol-4-yl)-4-methylpicolinamide;
N-[(4R)-1-(2-fluorophenyl)-4,5,6,7-tetrahydro-1H-indazol-4-yl]-4,5-dimethylpyridine-2-carboxamide;
6-methyl-N-[(4R)-1-(2-methylphenyl)-4,5,6,7-tetrahydro-1H-indazol-4-yl]pyridine-2-carboxamide;
(R)—N-(1-(2-fluorophenyl)-4,5,6,7-tetrahydro-1H-indazol-4-yl)-5,6,7,8-tetrahydroimidazo[1,5-a]pyridine-1-carboxamide;
4-fluoro-N-[(4R)-1-(2-fluorophenyl)-4,5,6,7-tetrahydro-1H-indazol-4-yl]pyridine-2-carboxamide;
(R)—N-(1-(2-fluorophenyl)-4,5,6,7-tetrahydro-1H-indazol-4-yl)imidazo[1,5-a]pyridine-3-carboxamide;
(R)—N-(1-(2-fluoro-5-methylphenyl)-4,5,6,7-tetrahydro-1H-indazol-4-yl)-4,5,6,7-tetrahydrobenzo[c]isoxazole-3-carboxamide;
N-[(4R)-1-(2-fluoro-5-methylphenyl)-4,5,6,7-tetrahydro-1H-indazol-4-yl]-4-(trifluoromethyl)pyridine-2-carboxamide;
N-[(4R)-1-(2-fluoro-5-methylphenyl)-4,5,6,7-tetrahydro-1H-indazol-4-yl]-4-methylpyridine-2-carboxamide;
propan-2-yl-3-[(4R)-4-(4,5,6,7-tetrahydro-1,2-benzoxazole-3-amido)-4,5,6,7-tetrahydro-1H-indazol-1-yl]benzoate; and
N-[(4R)-1-[3-(morpholine-4-carbonyl)phenyl]-4,5,6,7-tetrahydro-1H-indazol-4-yl]-4,5,6,7-tetrahydro-1,2-benzoxazole-3-carboxamide,
and pharmaceutically acceptable salts thereof.

In an alternative second aspect of the invention, there is provided a compound of formula Ib

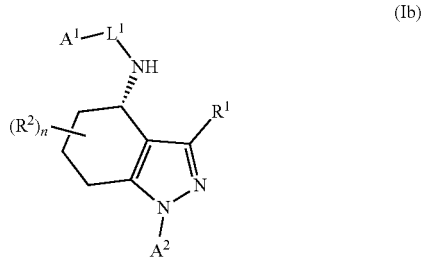

or a pharmaceutically acceptable salt thereof, wherein $A^1$, $A^2$, $L^1$, $R^1$, $R^2$ and n are as defined in the first aspect of the invention (including all embodiments and combinations of embodiments thereof).

In particular embodiments, the compound of formula Ib, or a pharmaceutically acceptable salt thereof, may be provided in greater than 60%, such as greater than 70%, greater than 80% or greater than 90% (e.g. greater than 99%, such as greater than or equal to 99.9%) purity relative to a compound of Ia, as defined herein, or a pharmaceutically acceptable salt thereof (e.g. where present in greater than 90% purity, the compounds of formula Ib, or a pharmaceutically acceptable salt thereof, will make up greater than 90% of the combined amount of compounds of formula Ia and Ib, and pharmaceutically acceptable salts thereof).

In a particular embodiment of the second aspect of the invention, the compound of formula Ib is not (S)—N-(1-(2,4-difluorophenyl)-4,5,6,7-tetrahydro-1H-indazol-4-yl)picolinamide.

Particular compounds of formula Ib that may be mentioned (in relation to the first and second aspects of the invention, and all aspects of the invention referring thereto) include:
(S)—N-(1-(2-fluorophenyl)-4,5,6,7-tetrahydro-1H-indazol-4-yl)picolinamide,
and pharmaceutically acceptable salts thereof.

As described herein, compounds of the first and, therefore, second aspects of the invention are therapeutically active.

In a third aspect of the invention, there is provided a compound as defined in the second aspect of the invention for use in medicine (which may also be referred to as use as a pharmaceutical).

For the avoidance of doubt, all references to the second aspect of the invention include references to the alternative second aspect of the invention.

Thus, in the third aspect of the invention there is provided a compound of formula Ia as defined in the second aspect of the invention, or a pharmaceutically acceptable salt thereof, for use in medicine (which may also be referred to as use as a pharmaceutical).

Similarly, in the third aspect of the invention there is provided a compound of formula Ib as defined in the second aspect of the invention, or a pharmaceutically acceptable salt thereof, for use in medicine (which may also be referred to as use as a pharmaceutical).

Pharmaceutical Compositions

As described herein, compounds of the first and, therefore, second aspects of the invention are useful as pharmaceuticals. Such compounds may be administered alone or may be administered by way of known pharmaceutical compositions/formulations.

In a fourth aspect of the invention, there is provided a pharmaceutical composition comprising a compound as defined in the second aspect of the invention, and optionally one or more pharmaceutically acceptable adjuvant, diluent and/or carrier.

The skilled person will understand that references herein to compounds of the first aspect of the invention being for particular uses (and, similarly, to uses and methods of use relating to compounds of the invention) may also apply to pharmaceutical compositions comprising compounds of the invention as described herein.

In a fifth aspect of the invention, there is provided a pharmaceutical composition comprising a compound as defined in the first aspect of the invention, and optionally one or more pharmaceutically acceptable adjuvant, diluent and/or carrier, for use in the treatment of cancer and/or the treatment or prevention of a viral infection (as defined in the first aspect of the invention).

The skilled person will understand that compounds of the first (and, therefore, second) aspect of the invention may act systemically and/or locally (i.e. at a particular site).

The skilled person will understand that compounds and compositions as described in the first to fifth aspects of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form. Pharmaceutical compositions as described herein will include compositions in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration.

Thus, in particular embodiments of the fourth and fifth aspects of the invention, the pharmaceutical formulation is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

For example, in the preparation of pharmaceutical formulations for oral administration, the compound may be mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or compressed into tablets.

Soft gelatine capsules may be prepared with capsules containing one or more active compounds (e.g. compounds of the first and, therefore, second aspects of the invention, and optionally additional therapeutic agents), together with, for example, vegetable oil, fat, or other suitable vehicle for soft gelatine capsules. Similarly, hard gelatine capsules may contain such compound(s) in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the compound(s) mixed with a neutral fat base; (ii) in the form of a gelatine rectal capsule which contains the active substance in a mixture with a vegetable oil, paraffin oil, or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the compound(s) and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound(s) in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

In particular embodiments of the fourth and fifth aspects of the invention, the pharmaceutical composition does not comprise liposomes.

The skilled person will understand that compounds of the first (and, therefore, second) aspect of the invention may be administered (for example, as compositions as described in the fourth and fifth aspects of the invention) at varying doses, with suitable doses being readily determined by one of skill in the art. Oral, pulmonary and topical dosages (and subcutaneous dosages, although these dosages may be relatively lower) may range from between about 0.01 mg/kg of body weight per day (mg/kg/day) to about 200 mg/kg/day, preferably about 0.01 to about 10 mg/kg/day, and more preferably about 0.1 to about 5.0 mg/kg/day. For example, when administered orally, treatment with such compounds and compositions may comprise administration of a compositions typically containing between about 0.01 mg to about 2000 mg, for example between about 0.1 mg to about 500 mg, or between 1 mg to about 100 mg, of the active ingredient. When admixture intravenously, the most preferred doses will range from about 0.001 to about 10 mg/kg/hour during constant rate infusion. Advantageously, treatment may comprise administration of such compounds and compositions in a single daily dose, or the total daily dosage may be administered in divided doses of two, three or four times daily (with reference to the doses described herein).

In any event, the skilled person (e.g. the physician) will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

As described herein above, the skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of cancer, such as treatment with one or more other therapeutic agent that is useful in the treatment of cancer, or other means for the treatment or prevention of a viral infection.

In particular embodiments of the fourth and fifth aspects of the invention, the pharmaceutical composition may further comprise one or more additional (i.e. other) therapeutic agent.

In more particular embodiments, the one or more additional therapeutic agent is an agent for the treatment of cancer (such as an additional agent for the treatment of a cancer as described herein, e.g. malignant melanoma).

In other embodiments, the one or more additional therapeutic agent is an agent for the treatment or prevention of a viral infection (e.g. a viral infection as described herein).

The skilled person will understand that combinations of therapeutic agents may also described as a combination product and/or provided as a kit-of-parts.

In a sixth aspect of the invention, there is provided a combination product comprising:
(A) a compound as defined in the first aspect of the invention; and
(B) one or more additional therapeutic agent,
wherein each of components (A) and (B) is formulated in admixture, optionally with one or more a pharmaceutically-acceptable adjuvant, diluent or carrier.

In a seventh aspect of the invention, there is provided a kit-of-parts comprising:
(a) a compound as defined in the first (or second) aspect of the invention, or a pharmaceutical composition as defined in the fourth or fifth aspect of the invention; and
(b) one or more other therapeutic agent, optionally in admixture with one or more pharmaceutically-acceptable adjuvant, diluent or carrier,
which components (a) and (b) are each provided in a form that is suitable for administration in conjunction with the other.

In particular embodiments of the fourth to fifth aspects of the invention, the additional therapeutic agent is a therapeutic agent for the treatment of cancer (such as an additional agent for the treatment of a cancer as described herein, e.g. malignant melanoma).

In particular embodiments of the fourth to fifth aspects of the invention, the additional therapeutic agent is an agent for the treatment of malignant melanoma.

In particular embodiments of the fourth to fifth aspects of the invention, the additional therapeutic agent is an agent that is:
(i) capable of reducing levels of nucleosides and/or nucleotides within a cell (e.g. a cancerous cell, such as a cell forming part of a cancer as described herein); and/or
(ii) an activator of p53 (such as an inhibitor of MDM2).

For the avoidance of doubt, compounds (i.e. therapeutic agents) that are
(i) capable of reducing levels of nucleosides and/or nucleotides within a cell (e.g. a cancerous cell, such as a cell forming part of a cancer as described herein); and/or
(ii) an activators of p53 (such as an inhibitor of MDM2),
will be readily identified by those skilled in the art and include, in particular, such therapeutic agents that are commercially available (e.g. agents that the subject of a marketing authorization in one or more territory, such as a European or US marketing authorization).

The skilled person will understand that references to therapeutic agents capable of reducing levels of nucleosides and/or nucleotides within a cell (e.g. a cancerous cell, such as a cell forming part of a cancer as described herein) may refer to compounds capable of reducing levels of such nucleosides and/or nucleotides (such as the levels of uridine and/or uridine phosphates, e.g. mono-, di- and tri-phosphates) within such a cell by at least 10% (such as at least 20%, at least 30% or at least 40%, for example at least 50%, at least 60%, at least 70% or at least 80%, e.g. at least 90%) when compared to the levels of such nucleosides and/or nucleotides in such a cell prior to treatment with the relevant compound.

The skilled person will further understand that references to therapeutic agents capable of reducing levels of nucleosides and/or nucleotides within a cell (e.g. a cancerous cell, such as a cell forming part of a cancer as described herein) may include references to compounds that act by inhibiting uptake of such nucleosides and/or nucleotides by such cells. For example, such therapeutic agents may include inhibitors of uridine uptake, as known to those skilled in the art (such as the therapeutic agent nilotinib or dipyridamole).

Particular therapeutic agents capable of reducing levels of nucleosides and/or nucleotides within a cell include nilotinib, dipyridamole, imatinib, gefitinib, ibrutinib, varlitinib, volitinib and vemurafenib (e.g. nilotinib and imatinib).

For example, therapeutic agents capable of reducing levels of nucleosides and/or nucleotides within a cell include nilotinib, dipyridamole, imatinib, ibrutinib and vemurafenib.

More particular therapeutic agents capable of reducing levels of nucleosides and/or nucleotides within a cell include nilotinib, ibrutinib and dipyridamole.

Yet more particular therapeutic agents capable of reducing levels of nucleosides and/or nucleotides within a cell include imatinib.

Yet more particular therapeutic agents capable of reducing levels of nucleosides and/or nucleotides within a cell include vemurafenib.

For example, therapeutic agents capable of reducing levels of nucleosides and/or nucleotides within a cell include ASLAN001 (varlitinib), ibrutinib, rapamycin, vemurafenib, gefitinib, antimycin A, BI-2536, VX-680, roscovitine, olomoucine, imatinib (STI-571), AG1879, AG1517, AG1478, AG825, AG18, AG490, vinblastine, etoposide, genistein, U0126, Raf-1 inhibitor 1, H89, KN93, staurosporine, ZM336372 and indirubin-3'-monoxime.

In particular, therapeutic agents capable of reducing levels of nucleosides and/or nucleotides within a cell include ASLAN001 (varlitinib).

In particular, therapeutic agents capable of reducing levels of nucleosides and/or nucleotides within a cell include ibrutinib.

Other compounds that could reduce the levels of nucleosides and/or nucleotides in cells include BIBW2992, AG013736, PF-02341066/PF-2341066, BMS-354825, 5-aza-2'-deoxycytidine, LY317615, CP-358774/OSI-774, RAD001/SDZ-RAD/Certican, GW572016/GW2016, AMN-107, GW786034/Armala, AP24534, BAY73-4506, INCB018424, Bay 43-9006/Nexaxar, Sutent/SU-11248, Torisel/CCI-779, tasocitinib/CP-690550, GSK1120212, ZD6474, PLX4032/RG7204/RO5185426, SAHA/Zolinza/ MK-0683, AT-877/HA-1077 and quizartinib.

The skilled person will understand that references to activators of p53 may refer to therapeutic agents that are capable of: increasing p53 synthesis and/or stability (e.g. by increasing thermo stability or through inhibition of degradation); and/or increasing transcription factor function, within a cell (e.g. a cancerous cell, such as a cell forming part of a cancer as described herein).

In particular, it may refer to increasing p53 synthesis and/or stability such that the levels of p53 within a cell (e.g. a cancerous cell, such as a cell forming part of a cancer as described herein) are increased by at least by at least 10% (such as at least 20%, at least 30% or at least 40%, for example at least 50%, at least 60%, at least 70% or at least 80%, e.g. at least 90% or at least 100%), when compared to the levels of p53 in such a cell prior to treatment with the relevant compound. Further, it may refer to increasing the transcription factor function of p53 in a cell (e.g. a cancerous cell, such as a cell forming part of a cancer as described herein) by at least 10% (such as at least 20%, at least 30% or at least 40%, for example at least 50%, at least 60%, at least 70% or at least 80%, e.g. at least 90% or at least 100%), when compared to the levels of p53 in such a cell prior to treatment with the relevant compound.

The skilled person will further understand that references to activators of p53 may include references to therapeutic agents that act by inhibiting MDM2 (such as the therapeutic agent nutlin-3).

The skilled person will understand that references to therapeutic agents that act by inhibiting MDM2 may refer to compounds capable of inhibiting the activity of MDM2 within a cell (e.g. a cancerous cell, such as a cell forming part of a cancer as described herein) by at least 10% (such as at least 20%, at least 30% or at least 40%, for example at least 50%, at least 60%, at least 70% or at least 80%, e.g. at least 90%) when compared to the levels of such activity in such a cell prior to treatment with the relevant compound.

Particular therapeutic agents capable of activating p53 (e.g. by inhibiting MDM2) include nutlin-3, RO5045337, idasanutlin, AMG-232, DS3032b, serdemetan, ALRN-6924, SAR-405838, CGM-097, RO-5503781, RO-6839921 and HDM-201.

More particular therapeutic agents capable of activating p53 (e.g. by inhibiting MDM2) include nutlin-3

Further therapeutic agents capable of activating p53 (e.g. by increasing p53 levels) include PS-341/MS-341, Ara-C, adriamycin, 5-FU, Camptosar and mithramycin A.

In alternative embodiments of the fourth to fifth aspects of the invention, the additional therapeutic agent is a therapeutic agent for the treatment or prevention of a viral infection, such as a viral infection as described herein.

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable adjuvant, diluent or carrier.

In further aspects of the invention, there is provided a process for the preparation of a combination product or kit-of-parts as hereinbefore defined, which process comprises bringing into association a compound of the invention, as hereinbefore defined, or a pharmaceutically acceptable salt thereof with the other therapeutic agent that is useful in the treatment of cancer and/or the treatment or prevention of a viral infection, and at least one pharmaceutically-acceptable adjuvant, diluent or carrier.

As used herein, references to bringing into association will mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds as defined in the first and second aspects of the invention may be prepared in accordance with techniques that are well known to those skilled in the art, such as those described in the examples provided hereinafter.

In an eight aspect of the invention, there is provided a process for the preparation of a compound of formula Ia, or a pharmaceutically acceptable salt thereof, as defined in the second aspect of the invention, which process comprises:
(i) reaction of a compound of formula II

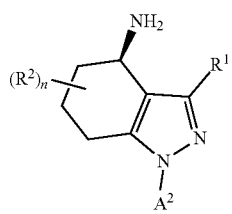

(II)

wherein $R^1$, $R^2$, $A^2$ and n are as defined in the second aspect of the invention, with a compound of formula III $$LG_1\text{-}L^1\text{-}A^1 \quad (III)$$

wherein $A^1$ represents aryl optionally substituted by one or more groups independently selected from $G^1$ or heteroaryl optionally by one or more groups independently selected from $G^2$, $L^1$ represents —C(O)—, —C(O)N($R^3$)—, —C(O)O—, —S(O)$_j$—, or —S(O)$_k$N($R^4$)—, and $LG_1$ represents a suitable leaving group, in the presence of a suitable solvent and optionally in the presence of a suitable base and/or a suitable catalyst, under conditions known to those skilled in the art (for example, where LG, represents —OH, the reaction may be performed in the presence of reagents suitable for performing peptide coupling reactions as known to those skilled in the art, such as in the presence of HOBt and EDC.HCl, or alternatively HATU or HBTU, and optionally in the presence of a suitable base, e.g. Et$_3$N);
(ii) where $L^1$ represents —C(O)N($R^3$)— wherein $R^3$ represents H, reaction of a compound of formula II with a compound of formula IV $$Ar^1\text{—}N\text{=}C\text{=}O \quad (IV)$$

wherein $A^1$ is as defined in the second aspect of the invention in the presence of a suitable solvent and optionally in the presence of a suitable base and/or a suitable catalyst, under conditions known to those skilled in the art; or
(iii) reaction of a compound of formula (V)

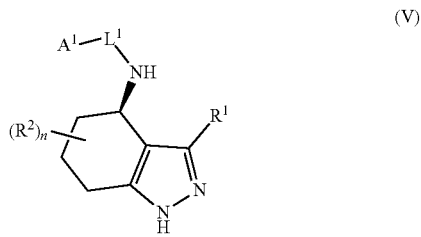

(V)

wherein $R^1$, $R^2$, $A^1$, $L^1$ and n are as defined in the second aspect of the invention, with a compound of formula VI $$LG_2\text{-}A^2 \quad (VI)$$

wherein $A^2$ represents aryl optionally substituted by one or more groups independently selected from $G^3$ or heteroaryl optionally substituted by one or more groups independently selected from $G^4$, and $LG_2$ represents a suitable leaving group, in the presence of a suitable solvent and optionally in the presence of a suitable base and/or a suitable catalyst, under conditions known to those skilled in the art (for example, under Buchwald-Hartwig conditions as known to those skilled in the art, e.g. where $LG_2$ represents a suitable leaving group such as halo and in the presence of a suitable catalyst such as a suitable Pd catalyst (e.g. Pd$_2$(dba)$_3$) and a suitable base, or under Chan-Lam conditions as known to those skilled in the art, e.g. where $LG_2$ represents a suitable leaving group such as —B(OH)$_2$ and in the presence of a suitable catalyst such as a suitable Cu catalyst (e.g. Cu (OAc)$_2$) and a suitable base).

Compounds of formulae II, III, IV, V and VI are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter ala "*Comprehensive Organic Synthesis*" by B. M. Trost and I. Fleming, Pergamon Press, 1991. Further references that may be employed include "*Heterocyclic Chemistry*" by J. A.

Joule, K. Mills and G. F. Smith, 3rd edition, published by Chapman & Hall, "Comprehensive Heterocyclic Chemistry II" by A. R. Katritzky, C. W. Rees and E. F. V. Scriven, Pergamon Press, 1996 and "Science of Synthesis", Volumes 9-17 (Hetarenes and Related Ring Systems), Georg Thieme Verlag, 2006.

For example, compounds of formula II where n represents 0 to 6 may be prepared by reaction of a compound of formula VII

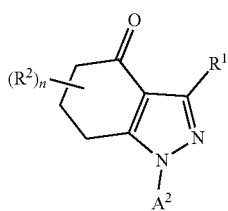

(VII)

wherein $R^1$, $R^2$ and $A^2$ are as defined herein for compounds of formula I (and formula Ia) and n represents 0 to 6, with a suitable chiral amide (such as $(S_S)$-2-methyl-2-propanesulfinamide) under conditions known to those skilled in the art (for example, in the presence of a suitable catalyst (such as $Ti(OEt)_4$) and a suitable reducing agent (such as L-selectride), and in the presence of a suitable solvent), followed by cleavage of the amide, under conditions known to those skilled in the art (i.e. to provide the free amine of the compound of formula II).

Further, compounds of formula VII may be prepared by reaction of a compound of formula VIII

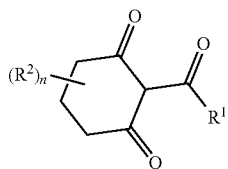

(VIII)

wherein $R^1$, $R^2$ and n are as defined herein for compounds of formula VII, with a compound of formula IX

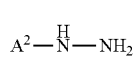

(IX)

wherein $A^2$ is as defined herein for compounds of formula I (and formula Ia), under conditions known to those skilled in the art.

Alternatively, compounds of formula VII wherein $R^1$ represents H may be prepared by reaction of a compound of formula X

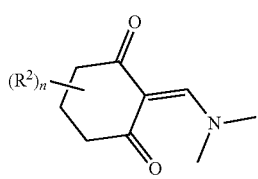

(X)

wherein $R^2$ and n are as defined herein for compounds of formula VII, with a compound of formula IX as defined herein, under conditions known to those skilled in the art.

The skilled person will understand that compounds of formula Ill may be commercially available, known in the literature, or may be prepared by analogy with the synthesis of a compound of formula I but wherein $A^2$ represents H or a suitable protecting group as known to those skilled in the art, wherein the latter case the preparation will require removal of the protecting group, under conditions known to those skilled in the art, to yield the compound of formula Ill.

Compounds of formulae VII, VIII, IX and X are either commercially available, are known in the literature, or may be obtained either by analogy with the processes described herein, or by conventional synthetic procedures, in accordance with standard techniques, from available starting materials using appropriate reagents and reaction conditions.

The skilled person will understand that compounds of formula I, and pharmaceutically acceptable salts thereof, as defined herein may be prepared by analogy with the synthesis of compounds of formula Ia, and pharmaceutically acceptable salts thereof, as described in the eighth aspect of the invention. In particular, such processes may be performed in accordance with the eight aspect of the invention but wherein the stereochemistry indicated for compounds of formula II and V is not defined (e.g. a mixture, such as a racemic mixture, of the corresponding enantiomers is used).

Similarly, compounds of formula Ib, and pharmaceutically acceptable salts thereof, as defined herein may be prepared by analogy with the synthesis of compounds of formula Ia, and pharmaceutically acceptable salts thereof, as described in the eighth aspect of the invention. In particular, such processes may be performed in accordance with the eight aspect of the invention but wherein the stereochemistry indicated for compounds of formula II and V is reversed (i.e. the opposite enantiomer is used).

Further, compounds used in the synthesis of compounds of formula Ib, and pharmaceutically acceptable salts thereof, may be commercially available, known in the literature or prepared by analogy with the preparation of compounds used in the preparation of compounds of Ia, and pharmaceutically acceptable salts thereof.

For example, compounds of formula II where n represents 0 to 6, but wherein the stereochemistry shown is reversed (i.e. the opposite enantiomer is provided) may be prepared by reaction of a compound of formula VII, as defined herein, with a suitable chiral amide (such as $(S_S)$-2-methyl-2-propanesulfinamide) under conditions known to those skilled in the art (for example, in the presence of a suitable catalyst (such as $Ti(OEt)_4$) and a suitable reducing agent (such as $NaBH_4$), and in the presence of a suitable solvent), followed by cleavage of the amide, under conditions known to those skilled in the art (i.e. to provide the free amine of the compound corresponding to the compound of formula II).

The substituents on $A^1$, $A^2$, $L^1$, $R^1$ and $R^2$ groups, as hereinbefore defined, may be modified one or more times, after or during the processes described above for preparation of compounds of formula Ia (and, similarly, compounds of formula Ib) by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "Comprehensive Organic Functional Group Transformations" by A.

R. Katritzky, O. Meth-Cohn and C. W. Rees, Pergamon Press, 1995 and/or "*Comprehensive Organic Transformations*" by R. C. Larock, Wiley-VCH, 1999.

Such compounds may be isolated from their reaction mixtures and, if necessary, purified using conventional techniques as known to those skilled in the art. Thus, processes for preparation of compounds of the invention as described herein may include, as a final step, isolation and optionally purification of the compound of the invention (e.g. isolation and optionally purification of the compound of formula I).

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999).

Compounds as described herein (in particular, compounds as defined in the first and, therefore, second aspects of the invention) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, such compounds may have the advantage that they are more efficacious and/or exhibit advantageous properties in vivo.

Without wishing to be bound by theory, compounds as described herein are thought to be potent inhibitors of DHODH, which leads to activity as inhibitors of de novo pyrimidine nucleotide synthesis. Cancer cells are known to have greater susceptibility to nucleotide level modulation, due to their defective cell cycle check points. This allows for potent and selective inhibition of cancer cell growth and promotion of cancer cell death. Further, combining compounds as described herein with therapeutic agents that are able to decrease the level of nucleotides and nucleosides, such as pyrimidine nucleotides and nucleosides, in the cell (for example, by inhibiting uptake or preventing retention within the cell; such as the therapeutic agent nilotinib) are thought to provide an effective and synergistic combination therapy.

Surprisingly, despite their activity in reducing levels of nucleotides and nucleosides in such cells, it has also been found that compounds described herein are able to increase the synthesis of p53, which is a known tumour suppressor. Further, it has been found that combining compounds described herein with other activators of p53 (such as inhibitors of MDM2, e.g. nutlin-3) also provides an effective and synergistic combination therapy.

Again without wishing to be bound by theory, it is thought that the observed synergy between the DHODH inhibitors described herein and inhibitors of p53 degradation, such as nutlin-3, results from the DHODH inhibitors ability to increase p53 synthesis. This increase in p53 synthesis together with the inhibition of p53 degradation by nutlin-3 (an MDM2 inhibitor) leads to a stronger increase in p53 levels, which serves to induce p53 pro-apoptotic functions.

Further, compounds described herein are thought to be potent inhibitors of viral replication, which renders them of particular use in the treatment or prevention of viral infections.

EXAMPLES

Figure 1:
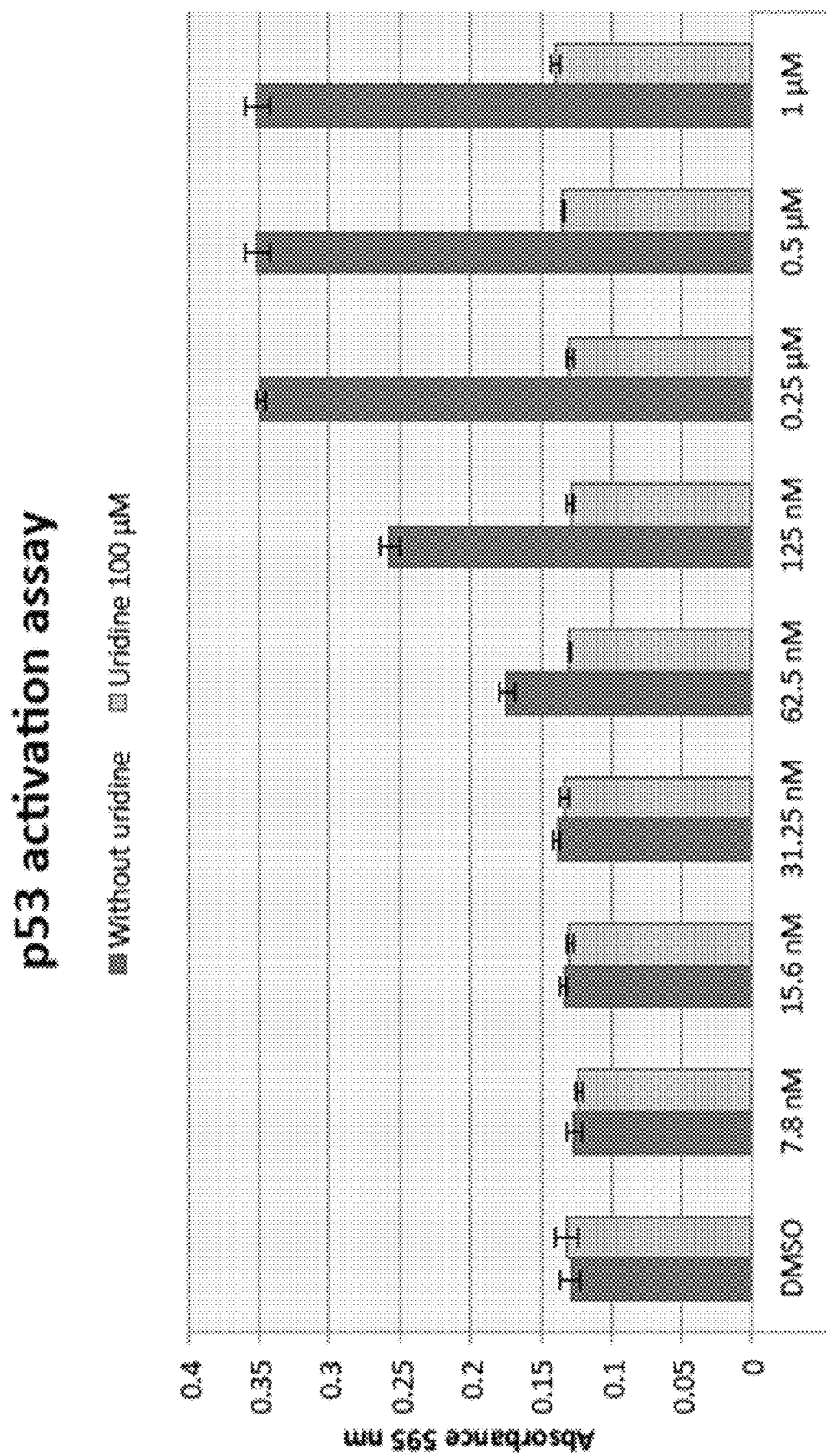
FIG. 1 shows results obtained from Biological Example 2, which measures the effect of different concentrations of Example 8 on the activation of the transcription factor function of p53 in the absence and presence of excess uridine.

Chemicals and reagents were obtained from commercial suppliers and were used as received unless otherwise stated. All reactions involving moisture sensitive reagents were performed in oven or flame dried glassware under a positive pressure of nitrogen. Tetrahydrofuran (THF) and dichloromethane (DCM) were obtained dry from a solvent purification system (MBraun, SPS-800).

Thin-layer chromatography was performed using glass plates coated with silica gel (with fluorescent indicator $UV_{254}$). Developed plates were air-dried and analysed under a UV lamp or by $KMnO_4$ dip staining. Flash column chromatography was performed using silica gel (40-63 µm).

Melting points were recorded in open capillaries using an Electrothermal 9100 melting point apparatus. Values are quoted to the nearest 1° C. and are uncorrected.

Infrared spectra were recorded on a Perkin Elmer Spectrum GX FT-IR spectrometer using KBr discs (KBr) as stated. Absorption maxima are reported as wavenumbers (cm$^{-1}$).

Low resolution (LR) and high resolution (HR) electrospray mass spectral (ES-MS) analyses were acquired by electrospray ionisation (ESI), electron impact (EI) or chemical ionisation (CI). These were acquired by the EPSRC National Mass Spectrometry Service or within the School of Chemistry, University of St Andrews.

Nuclear magnetic resonance (NMR) spectra were acquired on either a Bruker Avance 300 ($^1$H, 300.1 MHz; $^{13}$C, 75.5 MHz), Bruker Avance II 400 ($^1$H, 400.1 MHz; $^{13}$C, 100.6 MHz), Bruker Avance 500 ($^1$H, 499.9 MHz; $^{13}$C, 125.7 MHz), Bruker Avance III 500 ($^1$H, 500.1 MHz, $^{13}$C, 125.7 MHz), Varian Mercury plus, Bruker Ascend 400 or a Bruker DPX400 spectrometer and in the deuterated solvent stated. All NMR spectra were acquired using the deuterated solvent as the lock. Coupling constants (J) are quoted in Hz and are recorded to the nearest 0.1 Hz. The following abbreviations are used; s, singlet; d, doublet; dd, doublet of doublets; t, triplet; m, multiplet; q, quartet; and br, broad. Assignments of signals are proposed based on the values observed.

HPLC analyses were obtained on a Gilson HPLC consisting of a Gilson 305 pump, Gilson 306 pump, Gilson 811C dynamic mixer, Gilson 805 manometric module, Gilson 401C dilutor, Gilson 213XL sample injector and sample detection was performed with a Gilson 118 UV/vis detector. Separation was achieved using a Chiralpak AD-H column. Optical rotations were measured on a Perkin Elmer Precisely/Model-341 polarimeter operating at the sodium D line with a 100 mm path cell.

Automated flash chromatography was performed on Biotage Isolera or Grace Reveleris X2 using Grace Reveleris Silica columns.

Analytical RPLC-MS was performed using a HPLC-MS Dionex Ultimate 3000 with a Bruker amaZon SL, under the following conditions: Column, Kinetex C18 (2.6 µm, 50×3.0 mm); Mobile phases, MeCN/water gradients (0.05% HCOOH); Flowrate, 1.5 mL/min; Detection, UV (214, 254, 280 nm) and MS (ESI, pos, neg or alternate polarity) or Agilent/HP 1200 system 6110 mass spectrometer with electrospray ionization (ESI+). HPLC-MS methods were the following: Method 1—Waters XBridge C18 3.5 µm column (3.0 mm×50 mm), 3.5 min gradient mobile phase [CH$_3$CN]/[10 mM NH$_4$HCO$_3$/H$_2$O]; Method 2—ACE C18 3.5 µm column (3.0 mm×50 mm), mobile phase [0.1% TFA/CH$_3$CN]/[0.1% TFA/H$_2$O] or Water micro mass ZQ 2000 using positive and negative electrospray ionization.

Preparative RP-LC was performed using a Gilson system equipped with a Zorbax SB-C8 (5 µm, 21.2×150 mm) column, using MeCN/H$_2$O (0.05% HCOOH) gradients at a flow rate of 15 mL/min with UV (214 or 254 nm) detection or VP 250/21 NUCLEODUR C-18, HTEC, 5 µm column on a GILSON 333/334 Prep-Scale system with a flow rate of 20 mL/min, detection at 254 nm, and an CH$_3$CN/H$_2$O eluent system. Chiral Separations were performed using a SFC Waters Investigator system with Waters 2998 PDA detector. The column temperature was set to 45° C.

Example Compounds

The invention is illustrated by way of the following example compounds.

In the event that there is a discrepancy between nomenclature and the structure of compounds as depicted graphically, it is the latter that presides (unless contradicted by any experimental details that may be given and/or unless it is clear from the context).

The following compounds were prepared in the manner described below.

Example 1: N-(1-(2-Fluorophenyl)-4,5,6,7-tetrahydro-1H-indazol-4-yl)picolinamide

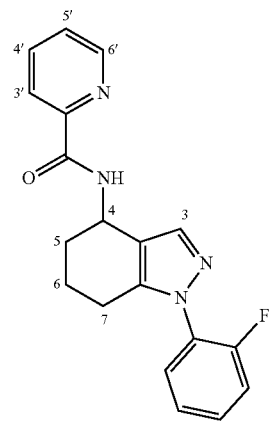 [SMILES: O=C(NC1CCCc2c1cnn2-c1ccccc1F)c1ccccn1]

A solution of 1-(2-fluorophenyl)-6,7-dihydro-1H-indazol-4(5H)-one (S2) (1.0 g, 4.3 mmol, 1.0 eq.) in 2-propanol (80 mL) was treated, under vigorous stirring, with ammonium acetate (3.3 g, 43.4 mmol, 10.0 eq.). After complete dissolution, molecular sieves (4 Å, 1.5 g) and NaBH$_3$CN (1.3 g, 21.7 mmol, 5.0 eq.) were added and the reaction mixture was stirred for 12 h at 70° C. The solution was concentrated in vacuo; the residue was diluted with EtOAc (200 mL) and washed thoroughly with a 2 M aq. solution of NaOH (20 mL) and brine (20 mL), dried over MgSO$_4$, filtered and concentrated. Without further purification, the crude compound (S2) was directly used in the next step. To a solution of 2-picolinic acid (0.48 g, 3.9 mmol, 2.0 eq.), HOBt (0.79 g, 5.8 mmol, 1.5 eq.), EDC.HCl (1.12 g, 5.8 mmol, 1.5 eq.) and Et$_3$N (0.21 mL, 5.8 mmol, 1.5 eq.) in DCM (80 mL) were added 1-(2-fluorophenyl)-4,5,6,7-tetrahydro-1H-indazol-4-amine (0.90 g, 3.9 mmol, 1.0 eq.) and DMAP (48 mg, 0.39 mmol, 0.1 eq.). The resulting solution was stirred at r.t. overnight. The solution was concentrated in vacuo; the residue was diluted with EtOAc (40 mL) and washed thoroughly with a sat. aq. NaHCO$_3$ solution (20 mL) and brine (20 mL), dried over MgSO$_4$, filtered and concentrated. Purified via the Biotage SP4 (silica-packed SNAP column 10 g; 20-50% EtOAc/hexanes) to give Example 1 as a white solid (0.92 g, 65% over 2 steps).

Analysis of the product found: mp 96-98° C.; IR (KBr) $v_{max}$: 3288 (NH), 2945, 1661 (C=O), 1516; $^1$H NMR (500 MHz, CDCl$_3$) δ 8.53 (ddd, J=4.8, 1.7, 0.9 Hz, 1H, C6'-H̲), 8.34-8.15 (m, 2H, NH̲, C3'-H̲), 7.87 (td, J=7.7, 1.7 Hz, 1H, C4'-H̲), 7.69 (s, 1H, C3-H̲), 7.57-7.35 (m, 3H, 2×ArH̲, C5'-H̲), 7.34-7.15 (m, 2H, 2×ArH̲), 5.35 (dt, J=8.3, 5.6 Hz, 1H, C4-H̲), 2.73-2.48 (m, 2H, C7-H̲$_2$), 2.27-2.09 (m, 1H, C5-H̲), 2.03-1.85 (m, 3H, C5-H̲, C6-H̲$_2$); $^{13}$C NMR (126 MHz, CDCl$_3$) δ 163.9 (CO), 156.5 (d, J=251.5 Hz, C), 150.1 (C2'), 148.2 (C6'), 141.9 (C7a), 139.5 (C3), 137.5 (C4'), 130.1 (d, J=7.8 Hz, CH), 128.8 (CH), 127.5 (d, J=11.7 Hz, C), 126.3

(C5'), 124.9 (d, J=3.7 Hz, CH), 122.4 (C3'), 118.1 (C3a), 116.8 (d, J=20.0 Hz, CH), 42.5 (C4), 30.3 (C5), 21.7 (C7), 20.3 (C6); m/z (ES⁺) 358.86 ([M+Na]⁺, 100%); HRMS (ES⁺) Calcd for $C_{19}H_{17}N_4OFNa$ [M+Na]⁺: 359.1284, found 359.1283.

Example 2: (S)—N-(1-(2-Fluorophenyl)-4,5,6,7-tetrahydro-1H-indazol-4-yl)picolinamide

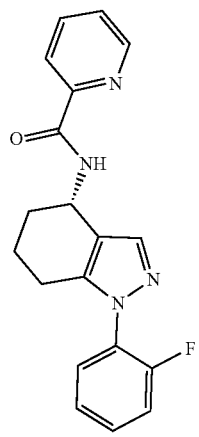 [SMILES: O=C(N[C@H]1CCCc2c1cnn2-c1ccccc1F)c1ccccn1]

Concentrated HCl (0.4 mL) was added dropwise to a solution of (S)—N—((S)-1-(2-fluorophenyl)-4,5,6,7-tetrahydro-1H-indazol-4-yl)-2-methylpropane-2-sulfinamide (S3) (136 mg, 0.41 mmol, 1.0 eq.) in methanol (5 mL), and the solution was stirred at room temperature for 4 h. The reaction was quenched with a sat. aq. NaHCO₃ solution (5 mL), and diluted with DCM (5 mL) and water (5 mL). The organic layer was washed with a sat. aq. NaHCO₃ solution (5 mL) and brine (5 mL), dried over MgSO₄, filtered and concentrated in vacuo to give the crude free amine, analysis of which found: ¹H NMR (400 MHz, CDCl₃) δ 7.71 (s, 1H, C3-H), 7.50-7.34 (m, 2H, 2×ArH), 7.28-7.17 (m, 2H, 2×Ar H), 4.05-4.00 (m, 1H, C4-H), 2.63-2.41 (m, 2H, C7-H₂), 2.13-1.48 (m, 4H, C5-H₂, C6-H₂); ¹³C NMR (101 MHz, CDCl₃) δ 157.5 (C), 155.0 (C), 140.6 (C7a), 138.2 (C3), 129.8 (d, J=7.7 Hz, CH), 128.6 (CH), 124.6 (d, J=3.8 Hz, CH), 121.9 (C3a), 116.6 (d, J=20.3 Hz, CH), 44.6 (C4), 34.1 (C5), 21.6 (C7), 20.2 (C6); m/z (ES⁺) 232.11 ([M+H]⁺, 100%). Without further purification, the crude amine was used directly in the next step. To a solution of 2-picolinic acid (100 mg, 0.81 mmol, 2.0 eq.), HOBt (83 mg, 0.62 mmol, 1.5 eq.), EDC.HCl (119 mg, 0.62 mmol, 1.5 eq.) and Et₃N (0.17 mL, 1.23 mmol, 3.0 eq.) in DCM (7 mL) were added (S5) (109 mg, 0.41 mmol, 1.0 eq.) and DMAP (5 mg, 0.04 mmol, 0.1 eq.). The resulting solution was stirred at r.t. overnight. The solution was concentrated in vacuo. The residue was diluted with EtOAc (10 mL) and washed thoroughly with a sat. aq. NaHCO₃ solution (5 mL) and brine (5 mL), dried over MgSO₄, filtered and concentrated in vacuo. Purified via the Biotage SP4 (silica-packed SNAP column 10 g; 20-50% EtOAc/hexanes) to give Example 2 as a white solid (110 g, 80% over 2 steps).

Analysis of the product found: mp 116-118° C.; $[\alpha]_D^{20}$= −71.8 (c 0.1, CHCl₃); Chiral HPLC analysis Chiralpak AD-H (5% IPA/hexane, 1 mL min⁻¹, 254 nm, 30° C.) $t_R$ (major) 35.5, $t_R$(minor) 31.5, >99% ee; IR (KBr) $v_{max}$: 3443 (NH), 3288, 2922, 1658 (C=O), 1530; ¹H NMR (500 MHz, CDCl₃) δ 8.53 (ddd, J=4.8, 1.7, 1.1 Hz, 1H, C6'-H), 8.26 (dt, J=7.7, 1.1 Hz, 1H, C3'-H), 8.24-8.22 (m, 1H, NH), 7.87 (td, J=7.7, 1.7 Hz, 1H, C4'-H), 7.69 (s, 1H, C3-H), 7.48 (s, 1H, C3-H), 7.48 (s, 1H, C3-H), 7.46-7.36 (m, 2H, ArH, C5'-H), 7.31-7.18 (m, 2H, 2×ArH), 5.41-5.25 (m, 1H, C4-H), 2.68-2.43 (m, 2H, C7-H₂), 2.25-2.06 (m, 1H, C5-H), 2.02-1.83 (m, 3H, C5-H, C6-H₂); ¹³C NMR (126 MHz, CDCl₃) δ 163.8 (CO), 156.4 (d, J=251.6 Hz, C), 150.1 (C2'), 148.2 (C6'), 141.9 (C7a), 139.5 (C3), 137.5 (C4'), 130.1 (d, J=7.8 Hz, CH), 128.7 (CH), 127.5 (d, J=11.8 Hz, C), 126.3 (C5'), 124.9 (d, J=3.8 Hz, CH), 122.4 (C3'), 118.1 (C3a), 116.8 (d, J=20.0 Hz, CH), 42.5 (C4), 30.3 (C5), 21.7 (C7), 20.3 (C6); m/z (ES⁺) 358.89 ([M+Na]⁺, 100%); HRMS (ES⁺) Calcd for $C_{19}H_{18}N_4ONa$ [M+Na]⁺: 359.1284, found 359.1276.

Example 3: (R)—N-(1-(2-fluorophenyl)-4,5,6,7-tetrahydro-1H-indazol-4-yl)picolinamide

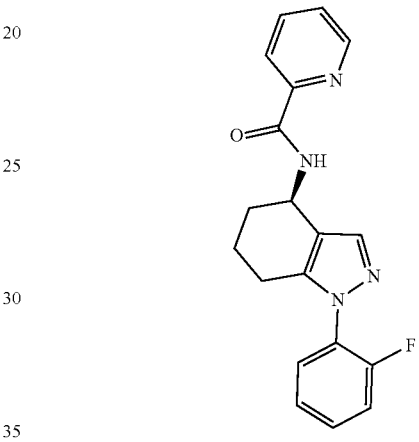

Concentrated HCl (4 mL) was added dropwise to a solution of S4 (1.4 g, 4.2 mmol) in methanol (40 mL), and the solution was stirred at room temperature for 4 hours. The reaction was quenched with a sat. aq. NaHCO₃ solution (10 mL) and diluted with DCM (20 mL) and water (20 mL). The organic layer was washed with a sat. aq. NaHCO₃ solution (20 mL) and then brine (20 mL), dried with MgSO₄, filtered and concentrated in vacuo. to give the crude free amine, analysis of which found: ¹H NMR (400 MHz, CDCl₃) δ 7.72 (s, 1H, CH), 7.53-7.32 (m, 2H, 2×ArH), 7.31-7.09 (m, 2H, 2×ArH), 4.11-4.00 (m, 1H, CH), 2.65-2.33 (m, 2H, CH₂), 2.16-1.46 (m, 4H, 2×CH₂); ¹³C NMR (101 MHz, CDCl₃) δ 157.6 (C), 155.1 (C), 140.6 (C), 138.9 (CH), 129.8 (d, J=7.8 Hz, CH), 128.6 (CH), 124.7 (d, J=3.8 Hz, CH), 122.0 (C), 116.6 (d, J=20.1 Hz, CH), 44.6 (CH), 34.1 (CH₂), 21.7 (CH₂), 20.2 (CH₂); m/z (ES⁺) 231.09 ([M+H]⁺, 100%). Without further purification, the crude amine was used directly in the next step. To a solution of 2-picolinic acid (0.91 g, 7.44 mmol, 2.0 eq.), HOBt (0.75 g, 5.58 mmol, 1.5 eq.), EDC.HCl (1.07 g, 5.58 mmol, 1.5 eq.) and Et₃N (0.78 mL, 5.58 mmol, 1.5 eq.) in DCM (75 mL) were added the crude amine (0.86 g, 3.72 mmol, 1.0 eq.) and DMAP (45 mg, 0.37 mmol, 0.1 eq.). The resulting solution was stirred at r.t. overnight. The solution was concentrated in vacuo. The residue was then diluted with EtOAc (30 mL) and washed thoroughly with a sat. aq. NaHCO₃ solution (20 mL) and brine (20 mL), dried over MgSO₄, filtered and concentrated in vacuo. The resulting solid was purified using a Biotage SP4 (silica-packed SNAP column 100 g; 20-50% EtOAc/hexanes) to give Example 3 as a white solid (1.16 g, 82% over 2 steps).

Analysis of the product found: mp 117-119° C.; $[\alpha]_D^{20}=$ +71.3 (c 0.1, CHCl$_3$); Chiral HPLC analysis Chiralpak AD-H (5% IPA/hexane, 1 mL min$^{-1}$, 254 nm, 30° C.) $t_R$ (major) 31.3, $t_R$(minor) 35.9, 98% ee; IR (KBr) $v_{max}$: 3443 (NH), 3291, 2946, 1661 (C=O), 1530; $^1$H NMR (500 MHz, CDCl$_3$) δ 8.53 (ddd, J=4.7, 1.7, 0.9 Hz, 1H, CH), 8.34-8.20 (m, 2H, NH, CH), 7.87 (td, J=7.7, 1.7 Hz, 1H, CH), 7.69 (s, 1H, CH), 7.51-7.35 (m, 3H, 2×ArH, CH), 7.32-7.11 (m, 2H, 2×ArH), 5.36 (dd, J=8.6. 4.8 Hz, 1H, CH), 2.74-2.48 (m, 2H, CH$_2$), 2.30-2.07 (m, 1H, CH), 2.07-1.74 (m, 3H, CH, CH$_2$); $^{13}$C NMR (126 MHz, CDCl$_3$) δ 163.8 (CO), 156.4 (d, J=251.5 Hz, C), 150.0 (C), 148.2 (CH), 141.9 (C), 139.5 (CH), 137.5 (CH), 130.1 (d, J=7.7 Hz, CH), 128.7 (CH), 127.5 (d, J=11.8 Hz, C), 126.3 (CH), 124.9 (d, J=3.9 Hz, CH), 122.5 (CH), 118.1 (C), 116.8 (d, J=20.1 Hz, CH), 42.5 (CH), 30.3 (CH$_2$), 21.7 (CH$_2$), 20.2 (CH$_2$); m/z (ES$^+$) 359.12 ([M+Na]$^+$, 100%); HRMS (ES$^+$) Calcd for C$_{19}$H$_{18}$N$_4$ONa [M+Na]$^+$: 359.1284, found 359.1281.

The following compounds were obtained from commercial sources.

Example 4: N-[1-(2-fluorophenyl)-4,5,6,7-tetrahydro-1H-indazol-4-yl]-1,3-thiazole-4-carboxamide

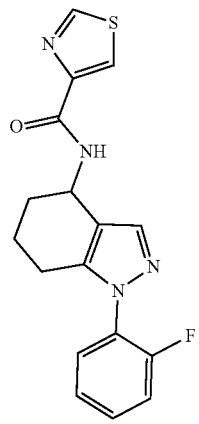 [SMILES: O=C(NC1CCCc2c1cnn2-c1ccccc1F)c1cscn1]

Example 5: N-(1-(2,4-difluorophenyl)-4,5,6,7-tetrahydro-1H-indazo-4-yl)-4,5,6,7-tetrahydrobenzo[c]isoxazole-3-carboxamide

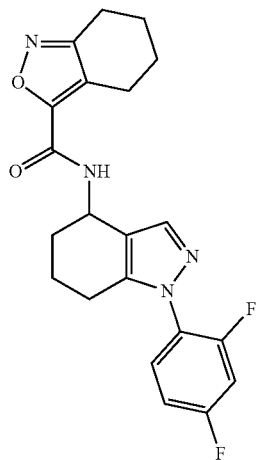 [SMILES: O=C(NC1CCCc2c1cnn2-c1ccc(F)cc1F)c1onc2c1CCCC2]

Example 6: N-[1-(3,4-dimethylphenyl)-4,5,6,7-tetrahydro-1H-indazol-4-yl]-5-methyl-3-isoxazolecarboxamide

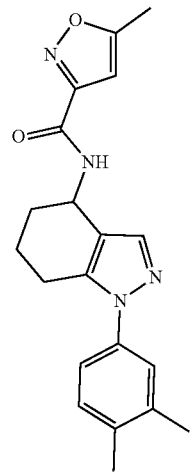 [SMILES: Cc1cc(C(=O)NC2CCCc3c2cnn3-c2ccc(C)c(C)c2)no1]

Example 7: Methyl 6-({[1-(2-fluorophenyl)-4,5,6,7-tetrahydro-1H-indazol-4-yl]amino}carbonyl)nicotinate

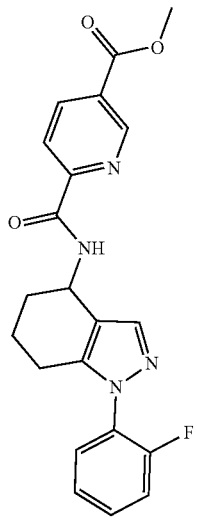 [SMILES: COC(=O)c1ccc(C(=O)NC2CCCc3c2cnn3-c2ccccc2F)nc1]

Example 8: N-(1-(2-fluorophenyl)-4,5,6,7-tetrahydro-1H-indazo-4-yl)-4,5,6,7-tetrahydrobenzo[c]isoxazole-3-carboxamide

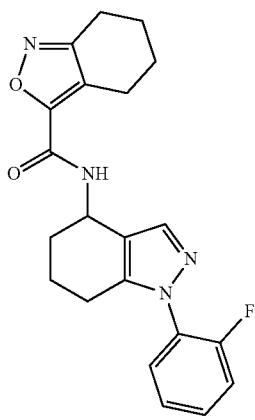 [SMILES: O=C(NC1CCCc2c1cnn2-c1ccccc1F)c1onc2c1CCCC2]

Example 9: Methyl 6-({[1-(3,5-difluorophenyl)-4,5,6,7-tetrahydro-1H-indazol-4-yl]amino}carbonyl)nicotinate

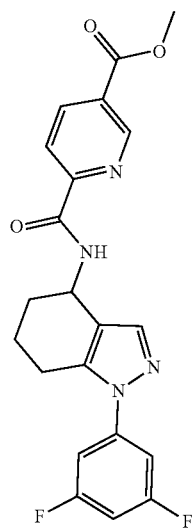 [SMILES: COC(=O)c1ccc(C(=O)NC2CCCc3c2cnn3-c2cc(F)cc(F)c2)nc1]

Example 10: N-[1-(2,4-difluorophenyl)-4,5,6,7-tetrahydro-1H-indazo-4-yl]-5-ethyl-3-isoxazolecarboxamide

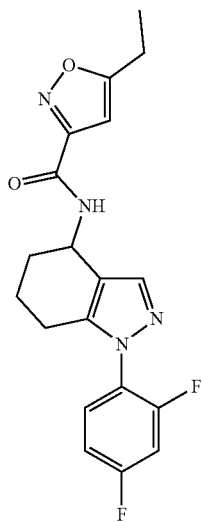 [SMILES: CCc1cc(C(=O)NC2CCCc3c2cnn3-c2ccc(F)cc2F)no1]

Example 11: N-[1-(2,4-difluorophenyl)-4,5,6,7-tetrahydro-1H-indazol-4-yl]-2-(methylthio)-1,3-thiazole-4-carboxamide

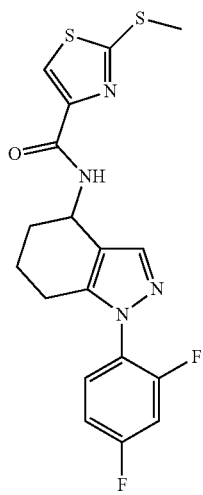 [SMILES: CSc1nc(C(=O)NC2CCCc3c2cnn3-c2ccc(F)cc2F)cs1]

The following example compounds may be prepared by analogy with the procedure described for the preparation of Example 3 and corresponding racemic compounds.

Example 12a: (R)—N-[1-(2,4-difluorophenyl)-4,5,6,7-tetrahydro-1H-indazol-4-yl]-4,5,6,7-tetrahydro-1,2-benzisoxazole-3-carboxamide

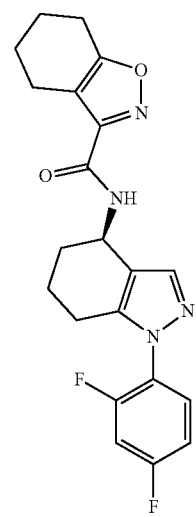 [SMILES: O=C(N[C@@H]1CCCc2c1cnn2-c1ccc(F)cc1F)c1noc2c1CCCC2]

Example 12b: N-[(4R)-1-(2,4-difluorophenyl)-4,5,6,7-tetrahydro-1H-indazol-4-yl]-4,5,6,7-tetrahydro-2,1-benzoxazole-3-carboxamide

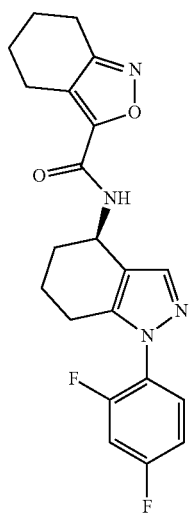 [SMILES: O=C(N[C@@H]1CCCc2c1cnn2-c1ccc(F)cc1F)c1onc2c1CCCC2]

In addition, the following compounds were also prepared in the manner described below.

Example 13: N-[(4R)-1-(2-fluorophenyl)-4,5,6,7-tetrahydro-1H-indazol-4-yl]-4,5,6,7-tetrahydro-1,2-benzoxazole-3-carboxamide

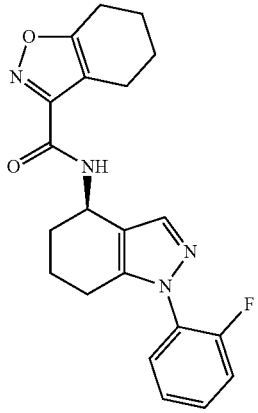 [SMILES: O=C(N[C@@H]1CCCc2c1cnn2-c1ccccc1F)c1noc2c1CCCC2]

Propylphosphonic anhydride solution (59 μl, 0.103 mmol) was added to a slurry of (R)-1-(2-fluorophenyl)-4,5,6,7-tetrahydro-1H-indazol-4-amine hydrochloride (S15) (13.4 mg, 0.050 mmol), 4,5,6,7-tetrahydro-1,2-benzoxazole-3-carboxylic acid (8.4 mg, 0.050 mmol) and triethylamine (29 μl, 0.21 mmol) in THF. The mixture was stirred at RT for 2 h. The reaction mixture was chromatographed through a short silica column eluted with Heptanes:EtOAc 1:1 to give the title compound (5.0 mg, 53%). 1H NMR (400 MHz, METHANOL-d4) δ ppm 7.65 (s, 1H), 7.57-7.50 (m, 1H), 7.50-7.44 (m, 1H), 7.39-7.32 (m, 2H), 5.27-5.21 (m, 1H), 2.76-2.70 (m, 2H), 2.67 (td, J=6.00, 1.20 Hz, 2H), 2.63-2.47 (m, 2H), 2.12-1.97 (m, 2H), 1.93-1.83 (m, 4H), 1.82-1.74 (m, 2H); m/z (ES$^+$) 381 [M+H]$^+$.

Example 14: N-[(4R)-1-(2-fluorophenyl)-4,5,6,7-tetrahydro-1H-indazol-4-yl]-4,5,6,7-tetrahydro-2,1-benzoxazole-3-carboxamide

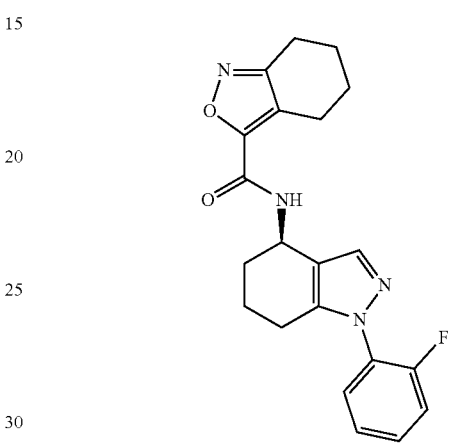

The title compound was prepared using two methods.

Method A: N-[1-(2-fluorophenyl)-4,5,6,7-tetrahydro-1H-indazol-4-yl]-4,5,6,7-tetrahydro-2,1-benzoxazole-3-carboxamide (1 g) was dissolved in methanol (12 ml) and DCM (3 ml) and purified by SFC, injecting 150 μl/run in stacked injections on a Chiral Cellulose column SC (YMC), 250*10 mm eluting with CO2, 20% methanol, 15 ml/min. The solvents were evaporated and the solids dried under vacuum to give a solid (365 mg). $^1$H NMR (400 MHz, Chloroform-d) δ 7.67 (s, 1H), 7.52-7.36 (m, 2H), 7.34-7.17 (m, 2H, overlapping with solvent signal), 6.66 (d, J=8.0 Hz, 1H), 5.31 (dt, J=8.1, 5.1 Hz, 1H), 2.90 (t, J=6.2 Hz, 2H), 2.79 (t, J=6.2 Hz, 2H), 2.57 (qd, J=16.3, 8.4 Hz, 2H), 2.20-2.05 (m, 1H), 1.97-1.72 (m, 7H). m/z (ES$^+$) 381 [M+H]+; Analysis by SFC, Chiral Cellulose SB column, 4.6×150 mm, eluent 20% methanol in supercritical carbon dioxide, 5 ml/min, RT 1.60 min.

Method B: Propylphosphonic anhydride solution (1.15 ml, 2.0 mmol) was added to a slurry of (R)-1-(2-fluorophenyl)-4,5,6,7-tetrahydro-1H-indazol-4-amine hydrochloride (S15) (268 mg, 1.00 mmol), 4,5,6,7-tetrahydrobenzo[c]isoxazole-3-carboxylic acid (167 mg, 1.00 mmol) and triethylamine (0.70 ml, 5.0 mmol) in THF. The mixture was stirred at RT for 1 h. The reaction mixture was chromatographed through a short silica column eluted with Heptanes: EtOAc 1:1. The solvents were evaporated and the residue was recrystallized from methanol to give the title compound as a solid (300 mg, 52%). ¹H NMR (400 MHz, METHANOL-d4) δ ppm 7.64 (s, 1H), 7.54 (m, 1H), 7.47 (m, 1H), 7.36 (s, 2H), 5.25 (m, 1H), 2.85 (d, J=1.26 Hz, 2H), 2.77 (s, 2H), 2.65-2.47 (m, 2H), 2.15-1.99 (m, 2H), 1.93-1.73 (m, 6H).

Example 15: N-[(4R*)-1-(2-fluorophenyl)-4,5,6,7-tetrahydro-1H-indazol-4-yl]-5-methylpyrazine-2-carboxamide (*putative isomer)

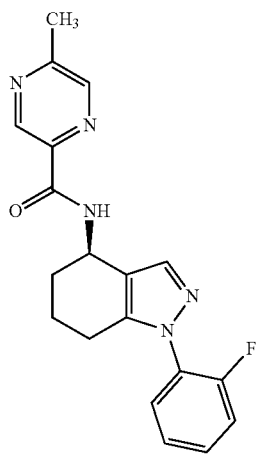 [SMILES: Cc1cnc(C(=O)N[C@@H]2CCCc3c2cnn3-c2ccccc2F)cn1]

To a mixture of 1-(2-fluorophenyl)-4,5,6,7-tetrahydro-1H-indazol-4-amine (20 mg, 0.086 mmol), 5-methylpyrazine-2-carboxylic acid (23 mg, 0.17 mmol) and DIPEA (44 µl, 0.26 mmol) in DCM (2 ml) was added HATU (36 mg, 0.095 mmol) and the reaction was stirred at room temperature for 16 hrs. The mixture was concentrated under reduced pressure. The residue was diluted with EtOAc (10 mL) and washed with saturated brine (3×5 mL), and concentrated. The residue was purified by silica gel chromatography eluting with a stepwise gradient of 0, 1 and 2% of methanol in dichloromethane. The fractions containing product were concentrated to give 20 mg. The enantiomers were separated by SFC using a Chiral Cellulose SC column, 250×10 mm eluting with 45% methanol in supercritical carbon dioxide, flow 15 ml/min. The first eluting peak (RT 5.2 min) was collected. The solvents were evaporated to give the title compound (3.7 mg). ¹H NMR (400 MHz, Chloroform-d) δ 9.32 (d, J=1.4 Hz, 1H), 8.36 (dd, J=1.5, 0.6 Hz, 1H), 7.93 (d, J=8.3 Hz, 1H), 7.68 (s, 1H), 7.52-7.44 (m, 1H), 7.44-7.37 (m, 1H), 7.32-7.19 (m, 2H overlapping with solvent), 5.41-5.32 (m, 1H), 2.65 (s, 3H), 2.63-2.47 (m, 2H), 2.23-2.12 (m, 1H), 2.01-1.83 (m, 3H). m/z (ES⁺) 352 [M+H]⁺.

Example 16: N-[(4R)-1-(2-methylphenyl)-4,5,6,7-tetrahydro-1H-indazol-4-yl]-4,5,6,7-tetrahydro-2,1-benzoxazole-3-carboxamide

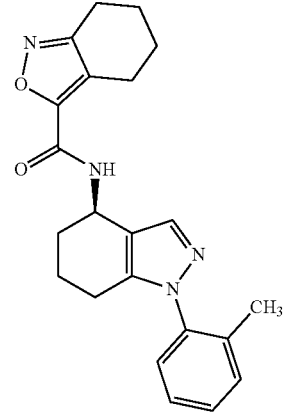 [SMILES: Cc1ccccc1-n1ncc2c1CCC[C@H]2NC(=O)c1onc2c1CCCC2]

To a mixture of (4R)-1-(2-methylphenyl)-4,5,6,7-tetrahydro-1H-indazol-4-amine (S8) (40 mg, 0.18 mmol), 4,5,6,7-tetrahydrobenzo[c]isoxazole-3-carboxylic acid (59 mg, 0.35 mmol) and DIPEA (90 µl, 0.53 mmol) in dichloromethane (2 ml) was added HATU (74 mg, 0.19 mmol) and the reaction was stirred at room temperature for 16 h. The mixture was concentrated under reduced pressure. The residue was diluted with EtOAc (10 ml) and washed with saturated brine (3×10 ml), and concentrated. The residue was dissolved in DMF (2 ml) and was purified by preparative HPLC using gradients of acetonitrile and water containing 0.1% of TFA. The fractions containing product were extracted with dichloromethane and the solvents were evaporated to give the title compound (58 mg, 88%). ¹H NMR (400 MHz, Methanol-d4) δ 7.61 (s, 1H), 7.48-7.37 (m, 2H), 7.37-7.30 (m, 1H), 7.25 (m, 1H), 5.29-5.22 (m, 1H), 2.85 (td, J=6.3, 1.6 Hz, 2H), 2.78 (t, J=6.3 Hz, 2H), 2.53-2.34 (m, 2H), 2.15-1.98 (m, 5H), 1.94-1.73 (m, 6H). m/z (ES⁺) 377 [M+H]⁺.

Example 17: N-[(4R)-1-(2-methylphenyl)-4,5,6,7-tetrahydro-1H-indazol-4-yl]-1-benzofuran-2-carboxamide

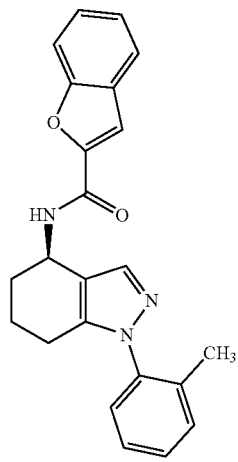 [SMILES: Cc1ccccc1-n1ncc2c1CCC[C@H]2NC(=O)c1cc2ccccc2o1]

The title compound was synthesized using the method described in Example 16 to give (33 mg, 95%).

¹H NMR (400 MHz, Chloroform-d) δ 7.76 (s, 1H), 7.73-7.64 (m, 1H), 7.54 (d, J=1.0 Hz, 1H), 7.52-7.47 (m, 1H), 7.45-7.27 (m, 5H), 7.23 (dd, J=7.8, 1.4 Hz, 1H), 6.87 (d, J=8.1 Hz, 1H), 5.44-5.34 (m, 1H), 2.54-2.33 (m, 2H), 2.28-2.13 (m, 1H), 2.10 (s, 3H), 2.05-1.83 (m, 3H); m/z (ES⁺) 372 [M+H]⁺.

Example 18: 3-methyl-N-[(4R)-1-(2-methylphenyl)-4,5,6,7-tetrahydro-1H-indazol-4-yl]-1-benzofuran-2-carboxamide

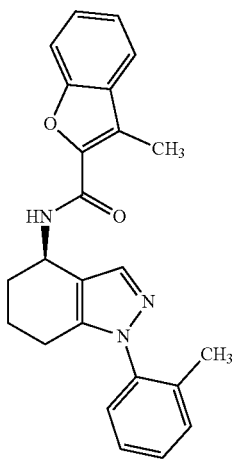 [SMILES: Cc1ccccc1-n1ncc2c1CCC[C@H]2NC(=O)c1oc2ccccc2c1C]

The title compound was synthesized using the method described in Example 16 to give 37 mg (97%).

¹H NMR (400 MHz, Chloroform-d) δ 7.79 (s, 1H), 7.68-7.55 (m, 1H), 7.52-7.17 (m, 7H), 6.85 (d, J=8.1 Hz, 1H), 5.49-5.30 (m, 1H), 2.68 (s, 3H), 2.56-2.33 (m, 2H), 2.28-2.14 (m, 1H), 2.10 (s, 3H), 2.05-1.82 (m, 3H); m/z (ES⁺) 386 [M+H]⁺.

Example 19: 3-methyl-N-[(4R)-1-(2-methylphenyl)-4,5,6,7-tetrahydro-1H-indazol-4-yl]thiophene-2-carboxamide

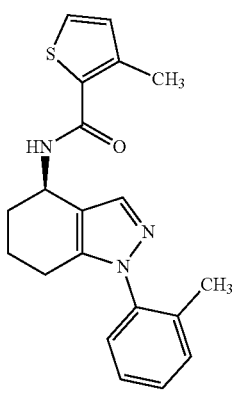 [SMILES: Cc1ccccc1-n1ncc2c1CCC[C@H]2NC(=O)c1sccc1C]

The title compound was synthesized using the method described in Example 16 to give 8.4 mg (27%).

¹H NMR (400 MHz, Chloroform-d) δ 7.65 (s, 1H), 7.39-7.24 (m, 4H, overlapping with solvent signal), 7.24-7.19 (m, 1H), 6.90 (d, J=5.0 Hz, 1H), 5.96 (d, J=7.8 Hz, 1H), 5.31 (q, J=5.5, 4.8 Hz, 1H), 2.55 (s, 3H), 2.51-2.30 (m, 2H), 2.24-2.11 (m, 1H), 2.09 (s, 3H), 1.96-1.77 (m, 3H); m/z (ES⁺) 352 [M+H]⁺.

Example 20: N-[(4R)-1-(2-methylphenyl)-4,5,6,7-tetrahydro-1H-indazol-4-yl]pyridine-2-carboxamide

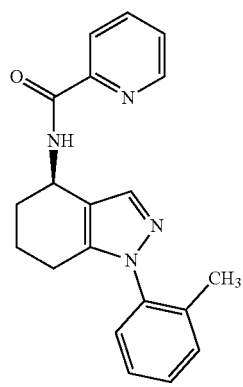 [SMILES: Cc1ccccc1-n1ncc2c1CCC[C@H]2NC(=O)c1ccccn1]

The title compound was synthesized using the method described in Example 16 to give (29 mg, 69%).

¹H NMR (400 MHz, Chloroform-d) δ 8.54 (ddd, J=4.8, 1.8, 0.9 Hz, 1H), 8.33-8.24 (m, 2H), 7.89 (td, J=7.7, 1.7 Hz, 1H), 7.66 (s, 1H), 7.45 (ddd, J=7.6, 4.8, 1.2 Hz, 1H), 7.38-7.20 (m, 4H, overlapping with solvent), 5.39-5.31 (m, 1H), 2.51-2.33 (m, 2H), 2.21-2.11 (m, 1H), 2.10 (s, 3H), 2.03-1.82 (m, 3H); m/z (ES⁺) 333 [M+H]⁺.

Example 21: 2-hydroxy-N-[(4R)-1-(2-methylphenyl)-4,5,6,7-tetrahydro-1H-indazol-4-yl]pyridine-3-carboxamide

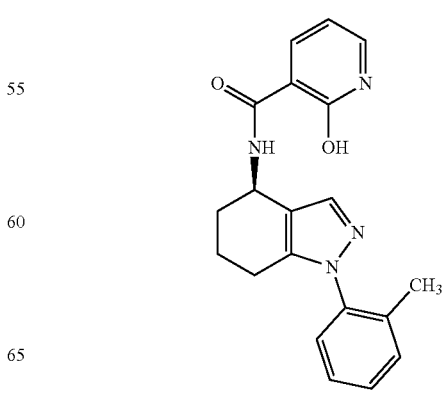

The title compound was synthesized using the method described in Example 16 to give (18.5 mg, 80%)

¹H NMR (400 MHz, chloroform-d) δ 12.29 (s, 1H), 9.88 (d, J=7.5 Hz, 1H), 8.68 (dd, J=7.2, 2.1 Hz, 1H), 7.80 (s, 1H), 7.54 (dd, J=6.3, 2.2 Hz, 1H), 7.42-7.16 (m, 4H), 6.65-6.50 (m, 1H), 5.39-5.23 (m, 1H), 2.53-2.31 (m, 2H), 2.30-2.15 (m, 1H), 2.08 (s, 3H), 2.04-1.94 (m, 1H), 1.94-1.75 (m, 2H); m/z (ES⁺) 349 [M+H]⁺.

Example 22: N-(1-phenyl-4,5,6,7-tetrahydro-1H-indazol-4-yl)-4,5,6,7-tetrahydro-1,2-benzoxazole-3-carboxamide

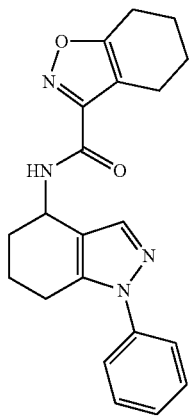 [SMILES: O=C(NC1CCCc2c1cnn2-c1ccccc1)c1noc2c1CCCC2]

The title compound was synthesized using the method described in Example 14 to give 13 mg (53%).

¹H NMR (400 MHz, methanol-d₄) δ ppm 7.59 (s, 1H), 7.54-7.44 (m, 4H), 7.40 (m, 1H) 5.22 (t, J=5.21 Hz, 1H), 2.60-2.83 (m, 7H), 1.95-2.14 (m, 2H), 1.82-1.94 (m, 4H), 1.72-1.81 (m, 2H); m/z (ES⁺) 363[M+H]⁺.

Example 23: N-(1-phenyl-4,5,6,7-tetrahydro-1H-indazol-4-yl)pyridine-2-carboxamide

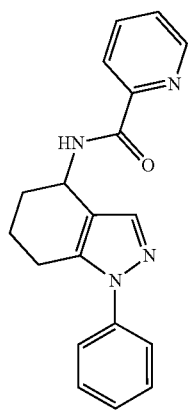 [SMILES: O=C(NC1CCCc2c1cnn2-c1ccccc1)c1ccccn1]

The title compound was synthesized using the method described in Example 14 to yield 8 mg (63%).

1H NMR (400 MHz, methanol-d4) δ ppm 8.73-8.57 (m, 1H), 8.30-8.14 (m, 1H), 8.06 (br. s., 1H), 7.63 (s, 2H), 7.57-7.49 (m, 4H), 7.44 (d, J=2.53 Hz, 1H), 5.29 (br. s., 1H), 3.65 (m, 1H), 2.79 (d, J=16.27 Hz, 2H), 2.23-2.00 (m, 2H), 1.98-1.79 (m, 2H); m/z (ES⁺) 319 [M+H]⁺.

Example 24: 5-methyl-N-[(4R)-1-(2-methylphenyl)-4,5,6,7-tetrahydro-1H-indazol-4-yl]pyridine-2-carboxamide

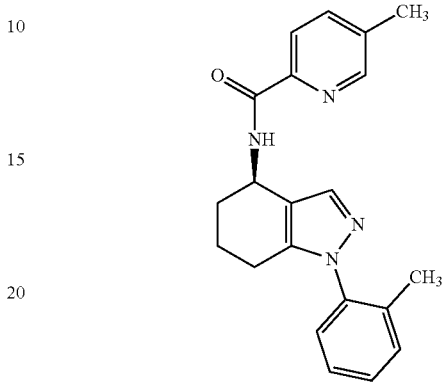

(4R)-1-(2-methylphenyl)-4,5,6,7-tetrahydro-1H-indazol-4-amine (S8) (30 mg, 0.13 mmol), 5-methylpyridine-2-carboxylic acid (19 mg, 0.14 mmol), HATU (55 mg, 0.145 mmol) and DIPEA (69 μl, 0.40 mmol) were dissolved in dichloromethane (2 ml) and DMF (0.2 ml) and was stirred at RT for 4 h. Water (1 ml) was added and the phases were separated. The aqueous phase was extracted with DCM (2×1 ml). The organic phases were combined and concentrated. The residue was dissolved in MeCN 0.5 ml and water 0.5 ml. The mixture was purified by preparative HPLC, Nucleodur polartech column, 20-90% B over 15 min (A: 0.05% formic acid in water; B: 0.05% formic acid in acetonitrile), flow 15 ml/min. Fractions containing product were combined and evaporated to give the title compound (18.6 mg, 41%). ¹H NMR (400 MHz, DMSO-d₆) δ 8.51 (d, J=8.3 Hz, 1H), 8.48-8.43 (m, 1H), 8.00 (d, J=8.0 Hz, 1H), 7.87-7.78 (m, 1H), 7.50 (s, 1H), 7.43-7.37 (m, 2H), 7.37-7.26 (m, 2H), 5.19-5.10 (m, 1H), 2.44-2.28 (m, 5H), 2.04 (s, 3H), 2.01-1.66 (m, 4H); m/z (ES⁺) 347 [M+H]⁺.

Example 25: 4-methyl-N-[(4R)-1-(2-methylphenyl)-4,5,6,7-tetrahydro-1H-indazol-4-yl]pyridine-2-carboxamide

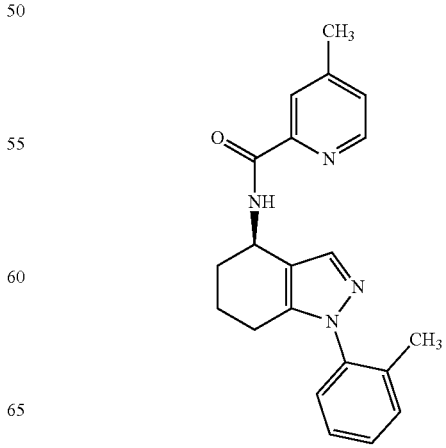

The title compound was prepared using the method described in Example 24 to yield 12 mg (25%).

1H NMR (400 MHz, Chloroform-d) δ 8.39 (dd, J=5.0, 0.7 Hz, 1H), 8.24 (dd, J=16.0, 8.3 Hz, 1H), 8.09 (dt, J=1.8, 0.7 Hz, 1H), 7.64 (s, 1H), 7.38-7.13 (m, 5H, overlapping with solvent signal), 5.38-5.30 (m, 1H), 2.53-2.31 (m, 5H), 2.22-2.11 (m, 1H), 2.09 (s, 3H), 2.07-1.81 (m, 3H); m/z (ES+) 347 [M+H]+.

Example 26: 3-methyl-N-[(4R)-1-(2-methylphenyl)-4,5,6,7-tetrahydro-1H-indazol-4-yl]pyridine-2-carboxamide

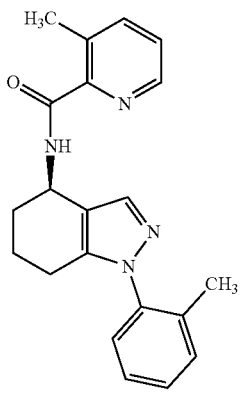 [SMILES: Cc1ccccc1-n1ncc2c1CCC[C@H]2NC(=O)c1ncccc1C]

The title compound was prepared using the method described in Example 24 to yield 27 mg (59%).

1H NMR (400 MHz, Chloroform-d) δ 8.38 (ddd, J=4.6, 1.6, 0.7 Hz, 1H), 8.33 (d, J=8.2 Hz, 1H), 7.64 (s, 1H), 7.63-7.57 (m, 1H), 7.40-7.27 (m, 4H), 7.23 (dd, J=7.6, 1.4 Hz, 1H), 5.30 (dt, J=7.8, 5.6 Hz, 1H), 2.81 (s, 3H), 2.51-2.31 (m, 2H), 2.16 (ddd, J=10.1, 8.6, 5.3 Hz, 1H), 2.11 (s, 3H), 2.00-1.81 (m, 3H); m/z (ES+) 347 [M+H]+.

Example 27: N-(1-phenyl-4,5,6,7-tetrahydro-1H-indazol-4-yl)-4,5,6,7-tetrahydro-2,1-benzoxazole-3-carboxamide

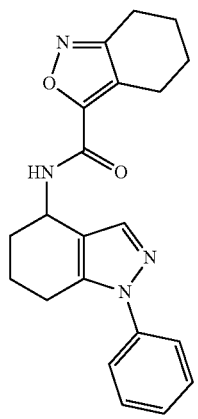 [SMILES: O=C(NC1CCCc2c1cnn2-c1ccccc1)c1onc2c1CCCC2]

The title compound was synthesized using the method described in Example 14 to yield 13 mg (53%).

¹H NMR (400 MHz, METHANOL-d₄) δ ppm 7.60 (s, 1H), 7.56-7.47 (m, 4H), 7.45-7.39 (m, 1H), 5.24 (t, J=5.53 Hz, 1H), 2.88-2.81 (m, 2H), 2.80-2.67 (m, 4H), 2.15-1.99 (m, 2H), 1.94-1.73 (m, 6H); m/z (ES+) 363 [M+H]+.

Example 28: N-[(4R)-1-(2-fluorophenyl)-4,5,6,7-tetrahydro-1H-indazo-4-yl]-1,2-benzoxazole-3-carboxamide

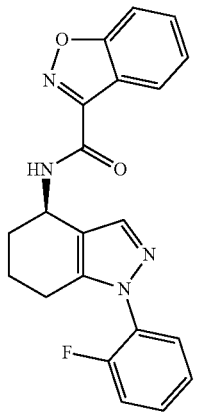 [SMILES: O=C(N[C@@H]1CCCc2c1cnn2-c1ccccc1F)c1noc2ccccc12]

(R)-1-(2-fluorophenyl)-4,5,6,7-tetrahydro-1H-indazol-4-amine hydrochloride (S8) (25 mg, 0.093 mmol), benzo[d]isoxazole-3-carboxylic acid (17 mg, 0.103 mmol), HATU (39 mg, 0.103 mmol) and DIPEA (65 μl, 0.37 mmol) were dissolved in dichlorometane (1.5 ml) and DMF (0.2 ml) and was stirred at RT for 20 h. The reaction mixture was purified by column chromatography eluting with a gradient of EtOAc in hexanes (20-70%). The fractions containing product were evaporated and dried under vacuum to give a white solid (27.6 mg, 78%). ¹H NMR (400 MHz, Chloroform-d) δ 8.34 (dt, J=8.0, 1.1 Hz, 1H), 7.73 (s, 1H), 7.70-7.56 (m, 2H), 7.53-7.37 (m, 3H), 7.34-7.12 (m, 3H, overlapping with solvent), 5.43 (dd, J=8.0, 4.8 Hz, 1H), 2.70-2.50 (m, 2H), 2.19 (ddt, J=12.6, 8.6, 4.1 Hz, 1H), 2.04-1.91 (m, 3H); m/z (ES+) 377 [M+H]+.

Example 29: N-[1-(2-methylphenyl)-4,5,6,7-tetrahydro-1H-indazo-4-yl]-4,5,6,7-tetrahydro-1,2-benzoxazole-3-carboxamide

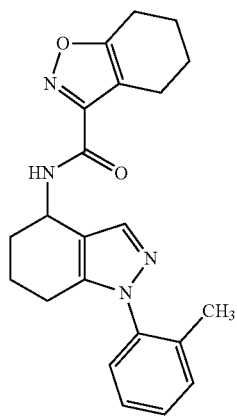 [SMILES: Cc1ccccc1-n1ncc2c1CCCC2NC(=O)c1noc2c1CCCC2]

To a solution of 1-(2-methylphenyl)-4,5,6,7-tetrahydro-1H-indazol-4-amine (S6) (46.8 mg, 0.206 mmol) and HBTU (281 mg, 0.741 mmol) in DMSO (1.2 mL) were added 4,5,6,7-tetrahydro-1,2-benzoxazole-3-carboxylic acid (34.4 mg. 0.206 mmol) and trimethylamine (103 μL, 0.741 mmol). The mixture was stirred at RT for 20 h. The mixture was purified by preparative HPLC to give the title compound as a solid (10.4 mg, 13%). $^1$H NMR (400 MHz, CDCl$_3$) δ 7.60 (s, 1H), 7.43-7.39 (m 2H), 7.34 (m, 1H), 7.24 (m, 1H), 5.25 (m, 1H), 2.76-2.72 (m, 2H), 2.70-2.66 (m, 2H), 2.50-2.34 (m, 2H), 2.13-1.99 (m, 2H), 2.06 (s, 3H), 1.93-1.77 (m, 6H); m/z (ES$^+$) 377 [M+H]$^+$.

Example 30: N-[1-(3-methylphenyl)-4,5,6,7-tetrahydro-1H-indazo-4-yl]-4,5,6,7-tetrahydro-1,2-benzoxazole-3-carboxamide

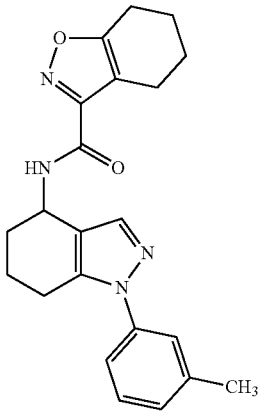 [SMILES: Cc1cccc(-n2ncc3c2CCCC3NC(=O)c2noc3c2CCCC3)c1]

1-(3-Methylphenyl)-4,5,6,7-tetrahydro-H-indazol-4-amine (0.596 mmol), 4,5,6,7-tetrahydrobenzo[d]isoxazole-3-carboxylic acid (99.6 mg, 0.596 mmol) and TBTU (211 mg, 0.655 mmol) were dissolved in dry DMF (4.0 mL) and triethylamine (0.166 mL) was added. The reaction mixture was stirred at RT for 20 h. The mixture was purified with preparative HPLC to give the title compound (0.123 g, 54.8%). $^1$H NMR (400 MHz, CDCl$_3$) δ 7.66 (s, 1H), 7.36-7.32 (m, 2H), 7.24 (br. 1H), 7.17 (m, 1H), 6.96 (d, J=7.9 Hz, 1H), 5.30 (m, 1H), 2.82-2.67 (m, 6H), 2.42 (s, 3H), 2.15-2.09 (m, 1H), 1.97-1.85 (m, 5H), 1.81-1.75 (m, 2H); m/z (ES$^+$) 377 [M+H]$^+$.

Example 31: N-[1-(2,3-dimethylphenyl)-4,5,6,7-tetrahydro-1H-indazo-4-yl]-4,5,6,7-tetrahydro-1,2-benzoxazole-3-carboxamide

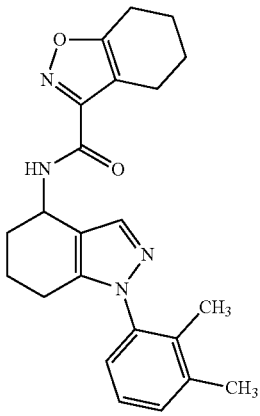 [SMILES: Cc1cccc(-n2ncc3c2CCCC3NC(=O)c2noc3c2CCCC3)c1C]

The title compound was prepared by the method described in Example 30 to give 92 mg (40%). $^1$H NMR (400 MHz, CDCl$_3$) δ 7.60 (s, 1H), 7.2 (d, J=7.5 Hz, 1H), 7.16 (t, J=7.5 Hz, 1H), 7.05 (d, J=7.5 Hz, 1H), 6.98 (d, J=7.8 Hz, 1H), 5.32-5.27 (m, 1H), 2.77-2.70 (m, 4H), 2.42-2.34 (m, 2H), 2.32 (s, 3H), 2.11-2.04 (m, 1H), 1.91 (s, 3H), 1.89-1.81 (m, 5H), 1.79-1.73 (m, 2H); m/z (ES$^+$) 391 [M+H]$^+$.

Example 32: Ethyl 3-[4-(4,5,6,7-tetrahydro-1,2-benzoxazole-3-amido)-4,5,6,7-tetrahydro-1H-indazol-1-yl]benzoate

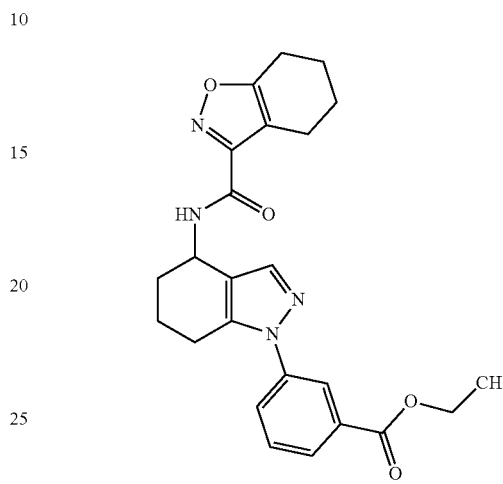

The title compound was prepared by the method described in Example 30 to give 108 mg (41.5%). $^1$H NMR (400 MHz, CDCl$_3$) δ 8.14-8.15 (m, 1H), 8.03 (m, 1H), 7.72 (m, 1H), 7.67 (s, 1H), 7.55 (t, J=8.0 Hz, 1H), 6.95 (d, J=8.1 Hz, 1H), 5.30 (m, 1H), 4.40 (q, J=7.2 Hz, 2H), 2.84-2.71 (m, 6H), 2.13 (m, 1H), 1.97-1.85 (m, 5H), 1.81-1.77 (m, 2H), 1.41 (t, J=7.2 Hz, 3H); m/z (ES$^+$) 435 [M+H]$^+$.

Example 33: N-[(4R)-1-(2-fluorophenyl)-4,5,6,7-tetrahydro-1H-indazol-4-yl]-1,3-benzoxazole-2-carboxamide

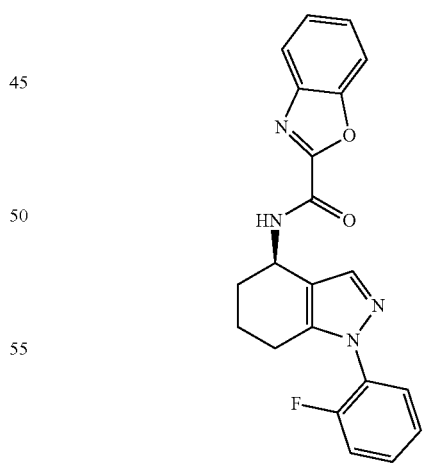

The title compound was prepared using the method described in Example 28 to give a solid (19 mg, 54%). 1H NMR (400 MHz, Chloroform-d) δ 7.78 (ddd, J=7.8, 1.4, 0.7 Hz, 1H), 7.73 (s, 1H), 7.70-7.65 (m, 1H), 7.49-7.36 (m, 5H), 7.34-7.19 (m, 2H, overlapping with solvent signal), 5.39 (dt, J=8.2, 5.2 Hz, 1H), 2.70-2.50 (m, 2H), 2.18 (ddt, J=12.4, 8.4, 3.5 Hz, 1H), 2.07-1.89 (m, 3H); m/z (ES$^+$) 377 [M+H]$^+$.

Example 34: (R)—N-(1-(2-methylphenyl)-4,5,6,7-tetrahydro-1H-indazol-4-yl)-4,5,6,7-tetrahydrobenzo[d]isoxazole-3-carboxamide

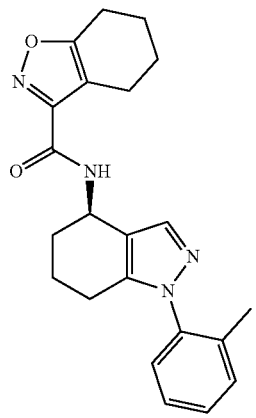 [SMILES: Cc1ccccc1-n1ncc2c1CCC[C@H]2NC(=O)c1noc2c1CCCC2]

To (4R)-1-(2-methylphenyl)-4,5,6,7-tetrahydro-1H-indazol-4-amine (27 mg, 0.12 mmol) (S8) and 4,5,6,7-tetrahydrobenzo[d]isoxazole-3-carboxylic acid (19.9 mg, 0.12 mmol) in THF (1.5 mL) was added DIPEA (0.1 ml, 0.59 mmol) and 1-propanephosphonic acid cyclic anhydride (50 wt % in EtOAc, 0.14 ml, 0.24 mmol). The reaction mixture was stirred at r.t. for 1 h. DIPEA (0.04 ml, 0.24 mmol) and 1-propanephosphonic acid cyclic anhydride (50 wt % in EtOAc, 0.04 ml, 0.06 mmol) were added and the reaction mixture was stirred overnight. The solvents were evaporated and the residue was dissolved in DMF, MeOH and a few drops of TFA, filtered and purified by reverse phase chromatography to give 38 mg (84%) of the title compound. $^1$H NMR (400 MHz, methanol-$d_4$) δ 7.67 (s, 1H), 7.46-7.39 (m, 2H), 7.37-7.33 (m, 1H), 7.26 (d, J=7.5 Hz), 5.25 Hz (t, J=7.0 Hz, 1H), 2.77-2.65 (m, 4H), 2.51-2.36 (m, 2H), 2.14-1.99 (m, 5H), 1.93-1.76 (m, 6H). (ES$^+$) 377 [M+H]$^+$.

Example 35: N-[(4R)-1-(2-fluorophenyl)-4,5,6,7-tetrahydro-1H-indazol-4-yl]-1H-indole-2-carboxamide

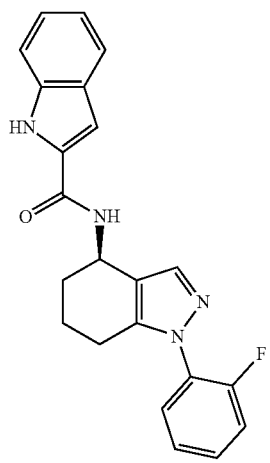 [SMILES: O=C(N[C@@H]1CCCc2c1cnn2-c1ccccc1F)c1cc2ccccc2[nH]1]

The title compound was synthesized using the method described in Example 14B with purification by acidic preparative hplc to give 4 mg (14%). $^1$H NMR (400 MHz, methanol-$d_4$) δ ppm 7.69 (s, 1H), 7.61 (t, J=0.95 Hz, 1H), 7.58-7.51 (m, 1H), 7.48 (s, 1H), 7.46-7.43 (m, 1H), 7.40-7.34 (m, 2H), 7.26-7.18 (m, 1H), 7.14 (d, J=0.79 Hz, 1H), 7.06 (ddd, J=8.06, 7.03, 1.03 Hz, 1H), 5.35-5.28 (m, 1H), 2.71-2.47 (m, 2H), 2.21-2.04 (m, 2H), 1.97-1.83 (m, 2H). m/z (ES$^+$) 375 [M+H]$^+$.

Example 36: 4-chloro-N-[(4R)-1-(2-fluorophenyl)-4,5,6,7-tetrahydro-1H-indazol-4-yl]pyridine-2-carboxamide

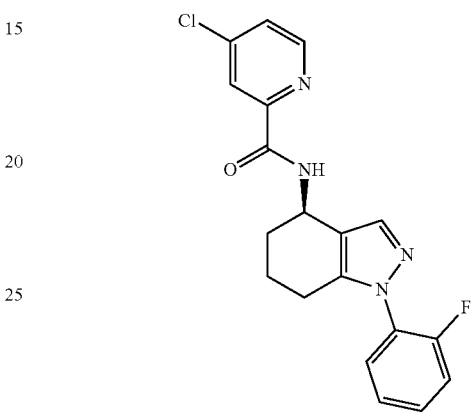

The title compound was synthesized using the method described in Example 14B with purification by acidic preparative hplc to give 12 mg (43%). $^1$H NMR (400 MHz, methanol-$d_4$) δ ppm 8.54 (br. s., 1H), 8.15 (br. s., 1H), 7.65 (s, 1H), 7.62 (d, J=3.48 Hz, 1H), 7.57-7.52 (m, 1H), 7.51-7.46 (m, 1H), 7.39-7.33 (m, 2H), 5.27 (t, J=5.37 Hz, 1H), 2.67-2.46 (m, 2H), 2.19-1.97 (m, 2H), 1.95-1.77 (m, 2H). m/z (ES$^+$) 371 [M+H]$^+$.

Example 37: 4-bromo-N-[(4R)-1-(2-fluorophenyl)-4,5,6,7-tetrahydro-1H-indazol-4-yl]pyridine-2-carboxamide

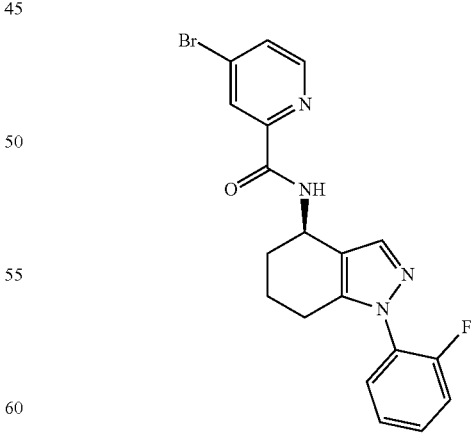

The title compound was synthesized using the method described in Example 14B with purification by acidic preparative hplc to give 9 mg (29%). $^1$H NMR (400 MHz, methanol-$d_4$) δ ppm 8.46 (br. s., 1H), 8.31 (br. s., 1H), 7.78 (d, J=3.79 Hz, 1H), 7.65 (s, 1H), 7.57-7.52 (m, 1H), 7.52-

7.46 (m, 1H), 7.40-7.31 (m, 2H), 5.27 (t, J=5.45 Hz, 1H), 2.67-2.46 (m, 2H), 2.19-1.97 (m, 2H), 1.96-1.82 (m, 2H). m/z (ES+) 415 [M+H]+.

Example 38: (R)—N-(1-(2-fluorophenyl)-4,5,6,7-tetrahydro-1H-indazol-4-yl)-4-methoxyquinoline-2-carboxamide

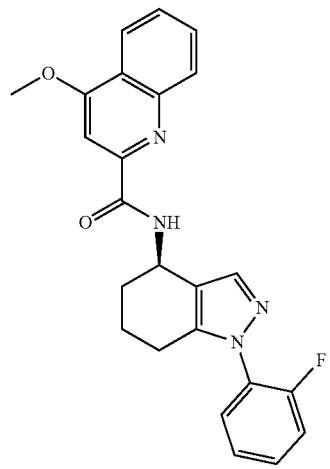 [SMILES: COc1cc(C(=O)N[C@@H]2CCCc3c2cnn3-c2ccccc2F)nc2ccccc12]

The title compound was synthesized using the method described in Example 14B with purification by acidic preparative hplc to give 13 mg (42%). ¹H NMR (400 MHz, methanol-d₄) δ ppm 8.28 (d, J=8.37 Hz, 1H), 8.14 (d, J=8.53 Hz, 1H), 7.93-7.85 (m, 1H), 7.80 (s, 1H) 7.73 (s, 1H), 7.72-7.67 (m, 1H), 7.57-7.51 (m, 1H), 7.42-7.30 (m, 2H) 7.51-7.46 (m, 1H), 5.36 (t, J=5.45 Hz, 1H), 4.25 (s, 3H), 2.72-2.46 (m, 2H), 2.24-1.79 (m, 4H). m/z (ES+) 417[M+H]+.

Example 39: N-[(4R)-1-(2-fluorophenyl)-4,5,6,7-tetrahydro-1H-indazol-4-yl]-4-(trifluoromethyl)pyridine-2-carboxamide

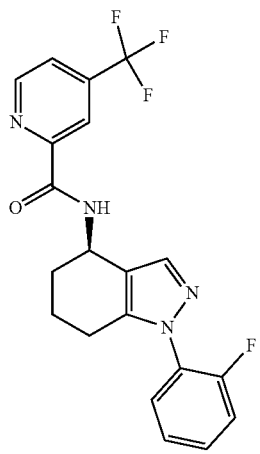 [SMILES: O=C(N[C@@H]1CCCc2c1cnn2-c1ccccc1F)c1cc(C(F)(F)F)ccn1]

The title compound was prepared using the method described in Example 28 to yield 11 mg (27%) of a solid. ¹H NMR (400 MHz, DMSO-d₆) δ 8.92 (dd, J=16.9, 6.7 Hz, 2H), 8.33-8.27 (m, 1H), 8.07-8.00 (m, 1H), 7.60 (s, 1H), 7.58-7.43 (m, 3H), 7.42-7.33 (m, 1H), 5.25-5.17 (m, 1H), 2.04-1.83 (m, 4H), 1.83-1.68 (m, 2H). m/z (ES+) 405 [M+H]+.

Example 40: N-[(4R)-1-(2-fluorophenyl)-4,5,6,7-tetrahydro-1H-indazol-4-yl]-5-(trifluoromethyl)pyridine-2-carboxamide

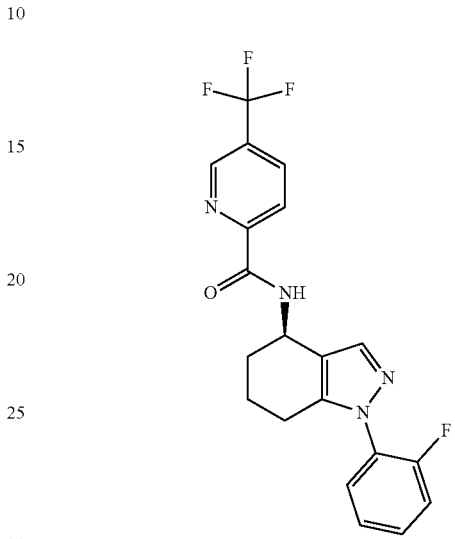

The title compound was prepared using the method described in Example 28 to yield 12 mg (29%). ¹H NMR (400 MHz, DMSO-d₆) δ 9.06-9.00 (m, 1H), 8.87 (d, J=8.3 Hz, 1H), 8.45 (dd, J=8.4, 2.3 Hz, 1H), 8.28 (d, J=8.2 Hz, 1H), 7.59 (s, 1H), 7.58-7.44 (m, 3H), 7.42-7.33 (m, 1H), 5.24-5.14 (m, 1H), 2.05-1.69 (m, 5H). m/z (ES+) 405 [M+H]+.

Example 41: N-[(4R)-1-(2-fluorophenyl)-4,5,6,7-tetrahydro-1H-indazol-4-yl]-5-methylpyridine-2-carboxamide

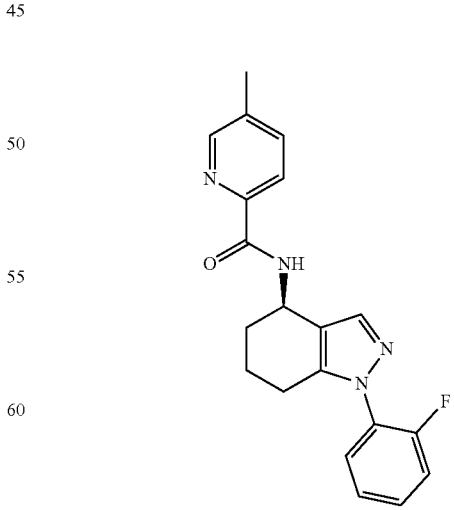

The title compound was prepared using the method described in Example 28 to yield 15 mg (42%). ¹H NMR (400 MHz, DMSO-d$_6$) δ 8.55 (d, J=8.3 Hz, 1H), 8.49-8.42 (m, 1H), 7.99 (d, J=8.0 Hz, 1H), 7.86-7.78 (m, 1H), 7.60-7.44 (m, 4H), 7.41-7.33 (m, 1H), 5.19-5.10 (m, 1H), 2.38 (s, 3H), 2.05-1.68 (m, 4H). m/z (ES$^+$) 351 [M+H]$^+$.

Example 42: (R)—N-(1-(2-fluorophenyl)-4,5,6,7-tetrahydro-1H-indazol-4-yl)-4-methylpicolinamide

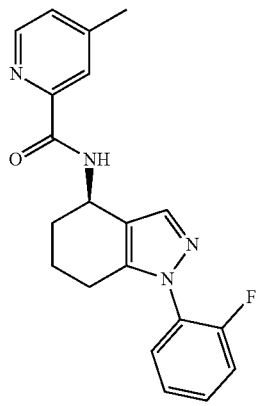 [SMILES: Cc1ccnc(C(=O)N[C@@H]2CCCc3c2cnn3-c2ccccc2F)c1]

The title compound was prepared using the method described in Example 28 to yield 11 mg (47%). $^1$H NMR (400 MHz, methanol-d$_4$) δ 8.46 (dd, J=5.0, 0.8 Hz, 1H), 8.03-7.96 (m, 1H), 7.65 (s, 1H), 7.60-7.46 (m, 2H), 7.43-7.32 (m, 3H), 5.27 (t, J=5.8 Hz, 1H), 2.69-2.49 (m, 1H), 2.47 (s, 3H), 2.23-1.83 (m, 5H). m/z (ES$^+$) 351 [M+H]$^+$.

Example 43: 4-methyl-N-(1-phenyl-4,5,6,7-tetrahydro-1H-indazol-4-yl)pyridine-2-carboxamide

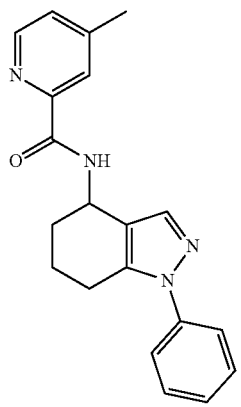 [SMILES: Cc1ccnc(C(=O)NC2CCCc3c2cnn3-c2ccccc2)c1]

The title compound was prepared using the method described in Example 28 to yield 23 mg (69%). $^1$H NMR (400 MHz, CDCl$_3$) δ 8.34 (dt, J=2.2, 0.8 Hz, 1H), 8.18 (d, J=8.4 Hz, 1H), 8.14 (d, J=8.0 Hz, 1H), 7.68 (s, 1H), 7.68-7.63 (m, 1H), 7.53-7.44 (m, 1H), 7.44-7.36 (m, 1H), 7.31-7.19 (m, 3H), 5.39-5.30 (m, 1H), 2.68-2.48 (m, 2H), 2.40 (s, 3H), 2.25-2.10 (m, 1H), 2.02-1.81 (m, 3H). m/z (ES$^+$) 333 [M+H]$^+$.

Example 44: N-[(4R)-1-(2-fluorophenyl)-4,5,6,7-tetrahydro-1H-indazo-4-yl]-4,5-dimethylpyridine-2-carboxamide

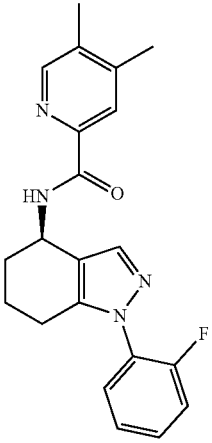 [SMILES: Cc1cnc(C(=O)N[C@@H]2CCCc3c2cnn3-c2ccccc2F)cc1C]

Lithium 4,5-dimethylpyridine-2-carboxylate (S20) (19 mg, 0.12 mmol) was suspended in DMF (2 ml). HBTU (59 mg, 0.16 mmol) was added and the mixture was left to stir for 1 h at r.t. (R)-1-(2-Fluorophenyl)-4,5,6,7-tetrahydro-1H-indazol-4-amine hydrochloride (S15) (45 mg, 0.17 mmol) was added and the reaction mixture was stirred at r.t. overnight. DIPEA (81 μl, 0.47 mmol) and HBTU (59 mg, 0.16 mmol) was added and the reaction was stirred at r.t. overnight. The solvent was removed under a stream of nitrogen and the product was purified by column chromatography eluting with gradients of EtOAc in pentane (20-70%) to give the title compound 34 mg (79%), yield over two steps from methyl 4,5-dimethylpyridine-2-carboxylate (S19). $^1$H NMR (400 MHz, CDCl$_3$) δ 8.22 (s, 1H), 8.18 (d, J=8.2 Hz, 1H), 8.02 (s, 1H), 7.68 (s, 1H), 7.47 (td, J=7.7, 1.8 Hz, 1H), 7.44-7.36 (m, 1H), 7.29-7.20 (m, 2H, overlapping with the solvent peak), 5.39-5.28 (m, 1H), 2.68-2.48 (m, 2H), 2.35 (s, 3H), 2.30 (s, 3H), 2.23-2.09 (m, 1H), 2.02-1.81 (m, 3H). m/z (ES$^+$) 365 [M+H]$^+$.

Example 45: 6-methyl-N-[(4R)-1-(2-methylphenyl)-4,5,6,7-tetrahydro-1H-indazol-4-yl]pyridine-2-carboxamide

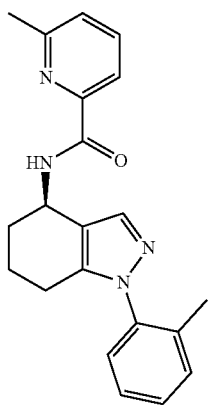 [SMILES: Cc1cccc(C(=O)N[C@@H]2CCCc3c2cnn3-c2ccccc2C)n1]

The title compound was prepared using the method described in Example 16 to yield 37 mg (82%). $^1$H NMR (400 MHz, CDCl$_3$) δ 8.53 (d, J=8.3 Hz, 1H), 8.10 (d, J=7.7 Hz, 1H), 7.82 (t, J=7.7 Hz, 1H), 7.77 (s, 1H), 7.43-7.20 (m, 5H), 5.40-5.31 (m, 1H), 2.61 (s, 3H), 2.54-2.31 (m, 2H), 2.20 (ddt, J=12.3, 7.2, 3.6 Hz, 1H), 2.09 (s, 3H), 2.07-1.96 (m, 1H), 1.95-1.82 (m, 2H). m/z (ES⁺) 347 [M+H]⁺.

Example 46: (R)—N-(1-(2-fluorophenyl)-4,5,6,7-tetrahydro-1H-indazo-4-yl)-5,6,7,8-tetrahydroimidazo[1,5-a]pyridine-1-carboxamide

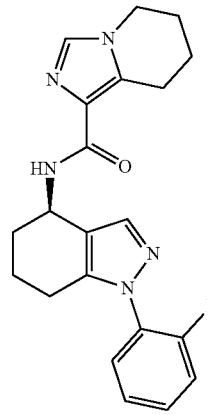

(R)-1-(2-Fluorophenyl)-4,5,6,7-tetrahydro-1H-indazol-4-amine hydrochloride (S15) (35 mg, 0.13 mmol), potassium 5,6,7,8-tetrahydroimidazo[1,5-a]pyridine-1-carboxylate (30 mg, 0.14 mmol), HATU (55 mg, 0.14 mmol) and DIPEA (68 μl, 0.39 mmol) were mixed in DCM (1.5 ml) and DMF (0.15 ml) and the mixture was stirred at r.t. overnight. The solvents were evaporated. The product was purified by column chromatography eluting with a gradient of methanol in DCM (2-10%). One third of the isolated material was dissolved in dichloromethane. The organic phase was washed with NaHCO₃ (sat, aq.). The organic phase was concentrated at reduced pressure and the product was further dried under vacuum to give the title compound 6 mg (11%). ¹H NMR (400 MHz, CDCl₃) δ 7.67 (s, 1H), 7.46 (td, J=7.6, 1.7 Hz, 1H), 7.43-7.36 (m, 1H), 7.30-7.18 (m, 3H, overlapping with the solvent peak), 5.39-5.25 (m, 1H), 4.01 (t, J=6.0 Hz, 2H), 3.21 (t, J=6.5 Hz, 2H), 2.65-2.44 (m, 2H), 2.16-2.02 (m, 2H), 2.02-1.78 (m, 6H). m/z (ES⁺) 380 [M+H]⁺.

Example 47: 4-fluoro-N-[(4R)-1-(2-fluorophenyl)-4,5,6,7-tetrahydro-1H-indazol-4-yl]pyridine-2-carboxamide

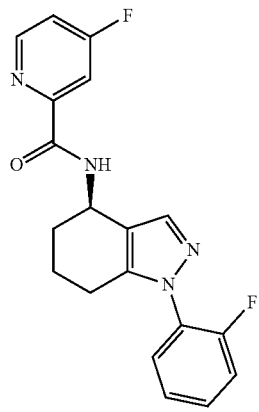 [SMILES: O=C(N[C@@H]1CCCc2c1cnn2-c1ccccc1F)c1cc(F)ccn1]

The title compound was prepared using the method described in Example 28 to yield 28 mg (85%). ¹H NMR (400 MHz, methanol-d4) δ 8.64 (dd, J=8.0, 5.6 Hz, 1H), 7.90 (dd, J=9.5, 2.4 Hz, 1H), 7.65 (s, 1H), 7.58-7.45 (m, 2H), 7.42-7.32 (m, 3H), 5.28 (t, J=5.7 Hz, 1H), 4.62 (s, 1H), 2.59 (m, 2H), 2.22-1.83 (m, 5H). m/z (ES⁺) 356 [M+H]+

Example 48: (R)—N-(1-(2-fluorophenyl)-4,5,6,7-tetrahydro-1H-indazol-4-yl)imidazo[1,5-a]pyridine-3-carboxamide

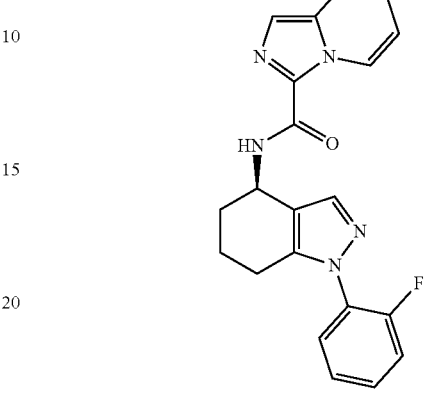

Ethyl imidazo[1,5-a]pyridine-3-carboxylate (25 mg, 0.13 mmol), (R)-1-(2-fluorophenyl)-4,5,6,7-tetrahydro-1H-indazol-4-amine hydrochloride (S15) (49 mg, 0.18 mmol) and bis(trimethylaluminum)-1,4-diazabicyclo[2.2.2]octane adduct (51 mg, 0.20 mmol) were dissolved in THF (2 ml). The reaction mixture was stirred at 60° C. for 5 h under nitrogen atmosphere. The solvent was removed at reduced pressure and DCM and brine were added. The phases were separated and the organic phase was filtered and concentrated. The mixture was purified by column chromatography eluting with a gradient of EtOAc in hexanes (20-70%) to give the title compound, 31 mg (62%). ¹H NMR (400 MHz, CDCl₃) δ 9.54 (d, J=8.2 Hz, 1H), 7.71 (s, 1H), 7.57 (d, J=9.1 Hz, 1H), 7.53 (d, J=7.7 Hz, 1H), 7.48 (td, J=7.7, 1.7 Hz, 1H), 7.45 (d, J=0.7 Hz, 1H), 7.44-7.37 (m, 1H), 7.30-7.20 (m, 2H, overlapping with the solvent peak), 6.98 (ddd, J=9.1, 6.6, 1.0 Hz, 1H), 6.85 (ddd, J=7.2, 6.6, 1.3 Hz, 1H), 5.43-5.32 (m, 1H), 2.68-2.49 (m, 2H), 2.22-2.09 (m, 1H), 2.03-1.82 (m, 3H). m/z (ES⁺) 376 [M+H]⁺.

Example 49: (R)—N-(1-(2-fluoro-5-methylphenyl)-4,5,6,7-tetrahydro-1H-indazol-4-yl)-4,5,6,7-tetrahydrobenzo[c]isoxazole-3-carboxamide

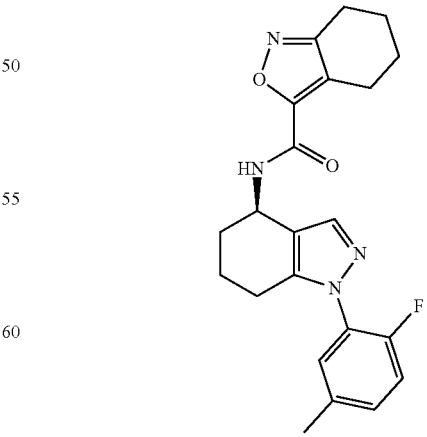

4,5,6,7-Tetrahydrobenzo[c]isoxazole-3-carboxylic acid (26 mg, 0.15 mmol), HATU (60 mg, 0.16 mmol), (R)-1-(2-fluoro-5-methylphenyl)-4,5,6,7-tetrahydro-1H-indazol-4- amine (S23) (35 mg, 0.14 mmol) and DIPEA (50 µl, 0.29 mmol) were mixed in DCM (1.5 ml) and DMF (0.2 ml) and the mixture was stirred at r.t. overnight. The mixture was purified by column chromatography eluting with a gradient of EtOAc in hexanes (20-70%) to give the title compound 29 mg (49%). $^1$H NMR (400 MHz, CDCl$_3$) δ 7.66 (s, 1H), 7.31-7.23 (m, 1H, overlapping with the solvent peak), 7.22-7.16 (m, 1H), 7.11 (dd, J=10.1, 8.5 Hz, 1H), 6.66 (d, J=8.1 Hz, 1H), 5.36-5.25 (m, 1H), 2.89 (t, J=6.0 Hz, 2H), 2.78 (t, J=6.2 Hz, 2H), 2.67-2.47 (m, 2H), 2.37 (s, 3H), 2.18-2.06 (m, 1H), 1.96-1.69 (m, 7H). m/z (ES$^+$) 395 [M+H]$^+$.

Example 50: N-[(4R)-1-(2-fluoro-5-methylphenyl)-4,5,6,7-tetrahydro-1H-indazol-4-yl]-4-(trifluoromethyl)pyridine-2-carboxamide

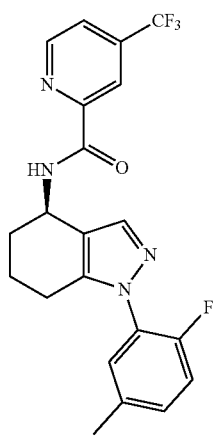 [SMILES: Cc1ccc(F)c(-n2ncc3c2CCC[C@H]3NC(=O)c2cc(C(F)(F)F)ccn2)c1]

4-(Trifluoromethyl)picolinic acid (30 mg, 0.15 mmol), HATU (60 mg, 0.16 mmol), (4R)-1-(2-fluoro-5-methylphenyl)-4,5,6,7-tetrahydro-1H-indazol-4-amine (S23) (35 mg, 0.14 mmol) and DIPEA (50 µl, 0.29 mmol) were mixed in DCM (1.5 ml) and DMF (0.2 ml) and the mixture was stirred at r.t. overnight. The mixture was purified by column chromatography eluting with a gradient of EtOAc in hexanes (20-70%) to give the title compound, 22 mg (37%). $^1$H NMR (400 MHz, CDCl$_3$) δ 8.73 (d, J=5.0 Hz, 1H), 8.50 (s, 1H), 8.18 (d, J=8.0 Hz, 1H), 7.71-7.62 (m, 2H), 7.28 (dd, J=7.2, 2.0 Hz, 1H), 7.22-7.16 (m, 1H), 7.11 (dd, J=10.0, 8.5 Hz, 1H), 5.42-5.30 (m, 1H), 2.71-2.50 (m, 2H), 2.37 (s, 3H), 2.26-2.11 (m, 1H), 2.01-1.81 (m, 3H). m/z (ES$^+$) 419 [M+H]$^+$.

Example 51: N-[(4R)-1-(2-fluoro-5-methylphenyl)-4,5,6,7-tetrahydro-1H-indazol-4-yl]-4-methylpyridine-2-carboxamide

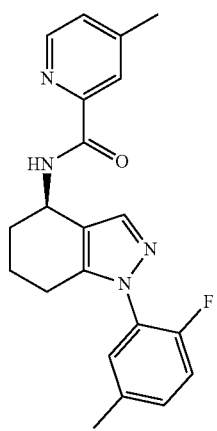 [SMILES: Cc1ccnc(C(=O)N[C@@H]2CCCc3c2cnn3-c2cc(C)ccc2F)c1]

4-Methylpicolinic acid (22 mg, 0.15 mmol), HATU (70 mg, 0.18 mmol), (R)-1-(2-fluoro-5-methylphenyl)-4,5,6,7-tetrahydro-1H-indazol-4-amine (S23) (35 mg, 0.14 mmol) and DIPEA (50 µl, 0.29 mmol) were dissolved in DCM (1.5 ml) and DMF (0.3 ml) and the solution was stirred at r.t. overnight. The reaction mixture was concentrated under a stream of nitrogen and the mixture was purified by column chromatography eluting with a gradient of EtOAc in hexanes (20-70%) to give the title compound 22 mg (40%). $^1$H NMR (400 MHz, CDCl$_3$) δ 8.37 (d, J=5.4 Hz, 1H), 8.23 (d, J=8.4 Hz, 1H), 8.11-8.06 (m, 1H), 7.67 (s, 1H), 7.28 (dd, J=7.3, 2.1 Hz, 1H, overlapping with the solvent peak), 7.23 (ddd, J=4.9, 1.8, 0.8 Hz, 1H), 7.21-7.15 (m, 1H), 7.10 (dd, J=10.1, 8.4 Hz, 1H), 5.40-5.29 (m, 1H), 2.69-2.48 (m, 2H), 2.45 (s, 3H), 2.37 (s, 3H), 2.24-2.09 (m, 1H), 2.02-1.80 (m, 3H). m/z (ES$^+$) 365 [M+H]$^+$.

Example 52: Propan-2-yl-3-[(4R)-4-(4,5,6,7-tetrahydro-1,2-benzoxazole-3-amido)-4,5,6,7-tetrahydro-1H-indazol-1-yl]benzoate

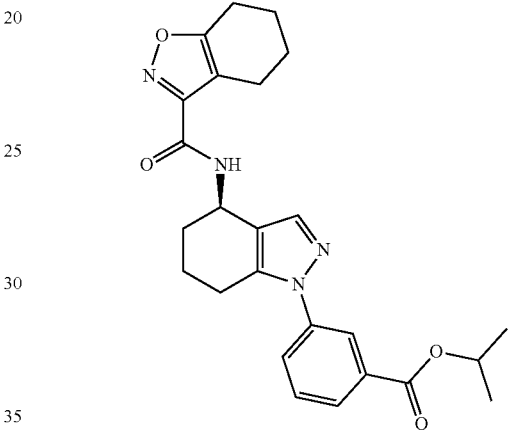

The title compound was synthesized using the method described in Example 14B with purification by silica gel chromatography, eluted with a gradient of hexanes/Ethyl acetate 3:1 to 1:1 to give 90 mg (71%). $^1$H NMR (400 MHz, METHANOL-d$_4$) δ ppm 8.12 (m, J=2.17, 1.05, 1.05 Hz, 1H), 8.03 (m, J=9.00 Hz, 1H), 7.78-7.73 (m, 1H), 7.67-7.61 (m, 2H, 5.26-5.23 (m, 1H), 5.25 (spt, J=6.24 Hz, 1H), 2.88-2.75 (m, 2H), 2.75-2.65 (m, 4H), 2.18-1.99 (m, 2H), 1.89 (dd, J=6.00, 2.21 Hz, 4H), 1.80 (s, 2H) 1.39 (d, J=6.16 Hz, 6H). m/z (ES$^+$) 449 [M+H]$^+$.

Example 53: N-[(4R)-1-[3-(morpholine-4-carbonyl)phenyl]-4,5,6,7-tetrahydro-1H-indazol-4-yl]-4,5,6,7-tetrahydro-1,2-benzoxazole-3-carboxamide

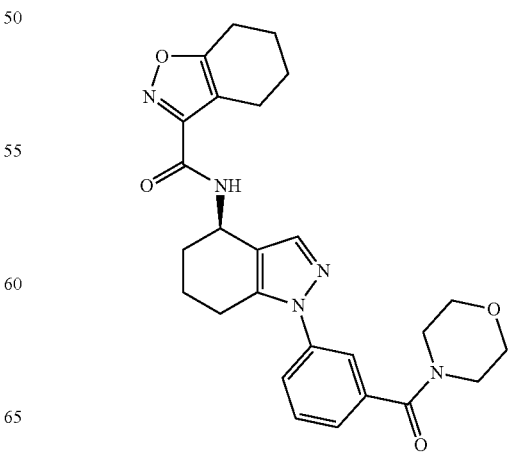

Propan-2-yl-3-[(4R)-4-(4,5,6,7-tetrahydro-1,2-benzoxazole-3-amido)-4,5,6,7-tetrahydro-1H-indazol-1-yl]benzoate (Example 52) (45 mg, 0.1 mmol) was treated with sodium hydroxide solution (aq., 5 mL, 4 M) in methanol (5 mL) at 50° C. for 1 h, then acidified with diluted hydrochloric acid and extracted with ethyl acetate, dried (Na2SO4) and evaporated. The material was purified by acidic preparative HPLC to give (R)-3-(4-(4,5,6,7-tetrahydrobenzo[d]isoxazole-3-carboxamido)-4,5,6,7-tetrahydro-1H-indazol-1-yl)benzoic acid, 25 mg (41%); m/z (ES$^+$) 407 [M+H]$^+$. The carboxylic acid (18 mg, 0.04 mmol) was treated with morpholine using the method describe in example 14B. The title compound was isolated by acidic preparative HPLC to give 14 mg (67%). $^1$H NMR (400 MHz, methanol-d$_4$) δ ppm 7.62-7.65 (m, 3H) 7.58-7.60 (m, 1H) 7.47 (ddd, J=6.28, 2.41, 1.74 Hz, 1H) 5.21-5.26 (m, 1H) 3.77 (br. s., 4H) 3.65 (br. s., 3H) 3.50 (br. s., 2H) 2.77-2.89 (m, 2H) 2.71-2.76 (m, 2H) 2.67 (td, J=6.00, 1.26 Hz, 2H) 2.08 (m, J=5.37 Hz, 2H) 1.84-1.95 (m, 4H) 1.79 (m, 2H); m/z (ES$^+$) 476 [M+H]$^+$.

Synthesis of Starting Materials

S1: 2-((dimethylamino)methylene)cyclohexane-1,3-dione

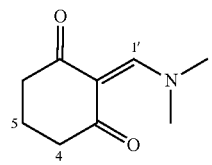

A solution of 1,3-cyclohexanedione (5.0 g, 44.6 mmol, 1.0 eq.) in N,N-dimethylformamide dimethyl acetal (8.9 mL, 66.9 mmol, 1.5 eq.) was heated at reflux for 2 h. Upon cooling, an orange solid precipitated, which was stirred in Et$_2$O (40 mL) and collected by filtration to give the title product (S1) as an orange powder (5.3 g, 71%), which did not require further purification.

Analysis of the product found: mp 101-103° C.; $^1$H NMR (300 MHz, CDCl$_3$) δ 8.04 (s, 1H, C1'-H), 3.38 (s, 3H, CH$_3$), 3.16 (s, 3H, CH$_3$), 2.46 (dd, J=8.6, 4.3 Hz, 4H, 2×C4-H$_2$), 2.00-1.87 (m, 2H, C5-H$_2$); $^{13}$C NMR (75 MHz, CDCl$_3$) δ 195.2 (2×CO), 161.2 (C1'), 108.4 (C2), 47.5 (CH$_3$), 43.7 (CH$_3$), 37.2 (C4), 18.6 (C5); m/z (ES$^+$) 168.04 ([M+H]$^+$, 100%). Data are in agreement with the literature (Hong et al., J Med Chem., 28; 54(14), 5070-81 (2011)).

S2: 1-(2-Fluorophenyl)-6,7-dihydro-1H-indazol-4(5H)-one

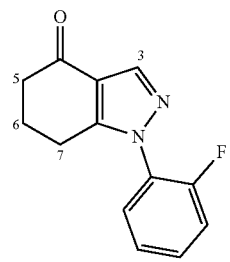 [SMILES: O=C1CCCc2c1cnn2-c1ccccc1F]

To a solution of 2-((dimethylamino)methylene)cyclohexane-1,3-dione (S1) (1.67 g, 10 mmol, 1.0 eq.) in methanol (60 mL) and water (10 mL) were added 4-fluorophenylhydrazine hydrochloride (1.63 g, 10 mmol, 1.0 eq.) and sodium hydroxide (0.4 g, 10 mmol, 1.0 eq.). The resulting mixture was heated at reflux for 2 h and concentrated under reduced pressure. To the residue were added AcOH (60 mL) and water (30 mL) and the corresponding mixture was heated to 110° C. On completion of the reaction, the solution was concentrated in vacuo. The residue was diluted with EtOAc (100 mL) and washed thoroughly with a sat. aq. NaHCO$_3$ solution (50 mL) and brine (50 mL), dried over MgSO$_4$, filtered and concentrated. The crude product was purified via the Biotage SP4 (silica-packed SNAP 50 g; 25-50% EtOAc/hexanes) to provide the title product (S2) as a yellow solid (1.77 g, 77%).

Analysis of the product found: mp 104-106° C.; IR (KBr) v$_{max}$: 2957, 1663 (C=O), 1508, 1408, 1226; $^1$H NMR (400 MHz, CDCl$_3$) δ 8.10 (s, 1H, C3-H), 7.60-7.43 (m, 2H, 2×ArH), 7.36-7.22 (m, 2H, 2×ArH), 2.82-2.78 (m, 2H, C7-H$_2$), 2.57-2.53 (m, 2H, C5-H$_2$), 2.27-2.06 (m, 2H, C6-H$_2$); $^{13}$C NMR (101 MHz, CDCl$_3$) 193.2 (CO), 157.2 (C), 154.7 (C), 151.5 (C7a), 139.0 (C3), 130.8 (d, J=7.7 Hz, CH), 128.4 (CH), 125.1 (d, J=3.9 Hz, CH), 120.1 (C3a), 116.8 (d, J=19.7 Hz, CH), 37.9 (C5), 23.4 (C6), 22.0 (C7); m/z (ES$^+$) 252.89 ([M+Na]$^+$, 100%); HRMS (ES$^+$) Calcd for C$_{13}$H$_{11}$N$_2$OFNa [M+Na]$^+$: 253.0753, found 253.0757.

S3: (S)—N—((S)-1-(2-Fluorophenyl)-4,5,6,7-tetrahydro-1H-indazol-4-yl)-2-methylpropane-2-sulfinamide

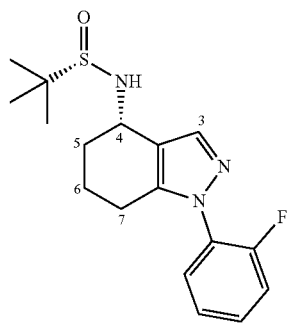 [SMILES: CC(C)(C)[S@](=O)N[C@H]1CCCc2c1cnn2-c1ccccc1F]

1-(2-Fluorophenyl)-6,7-dihydro-1H-indazol-4(5H)-one (S2) (500 mg, 2.2 mmol, 1.0 eq.) was added to (S$_S$)-2-methyl-2-propanesulfinamide (316 mg, 2.6 mmol, 1.2 eq.) and Ti(OEt)$_4$ (0.91 mL, 4.3 mmol, 2.0 eq.) in THF (5 mL) at r.t. The mixture was heated at 75° C. for 12 h. The mixture was cooled to −48° C. and NaBH$_4$ (205 mg, 5.4 mmol, 2.5 eq.) was added. Once the reduction was complete, the reaction mixture was warmed to 0° C. and MeOH was added dropwise until gas evolution was no longer observed. The crude reaction mixture was poured into brine (5 mL) whilst being vigorously stirred. The resulting suspension was filtered through a celite, and the filter cake was washed with EtOAc (2×5 mL). The filtrate was washed with brine (20 mL), and the brine layer was extracted with EtOAc (3×10 mL). The combined organic extracts were dried over MgSO$_4$, filtered, concentrated in vacuo and purified via the Biotage SP4 (silica-packed SNAP column 10 g; 20-70% EtOAc/hexanes) to give the title product (S3) as a white solid (577 mg, 79%).

Analysis of the product found: mp 94-96° C.; IR (KBr) v$_{max}$: 3418 (NH), 3220, 2921, 1667, 1460, 1194; 1H NMR (500 MHz, CDCl$_3$) δ 7.81 (s, 1H, C3-H), 7.46 (td, J=7.8, 1.7 Hz, 1H, ArH), 7.39 (tdd, J=7.8, 4.8, 1.7 Hz, 1H, ArH), 7.33-7.16 (m, 2H, 2×ArH), 4.59 (q, J=4.9 Hz, 1H, C4-H), 3.31 (d, J=4.9 Hz, 1H, NH), 2.52 (qt, J=17.0, 6.1 Hz, 1H, C7-H$_2$), 2.00-1.91 (m, 2H, C5-H, C6-H), 1.91-1.72 (m, 2H, C5-H, C6-H), 1.24 (s, 9H, 3×CH$_3$); $^{13}$C NMR (101 MHz, CDCl$_3$) δ 156.4 (d, J=251.4 Hz, C), 141.8 (C7a), 139.8 (C3), 130.1 (d, J=7.8 Hz, CH), 128.8 (CH), 127.5 (d, J=11.9 Hz, C), 124.9 (d, J=3.8 Hz, CH), 118.9 (C3a), 116.7 (d, J=20.0 Hz, CH), 55.7 (C), 48.3 (C4), 31.5 (C5), 22.8 (3×CH₃), 21.7 (C7), 19.4 (C8); m/z (ES⁺) 358.98 ([M+Na]⁺, 100%).

S4: (S)—N—((R)-1-(2-Fluorophenyl)-4,5,6,7-tetrahydro-1H-indazol-4-yl)-2-methylpropane-2-sulfinamide 1-(2-Fluorophenyl)-6,7-dihydro-1H-indazol-4(5H)-one (S2) (4.64 g, 20.1 mmol, 1.0 eq.) was added to (S$_S$)-2-methyl-2-propanesulfinamide (2.44 g, 20.1 mmol, 1.0 eq.) and Ti(OEt)₄ (8.4 mL, 40.2 mmol, 2.0 eq.) in THF (40 mL) at r.t. The mixture was heated at 75° C. for 12 h. The mixture was then cooled to −48° C. and L-selectride (60.3 mL, 1 M, 3.0 eq.) was added dropwise. Once the reduction was complete, the reaction mixture was warmed to 0° C. and MeOH was added dropwise until gas evolution was no longer observed. The crude reaction mixture was poured into brine (20 mL) whilst being vigorously stirred. The resulting suspension was filtered through celite, and the filter cake was washed with EtOAc (2×10 mL). The filtrate was washed with brine (30 mL), and the brine layer was back extracted with EtOAc (3×20 mL). The combined organic extracts were dried over MgSO₄, filtered, concentrated in vacuo and purified via the Biotage SP4 (silica-packed SNAP column 180 g; 20-70% EtOAc/hexanes) to give the title product (S4) as a white solid (4.89 g, 73%). A sample of S4 suitable for X-ray crystallographic analysis was prepared by recrystallization from DCM.

Analysis of the product found: mp 112-114° C.; IR (KBr) $v_{max}$: 3433 (NH), 3201, 2963, 1514, 1031; ¹H NMR (500 MHz, CDCl₃) δ 7.65 (s, 1H, CH), 7.47-7.36 (m, 2H, 2×Ar H), 7.26-7.19 (m, 2H, 2×ArH), 4.53-4.49 (m, 1H, CH), 3.37 (d, J=9.4 Hz, 1H, NH), 2.59-2.44 (m, 2H, CH₂), 2.34-2.23 (m, 1H, CH), 1.95 (m, 1H, CH), 1.84 (m, 2H, CH, CH), 1.26 (s, 9H, 3×CH₃); ¹³C NMR (101 MHz, CDCl₃) δ 157.7 (C), 155.2 (C), 141.5 (C), 139.4 (CH), 130.1 (d, J=7.8 Hz, CH), 128.7 (CH), 124.9 (d, J=4.0 Hz, CH), 119.2 (C), 116.8 (d, J=19.9 Hz, CH), 56.3 (C), 50.8 (CH), 33.3 (CH₂), 22.9 (3×CH₃), 21.6 (CH₂), 20.3 (CH₂); m/z (ES⁺) 357.84 ([M+Na]⁺, 100%); HRMS (ES⁺) Calcd for C₁₇H₂₃N₃OSF [M+H]⁺: 358.1365, found 358.1366.

S5: 1-(2-methylphenyl)-4,5,6,7-tetrahydro-1H-indazol-4-one

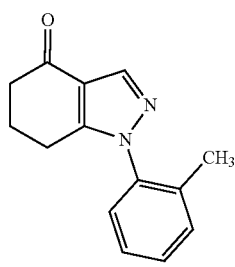 [SMILES: Cc1ccccc1-n1ncc2c1CCCC2=O]

The title compound was prepared using the method described in S2 to give a solid 1.11 g (70%). ¹H NMR (400 MHz, Chloroform-d) δ 8.07 (s, 1H), 7.45-7.29 (m, 3H), 7.29-7.25 (solvent), 7.24 (dd, J=7.8, 1.4 Hz, 1H), 2.64 (t, J=6.2 Hz, 2H), 2.58-2.50 (m, 2H), 2.21-2.11 (m, 2H), 2.11 (s, 3H); m/z (ES⁺) 227 [M+H]⁺.

S6: 1-(2-methylphenyl)-4,5,6,7-tetrahydro-1H-indazol-4-amine

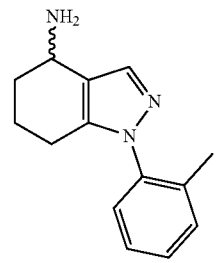 [SMILES: Cc1ccccc1-n1ncc2c1CCCC2N]

The compound was prepared by the method described in S2 to yield the crude product as a solid (46.8 mg, 100%). m/z (ES⁺) 228 [M+H]⁺.

S7: (S)-2-methyl-N-[(4R)-1-(2-methylphenyl)-4,5,6,7-tetrahydro-1H-indazol-4-yl]propane-2-sulfinamide

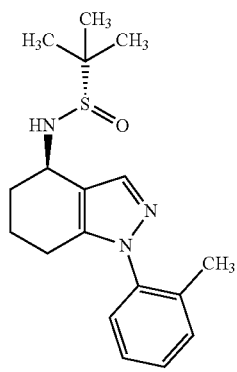 [SMILES: Cc1ccccc1-n1ncc2c1CCC[C@H]2N[S@@](=O)C(C)(C)C]

The title compound was prepared according to the method in S4 to give a solid (1.6 g, 70%).

1H NMR (400 MHz, DMSO-d6) δ 7.51 (s, 1H), 7.45-7.36 (m, 2H), 7.36-7.24 (m, 1H), 7.21 (m, 1H), 5.40 (d, J=8.4 Hz, 1H), 4.40-4.30 (m, 1H), 2.41-2.20 (m, 2H), 2.07-1.88 (m, 5H), 1.83-1.63 (m, 2H), 1.16 (s, 9H); m/z (ES⁺) 332 [M+H]⁺.

S8: (4R)-1-(2-methylphenyl)-4,5,6,7-tetrahydro-1H-indazol-4-amine

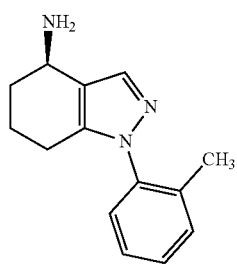 [SMILES: Cc1ccccc1-n1ncc2c1CCC[C@H]2N]

Concentrated hydrochloric acid (4 mL) was added dropwise to a solution of (S)-2-methyl-N-[(4R)-1-(2-methylphenyl)-4,5,6,7-tetrahydro-1H-indazol-4-yl]propane-2-sulfinamide (S7) (1.11 g, 3.32 mmol) in methanol (40 mL). The mixture was stirred at RT for 2 h. Saturated aqueous NaHCO₃ was added to pH 7 followed by water. The mixture was extracted with dichloromethane. The organic layer was washed with saturated aqueous NaHCO₃ and brine. The organic layer was concentrated in vacuo to afford the title compound (0.52 g, 68%) which was used without further purification. m/z (ES⁺) 228 [M+H]⁺.

S9: 1-phenyl-4,5,6,7-tetrahydro-1H-indazol-4-one

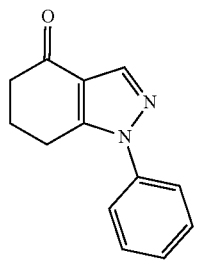 [SMILES: O=C1CCCc2c1cnn2-c1ccccc1]

The compound was purchased from a commercial source (Enamine).

S10: 1-phenyl-4,5,6,7-tetrahydroindazol-4-amine hydrochloride

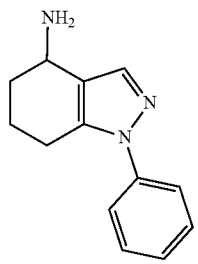 [SMILES: NC1CCCc2c1cnn2-c1ccccc1]

The title compound was synthesized using the method described in S6. The hydrochloric salt was obtained by treatment with HCl in EtOH and EtOAc and evaporation. Yield 141 mg (54%). ¹H NMR (400 MHz, DMSO-d₆) δ ppm 8.48 (br. s., 3H), 7.90 (s, 1H), 7.61-7.48 (m, 4H), 7.45-7.33 (m, 1H), 4.47-4.29 (m, 1H), 2.77 (t, J=5.69 Hz, 2H), 2.16-1.88 (m, 2H), 1.86-1.67 (m, 2H); m/z (ES⁺) 214 [M+H]⁺.

S11: 1-(2,3-Dimethylphenyl)-4,5,6,7-tetrahydro-1H-indazol-4-one

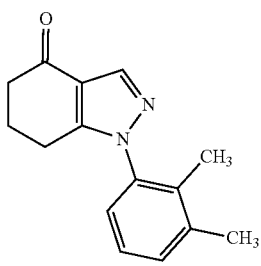 [SMILES: Cc1cccc(-n2ncc3c2CCCC3=O)c1C]

The title compound was prepared using the method described in S2 to give 0.425 g (88.4%). ¹H NMR (CDCl₃): 8.07 (s, 1H), 7.29 (d, J=7.6 Hz, 1H), 7.21 (t, J=7.6 Hz, 1H), 7.09 (d, J=7.6 Hz, 1H), 2.62 (t, J=6.0 Hz, 2H), 2.52-2.55 (m, 2H), 2.35 (s, 3H), 2.13-2.18 (m, 2H), 1.94 (s, 3H); m/z (ES⁺) 241 [M+H]⁺.

S12: 1-(2,3-dimethylphenyl)-4,5,6,7-tetrahydro-1H-indazol-4-amine

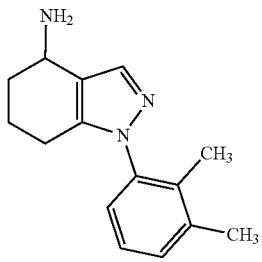 [SMILES: Cc1cccc(-n2ncc3c2CCCC3N)c1C]

The title compound was synthesized using the method described in S6 to give 0.585 g of crude product that was used without further purification. m/z (ES⁺) 242 [M+H]⁺.

S13 ethyl 3-(4-oxo-4,5,6,7-tetrahydro-1H-indazol-1-yl)benzoate

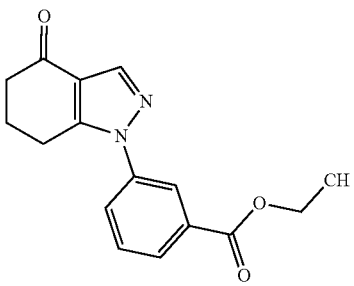 [SMILES: CCOC(=O)c1cccc(-n2ncc3c2CCCC3=O)c1]

2-Dimethylaminomethylenecyclohexane-1,3-dione (0.3344 g, 2.0 mmol) and 3-hydrazinylbenzoic acid (0.3043 g, 2.0 mmol) were dissolved in methanol (12.0 mL). Water and NaOH (aq) (1.0 mL, 2.0M) were added. This reaction mixture was heated at 90° C. for 2 h and then concentrated under vacuum. To the residue acetic acid (12.0 mL) and water (6.0 mL) were added and heated at 110° C. for 1.5 hr. The solution was concentrated under vacuum. Ethyl acetate (20 mL) was added to the residue and the mixture was washed with brine (20 mL), dried over Na₂SO₄ and concentrated. To the residue ethanol (10 mL) and concentrated sulfuric acid (0.15 mL) were added. The mixture was refluxed overnight. The solvents were removed under vacuum and ethyl acetate (20 mL) was added to the residue. The mixture was washed with NaHCO₃ and brine and was dried over Na₂SO₄. The residue was purified by silica gel chromatography (petroleum ether/ethyl acetate, 2:1) to give 0.240 g (42.2%). ¹H NMR (CDCl₃): 8.15-8.17 (m, 1H), 8.09-8.11 (m, 2H), 7.73-7.76 (m, 1H), 7.58-7.62 (m, 1H), 4.41 (q, J=7.1 Hz, 2H), 3.01 (t, J=6.2 Hz, 2H), 2.55-2.58 (m, 2H), 2.16-2.22 (m, 2H), 1.41 (t, J=7.1 Hz, 3H); m/z (ES⁺) 285 [M+H]⁺.

S14: ethyl 3-(4-amino-4,5,6,7-tetrahydro-1H-indazol-1-yl)benzoate

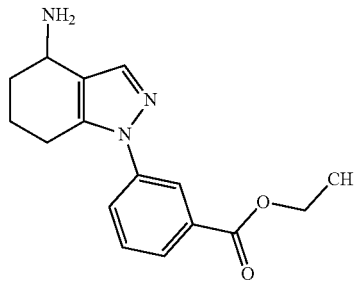 [SMILES: CCOC(=O)c1cccc(-n2ncc3c2CCCC3N)c1]

The title compound was synthesized using the method described in S6 to give by using ethyl 3-(4,5,6,7-tetrahydro-4-oxo-1H-indazol-1-yl)benzoate as a starting material, with the modification that the heating time was 7 h at 70° C., to give 0.342 g of crude product. m/z (ES⁺) 286 [M+H]⁺.

S15: (R)-1-(2-fluorophenyl)-4,5,6,7-tetrahydro-1H-indazol-4-amine hydrochloride

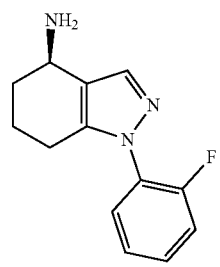 [SMILES: N[C@@H]1CCCc2c1cnn2-c1ccccc1F]

Conc HCl (5 mL) was added to a solution of (R)—N—((R)-1-(2-fluorophenyl)-4,5,6,7-tetrahydro-1H-indazol-4-yl)-2-methylpropane-2-sulfinamide (S4) (1.68 g, 5.0 mmol) in methanol (50 mL). The mixture was stirred at RT for 30 minutes. The solvents were evaporated and the residue was crystallized from a mixture of hot 2-propanol (10-20 mL) and ethyl acetate (ca 150 mL). The solid was collected by filtration and was washed with a small amount of ethyl acetate to give the title compound as a solid (1.0 g, 75%). H NMR (400 MHz, METHANOL-d4) δ ppm 7.85 (s, 1H), 7.61-7.53 (m, 1H), 7.49 (td, J=7.74, 1.42 Hz, 1H), 7.42-7.33 (m, 2H), 4.54 (t, J=5.53 Hz, 1H), 2.68-2.50 (m, 2H), 2.28-2.15 (m, 1H), 2.11-1.99 (m, 1H), 1.98-1.85 (m, 2H);

S16: 1-(3-methylphenyl)-1,5,6,7-tetrahydro-4H-indazol-4-one

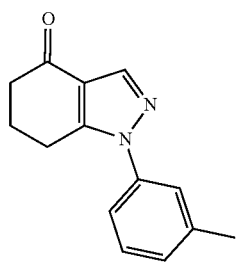 [SMILES: Cc1cccc(-n2ncc3c2CCCC3=O)c1]

The title compound was prepared using the method described in S2 to give 0.405 g (89.4%). ¹H NMR (CDCl₃): 8.08 (s, 1H), 7.42-7.36 (m, 2H), 7.30-7.24 (m, 2H), 2.98 (t, J=6.2 Hz, 2H), 2.55 (m, 2H), 2.45 (s, 3H), 2.18 (m, 2H); m/z (ES⁺) 227 [M+H]⁺.

S17: 1-(3-methylphenyl)-4,5,6,7-tetrahydro-H-indazol-4-amine

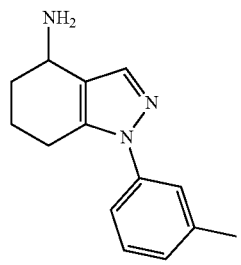 [SMILES: Cc1cccc(-n2ncc3c2CCCC3N)c1]

The title compound was synthesized using the method described in S6. The crude product (0.504 g) was used without further purification. m/z (ES⁺) 228 [M+H]⁺.

S18: 2-bromo-4,5-dimethyl-pyridine

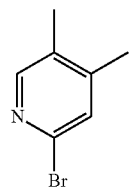

The title compound was synthesized from 3,4-dimethylpyridine as described in T. Kaminski et al. Eur. J. Org. Chem. 2003 (19) 3855-3860 (2003).

S19: methyl 4,5-dimethylpyridine-2-carboxylate

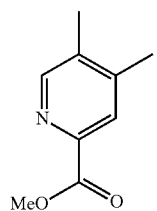

Bis(acetato)bis[o-(di-o-tolylphosphino)benzyl]dipalladium(II) (44 mg, 0.047 mmol), tri-tert-butylphosphonium tetrafluoroborate (55 mg, 0.19 mmol), molybdenumhexacarbonyl (248 mg, 0.940 mmol) and 2-bromo-4,5-dimethylpyridine (S18) (175 mg, 0.940 mmol) were dissolved in methanol (4 ml). 1,8-Diazabicyclo[5.4.0]undec-7-ene (0.42 ml, 2.8 mmol) was added and the vial was capped and heated in a microwave reactor at 120° C. for 15 min. After cooling, the reaction mixture was filtered through a silica plug and the product was eluted with EtOAc. The solution was concentrated and the title compound was purified by column chromatography on silica eluting with gradients of EtOAc in pentane (5-50%) to give the title compound 40 mg (26%).

¹H NMR (400 MHz, CDCl₃) δ 8.45 (s, 1H), 7.92 (s, 1H), 4.00 (s, 3H), 2.34 (s, 3H), 2.32 (s, 3H). m/z (ES⁺) 166 [M+H]⁺.

S20: lithium 4,5-dimethylpyridine-2-carboxylate

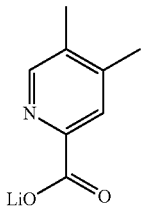

Methyl 4,5-dimethylpyridine-2-carboxylate (S19) (39 mg, 0.24 mmol) was dissolved in THF (0.6 ml) and methanol (0.6 ml). Lithium hydroxide (2M, 0.24 ml) was added and the reaction mixture was stirred at r.t. overnight. The solvent was removed at reduced pressure and the residue co-evaporated with toluene to dryness. The mixture was used without further purification. m/z (ES⁺) 152 [M+H]⁺.

S21: 1-(2-fluoro-5-methylphenyl)-4,5,6,7-tetrahydro-1H-indazol-4-one

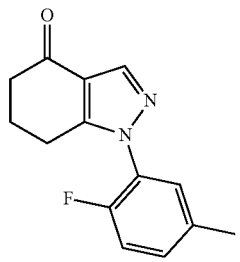 [SMILES: Cc1ccc(F)c(-n2ncc3c2CCCC3=O)c1]

The title compound was prepared using the method described in S2 to give 1.07 g (73%). ¹H NMR (400 MHz, CDCl₃) δ 8.09 (s, 1H), 7.33 (dd, J=7.0, 1.9 Hz, 1H), 7.27-7.21 (m, 1H), 7.14 (dd, J=10.1, 8.5 Hz, 1H), 2.80 (td, J=6.3, 1.4 Hz, 2H), 2.55 (dd, J=7.3, 5.6 Hz, 2H), 2.39 (s, 3H), 2.21-2.10 (m, 2H). m/z (ES⁺) 245 [M+H]+

S22: (S)—N-[(4R)-1-(2-fluoro-5-methylphenyl)-4,5,6,7-tetrahydro-1H-indazol-4-yl]-2-methylpropane-2-sulfinamide

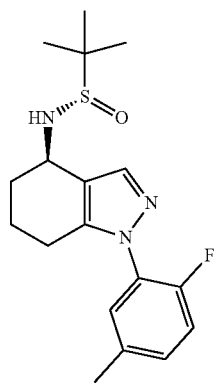 [SMILES: Cc1ccc(F)c(-n2ncc3c2CCC[C@H]3N[S@@](=O)C(C)(C)C)c1]

The title compound was prepared using the method described in S3 to give the title compound 0.94 g (61.4%). ¹H NMR (400 MHz, CDCl₃) δ 7.64 (s, 1H), 7.29-7.23 (m, 1H, overlapping with the solvent signal), 7.21-7.14 (m, 1H), 7.13-7.05 (m, 1H), 4.55-4.45 (m, 1H), 3.34 (d, J=9.5 Hz, 1H), 2.62-2.42 (m, 2H), 2.36 (s, 3H), 2.33-2.24 (m, 1H), 2.00-1.73 (m, 3H), 1.26 (s, 9H). m/z (ES⁺) 350 [M+H]⁺

S23: (4R)-1-(2-fluoro-5-methylphenyl)-4,5,6,7-tetrahydro-1H-indazol-4-amine

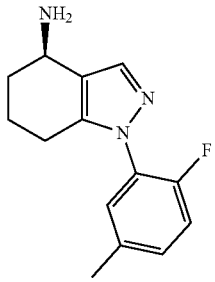 [SMILES: Cc1ccc(F)c(-n2ncc3c2CCC[C@H]3N)c1]

(S)—N-[(4R)-1-(2-Fluoro-5-methylphenyl)-4,5,6,7-tetrahydro-1H-indazol-4-yl]-2-methylpropane-2-sulfinamide (S22) (300 mg, 0.858 mmol) was dissolved in methanol (2 ml) and concentrated hydrochloric acid (196 μl, 2.42 mmol) was added. The mixture was stirred at r.t. for 30 min. NaHCO₃ (sat, aq.) and dichloromethane were added. The phases were separated and the organic phase was washed with NaHCO₃ (sat, aq.) and brine, dried over MgSO₄ and concentrated to give the title compound (171 mg) 81%. ¹H NMR (400 MHz, CDCl₃) δ 7.69 (s, 1H), 7.28-7.22 (m, 1H), 7.18-7.12 (m, 1H), 7.07 (dd, J=10.1, 8.5 Hz, 1H), 4.07-3.98 (m, 1H), 2.60-2.42 (m, 2H), 2.35 (s, 3H), 2.10-1.88 (m, 2H), 1.80-1.68 (m, 1H), 1.56-1.46 (m, 1H). m/z (ES⁺) 246 [M+H]⁺.

S24: ethyl 3-(4-oxo-4,5,6,7-tetrahydro-1H-indazol-1-yl)benzoate

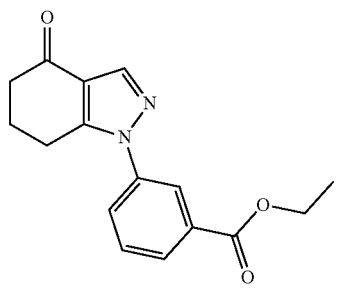 [SMILES: CCOC(=O)c1cccc(-n2ncc3c2CCCC3=O)c1]

The title compound was prepared using the method described in S2 to give a solid. Yield 1.15 g (45%); m/z (ES⁺) 285 [M+H]⁺.

S25: propan-2-yl-3-[(4R)-4-{[(R)-2-methylpropane-2-sulfinyl]amino}-4,5,6,7-tetrahydro-1H-indazol-1-yl]benzoate

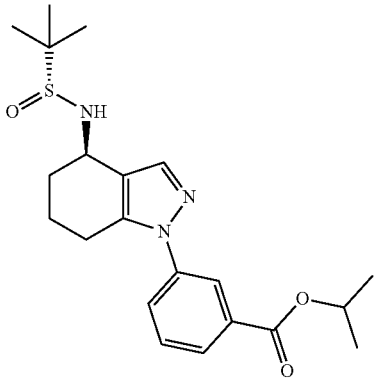 [SMILES: CC(C)OC(=O)c1cccc(-n2ncc3c2CCC[C@H]3N[S@](=O)C(C)(C)C)c1]

The title compound was prepared using the method described in S4, using Ti(O-i-Pr)$_4$ instead of Ti(OEt)$_4$, to give a solid 0.70 g (53%). $^1$H NMR (400 MHz, DMSO-d$_6$) δ ppm 8.07 (t, J=1.82 Hz, 1H), 7.90-7.95 (m, 1H), 7.83 (ddd, J=8.06, 2.29, 1.03 Hz, 1H), 7.66 (t, J=7.90 Hz, 1H), 7.61 (s, 1H), 5.46 (d, J=8.69 Hz, 1H), 5.17 (spt, J=6.27 Hz, 1H), 4.29-4.39 (m, 1H), 2.65-2.84 (m, 2H), 1.91-2.08 (m, 2H), 1.65-1.86 (m, 2H), 1.34 (d, J=6.16 Hz, 6H), 1.16 (s, 9H). m/z (ES$^+$) 404 [M+H]$^+$

S26: propan-2-yl 3-[(4R)-4-amino-4,5,6,7-tetrahydro-1H-indazol-1-yl]benzoate

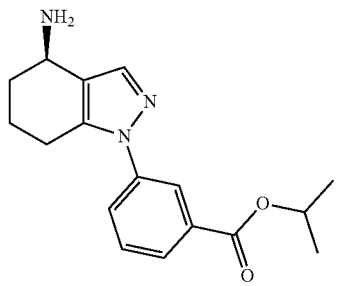 [SMILES: CC(C)OC(=O)c1cccc(-n2ncc3c2CCC[C@H]3N)c1]

The title compound was prepared using the method described in S8 to yield the crude product as a solid 0.47 g, (100%). m/z (ES$^+$) 300 [M+H]$^+$.

BIOLOGICAL EXAMPLES

Biological Example 1: Inhibition of Human Dihydroorotate Dehydrogenase (DHODH)

Inhibition of human dihydroorotate dehydrogenase (DHODH) by example compounds as described herein was determined using one of two assays as described below.

Assay A

DHODH enzyme assays were performed with 6 nM recombinant human DHODH (purified essentially as described by Walse et. al., *Biochemistry*, 47, 8929-8936 (2008)). The reaction mixture consisted of 1 mM DL-dihydroorotic acid (#D7003, Sigma-Aldrich), 100 μM 3,4-dimethoxy-5-methyl-p-benzoquinone (#D9150, Sigma-Aldrich), and 100 μM 2,6-dichlorophenolindophenol sodium salt (DCIP) (#D1878, Sigma-Aldrich) in enzyme buffer (50 mM Tris-HCl pH 8.0, 0.1% Triton X-100, 150 mM KCl). A stock solution of 20 mM DCIP was prepared in enzyme buffer and filtered through Whatman paper just before use. Loss in absorbance by chromogen DCIP was measured at 595 nm at RT every 3 min for an hour.

Assay B

Example compounds as described herein were dispensed with an acoustic liquid handler, Echo 550 (Labcyte) to a maximum volume of 50 nl per well in a 384 well plate. DHODH enzyme assays were performed with 4 nM recombinant human DHODH (purified essentially as described by Walse et. al., *Biochemistry*, 47, 8929-8936 (2008)). The reaction mixture consisted of 2 mM DL-dihydroorotic acid (#D7003, Sigma-Aldrich), 100 μM 3,4-dimethoxy-5-methyl-p-benzoquinone (#D9150, Sigma-Aldrich), and 200 μM 2,6-dichlorophenolindophenol sodium salt (DCIP) (#D1878, Sigma-Aldrich) in enzyme buffer (50 mM Tris-HCl pH 8.0, 0.1% Triton X-100, 150 mM KCl) in a final volume of 50 μl per well. A stock solution of 80 mM DCIP was prepared in DMSO just before use. Loss in absorbance by chromogen DCIP was measured at 595 nm at RT every 2 min for an hour with a plate reader (Envision, Perkin Elmer).

Using the assays described in Biological Example 1, the following IC$_{50}$ values were obtained.

| Example | IC50 (μM) DHODH |
|---------|-----------------|
| 1 | 2.172[a] |
| 2 | 6.360[a] |
| 3 | 0.166[a] |
| 4 | 1.11[a] |
| 5 | 0.29[a] |
| 6 | 5.83[a] |
| 7 | >10[a] |
| 8 | 0.032[a] |
| 9 | >10[a] |
| 10 | 2.44[a] |
| 11 | 8.20[a] |
| 13 | 0.011[b] |
| 14 | 0.009[b] |
| 15 | 0.735[b] |
| 16 | 0.009[b] |
| 17 | 0.124[b] |
| 18 | 0.459[b] |
| 19 | 0.136[b] |
| 20 | 0.355[b] |
| 21 | 0.881[b] |
| 22 | 0.032[b] |
| 23 | 2390[b] |
| 24 | 0.066[b] |
| 25 | 0.014[b] |
| 26 | 0.096[b] |
| 27 | 0.112[b] |
| 28 | 0.018[b] |
| 29 | 0.005[b] |
| 30 | 0.009[b] |
| 31 | 0.004[b] |
| 32 | 0.030[b] |
| 33 | 0.088[b] |
| 34 | 0.003[b] |
| 35 | 2.67[b] |
| 36 | 0.031[b] |
| 37 | 0.039[b] |
| 38 | 2.08[b] |
| 39 | 0.025[b] |
| 40 | 2.0[b] |
| 41 | 0.078[b] |
| 42 | 0.047[b] |
| 43 | 0.441[b] |
| 44 | 0.033[b] |

-continued

| Example | IC50 (µM) DHODH |
|---|---|
| 45 | >3[b] |
| 46 | 0.006[b] |
| 47 | 0.050[b] |
| 48 | 0.008[b] |
| 49 | 0.017[b] |
| 50 | 0.119[b] |
| 51 | 0.032[b] |
| 52 | 0.011[b] |
| 53 | 0.220[b] |

[a]results obtained using Assay A as described above
[b]results obtained using Assay B as described above Biological Example 2: Activation of p53 in Cells by the Compound of Example 8 in the Presence and Absence of Excess Uridine DHODH inhibition increases the expression of p53 tumor suppressor target genes. Using a p53 reporter cell based assay it is possible to assess the ability of compounds to be active in cells. If these compounds activate p53 by virtue of their ability to inhibit DHODH, it is expected that activation of p53 by these compounds is prevented by treating cells with uridine (which allows pyrimidine synthesis to proceed even in the absence of DHODH).

Method: ARN8 melanoma cells retaining wild type p53 and containing a construct expressing beta-galactosydase under the control of a p53-dependent promoter are seeded in 96 well plates (5,000 cells per well). Next day, cells are treated with increasing concentrations of Example 8 in the absence or presence of excess uridine (100 micromolar). 16 hours after incubation, cells are lysed in lysis buffer (Promega #E397A) and chlorophenol red-β-D-galactopyranoside (CPRG, a substrate for beta-galactosydase) is added. Plates are incubated at room temperature and color change of the CPRG substrate is measured at 595 nM.

FIG. 1 shows results obtained with different concentrations of Example 8 on the activation of the transcription factor function of p53 in the absence and presence of excess uridine.

Biological Example 3: Reduction of Cancer Cell Growth and/or Viability by Example 8 in the Presence and Absence of Excess Uridine Using the Sulforhodamine B Assay ARN8 melanoma cells are seeded at a density of 500 cells per well of a 96 well plate. Following 24 hours of incubation, cells are treated with increasing concentrations of the compound of Example 8 in the absence or presence of excess uridine (100 micromolar). Cells are incubated for 72 hours after which the growth medium is removed from the cells and replaced by 150 mL of 1× sterile PBS and 50 µL of 40% trichloroacetic acid in dH2O. Samples are incubated at 4° C. for 1 h to fix the cells. The plate is then washed with 3 changes of water with all liquid allowed to drain from the plate. 50 mL of 0.1% sulforhodamine B in 1% acetic acid in $H_2O$ is added to each well and incubated for 30 minutes. Excess dye is washed out with three changes of 1% acetic acid in H2O with all liquid allowed to drain from the plate. The remaining dye is solubilized in 100 microliters of 10 mM un-buffered basic Tris per well and absorbance read at 570 nm.

Figure 2:
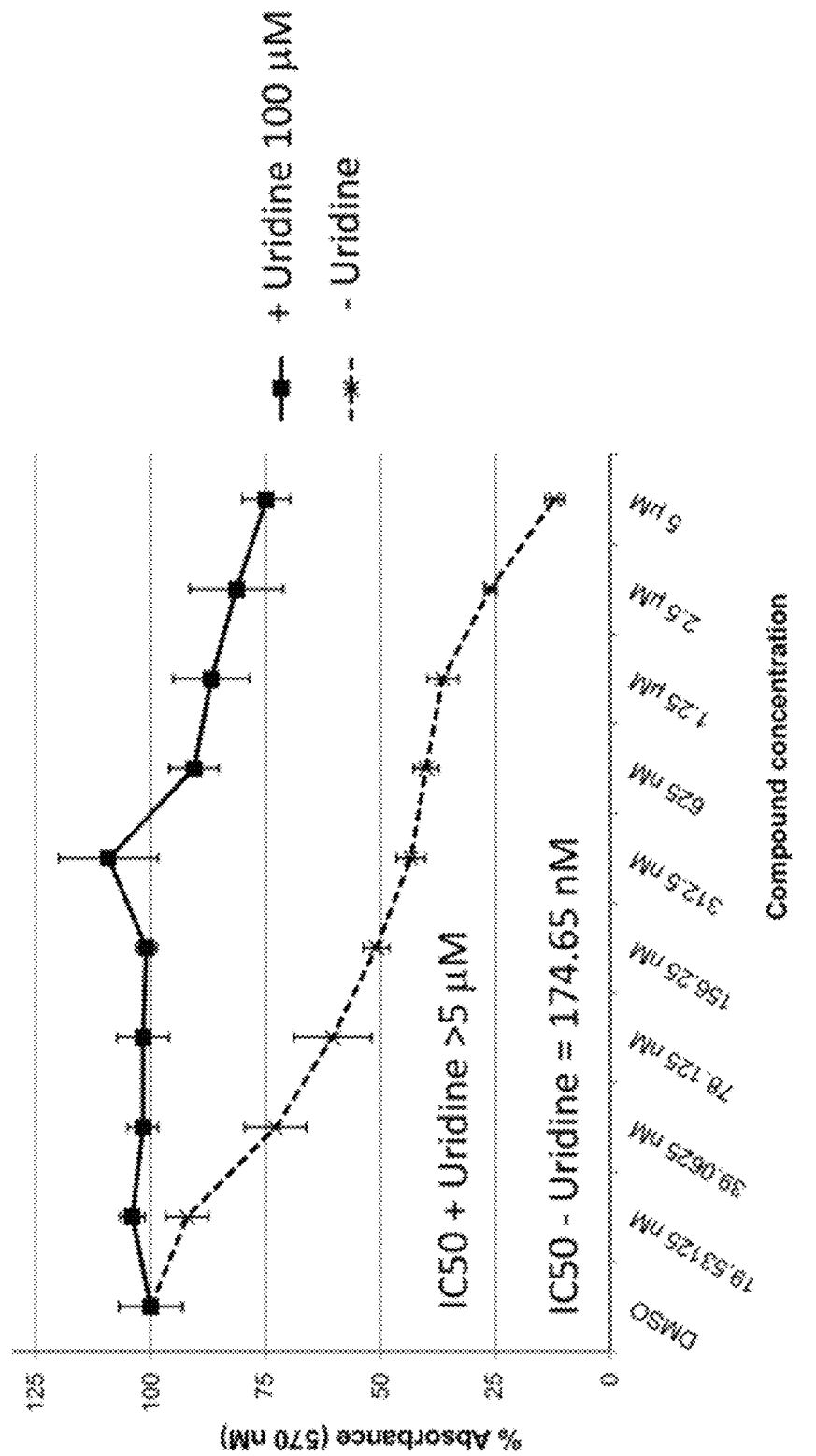
FIG. 2 shows results obtained from Biological Example 3, which shows that the compound of Example 8 reduces ARN8 melanoma cell growth and/or viability, and that this effect is largely prevented by the addition of excess uridine.

FIG. 2 shows that the compound of Example 8 reduces ARN8 melanoma cell growth and/or viability, and that this effect is largely prevented by the addition of excess uridine.

The following table shows results obtained for the example compounds described herein in the absence of excess uridine.

| Example | ARN8 melanoma cell viability (% at 2 µM) |
|---|---|
| 1 | 53 |
| 2 | 100 |
| 3 | 30 |
| 4 | 52 |
| 5 | 22 |
| 6 | 105 |
| 7 | 28 |
| 8 | 48 |
| 9 | 8 |
| 10 | 92 |
| 11 | 93 |

Biological Example 4: The Compound of Example 1 Increases p53 Synthesis

Figure 3:
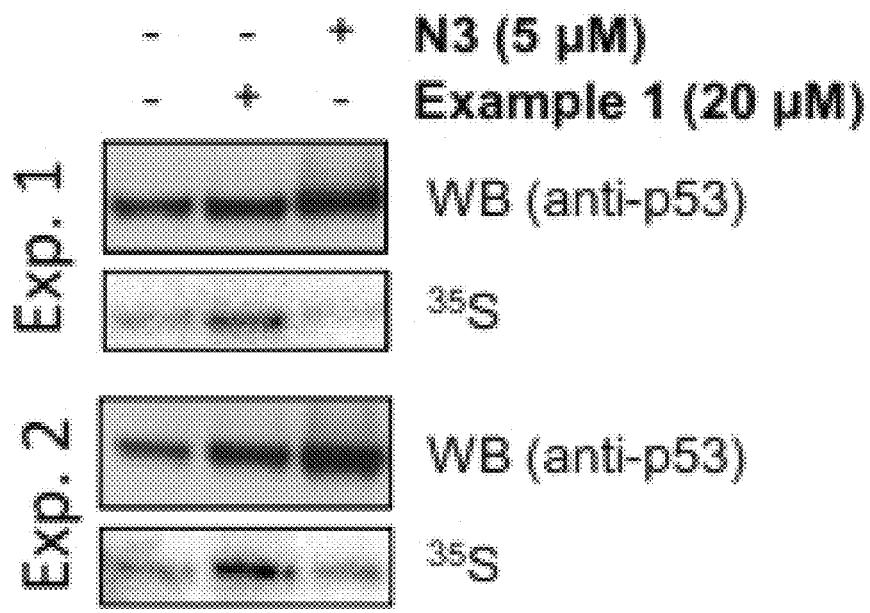
FIG. 3 shows results obtained from Biological Example 4, which shows that the compound of Example 1 increases p53 synthesis.

ARN8 melanoma cells were treated with the compound of Example 1, nutlin-3 or vehicle (DMSO) for 5 h and pulse labeled with 35S-Met for 30 minutes. p53 was immunoprecipitated and p53 protein levels were determined. Incorporation of 35S-Met in the p53 immunoprecipitate was determined by autoradiography. This experiment was performed in duplicate (Exp. 1 and Exp. 2). The results obtained are shown in FIG. 3.

Figure 4:
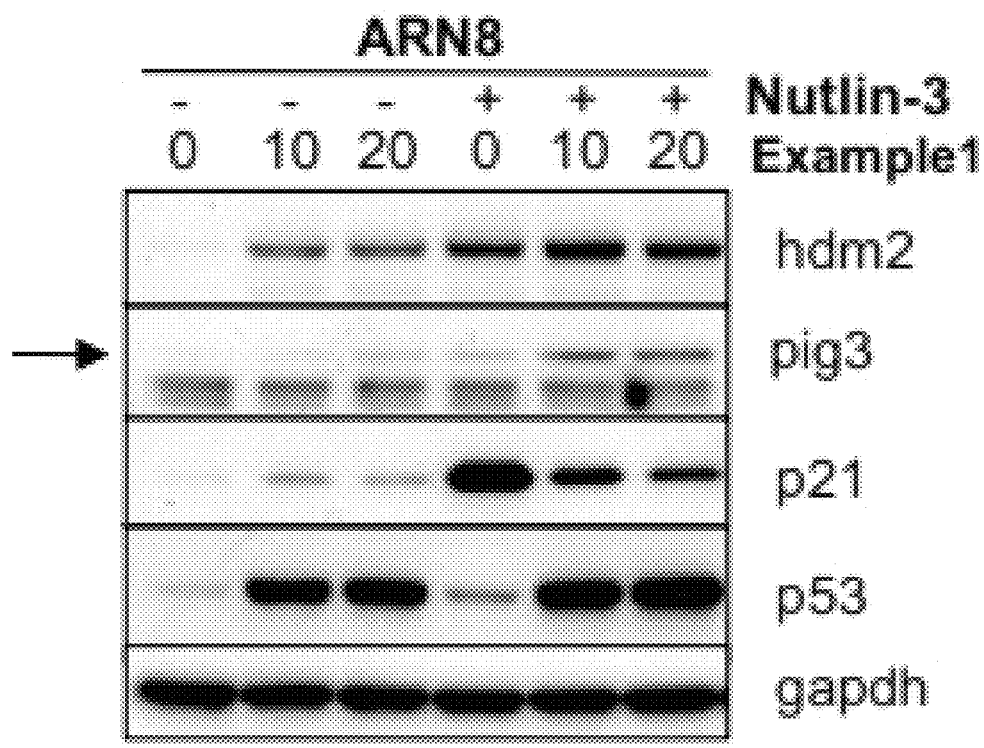
FIG. 4 shows results obtained from FIG. 5, which shows that loss of nutlin-3 induced p21 expression by the compound of Example 1 is also associated with an increase in apoptosis.

Biological Example 5: Loss of Nutlin-3 Induced p21 Expression by Example 1 is Also Associated with an Increase in Apoptosis ARN8 melanoma cells were treated with the compound of Example 1 for 1 h and then 2 µM nutlin-3 added for an additional 18 h. The results are shown in FIG. 4. Levels of p53 and downstream targets hdm2, pig3 (band indicated by arrow) and p21 were determined. Levels of gapdh were used to monitor protein loading. Pig3 is a known pro-apoptotic protein. Loss of nutlin-3 induced p21 expression by the compound of Example 1 is also associated with an increase in apoptosis.

Figure 5:
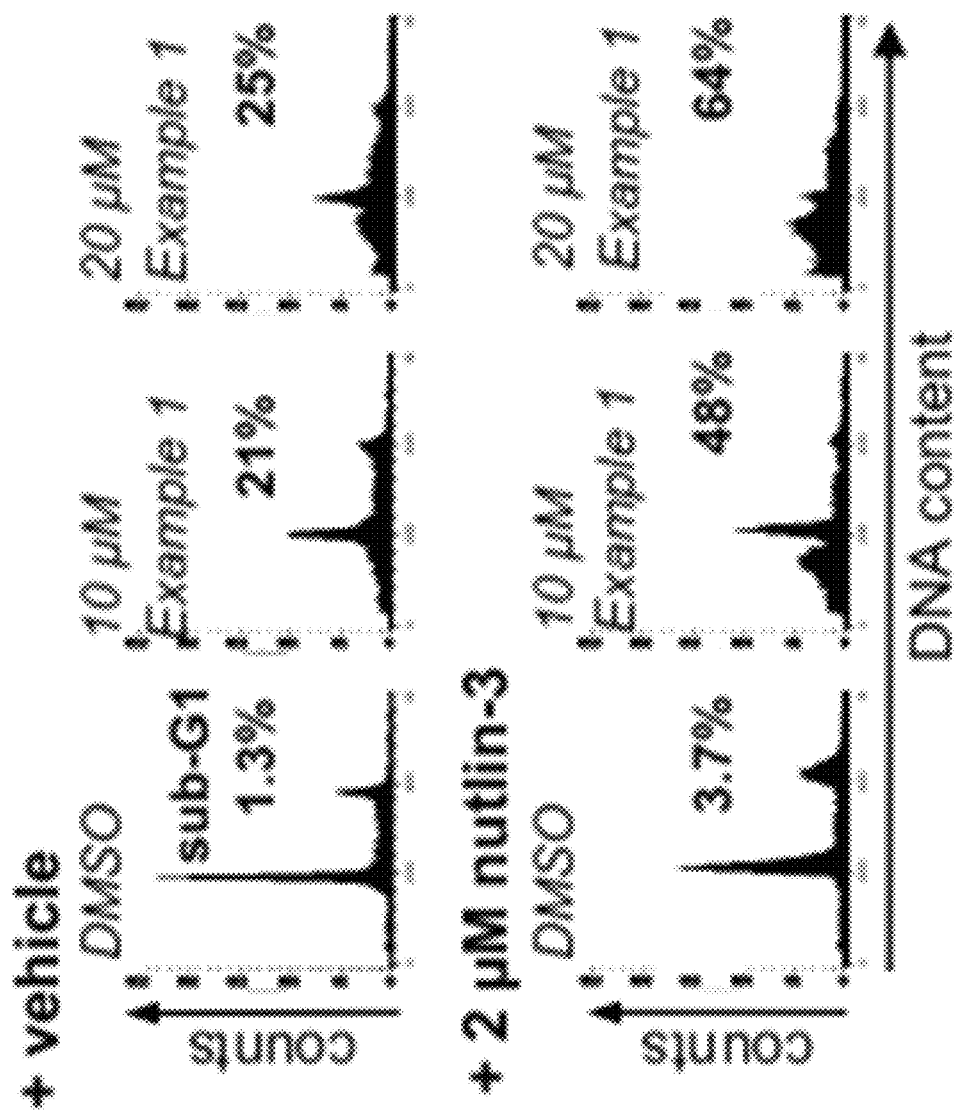
FIG. 5 shows results obtained from Biological Example 6, which determines the effect of the compound of Example 1 and nutlin-3 on cell death.
Figure 6:
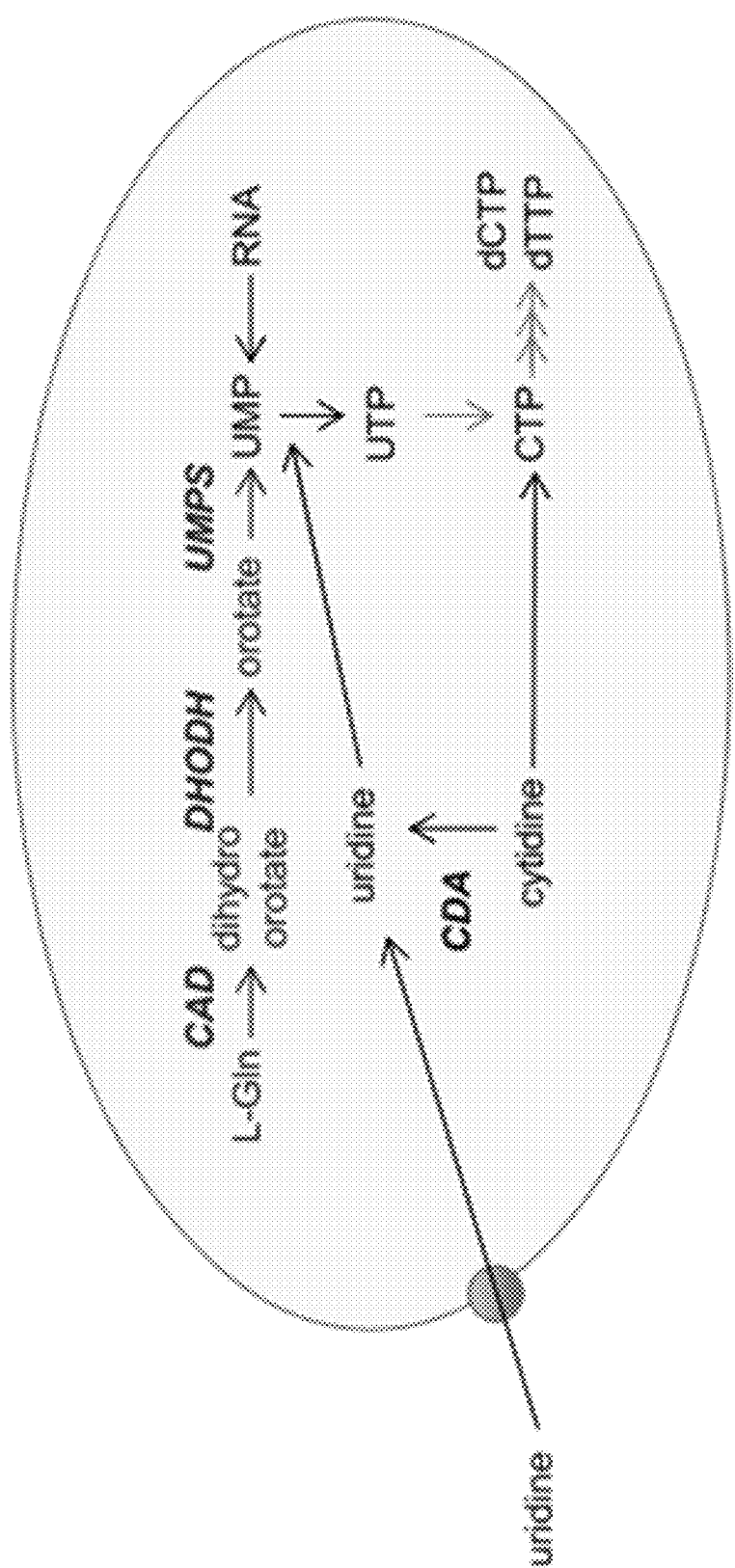
FIG. 6 shows a simplified description of the pyrimidine nucleotide de novo synthesis (blue) and salvage (black) pathways.

Biological Example 6: Effect of the Compound of Example 1 and Nutlin-3 on Cell Death ARN8 melanoma cells were treated with the compound of Example 1 for 1 hour and then nutlin-3 added for a further 48 hours (49 hours MJ05 treatment in total). DNA content was determined by flow cytometry following propidium iodide staining and the percentage of cells with a sub-G1 DNA content (i.e. dead cells) was determined using CellQuestPro software. DMSO is the solvent vehicle for nutlin-3 and the compound of Example 1. The results obtained are shown in FIG. 5.

Biological Example 7: Nilotinib Blocks Uridine Uptake in ARN8 Cells

ARN8 cells were incubated with increasing concentrations of nilotinib and tritiated uridine. The amount of tritium label in cells was determined by scintillation counting. 200

Figure 7:
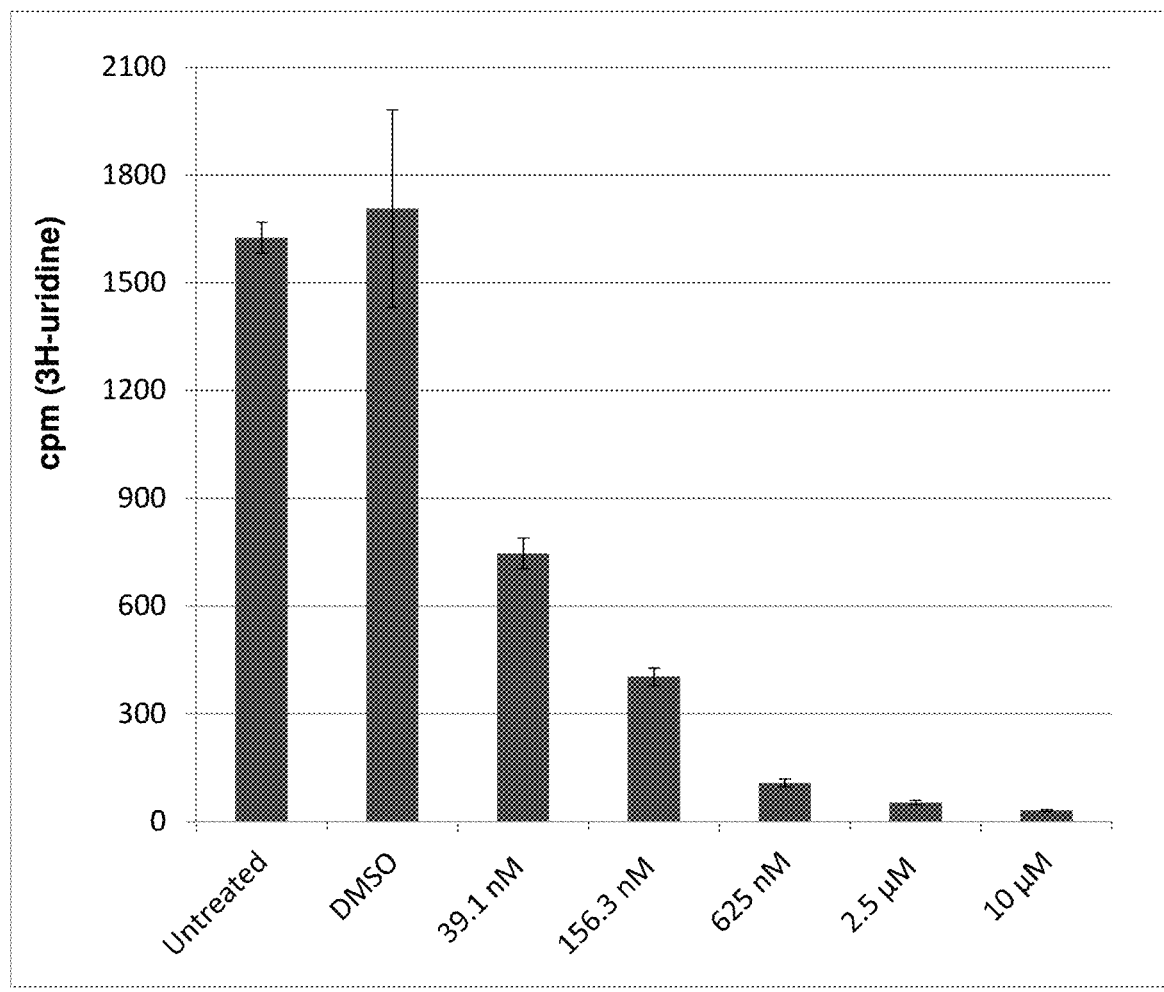
FIG. 7 shows results obtained from Biological Example 7, which shows that nilotinib blocks uridine uptake in ARN8 cells.

000 ARN8 cells/well were seeded on 6-well plates. 24 h post-seeding, the cells were rinsed twice with transport buffer, pH 7.4 (20 mM Tris/HCl, 130 mM NaCl, 3 mM K$_2$HPO$_4$, 1 mM MgCl2, 5 mM Glucose) and then incubated for 15 min at 37° C. with compounds (or vehicle) diluted in transport buffer. 5,6-3H-Uridine (PerkinElmer, #NET367001MC) was added to a final concentration of 4 µCi/mL for 60 sec, and then removed with 5 quick washes with 1 mM ice-cold unlabeled uridine (Sigma, #U3003). Samples (in triplicate) were harvested in 10% SDS (Sigma) and transferred to a flexible 24-well microplate (Perkin Elmer, #1450-402). Optiphase Supermix scintillation buffer (PerkinElmer, #1200-439) was added and the counts per minute measured for 3 min. The results obtained are shown in FIG. 7.

Figure 8:
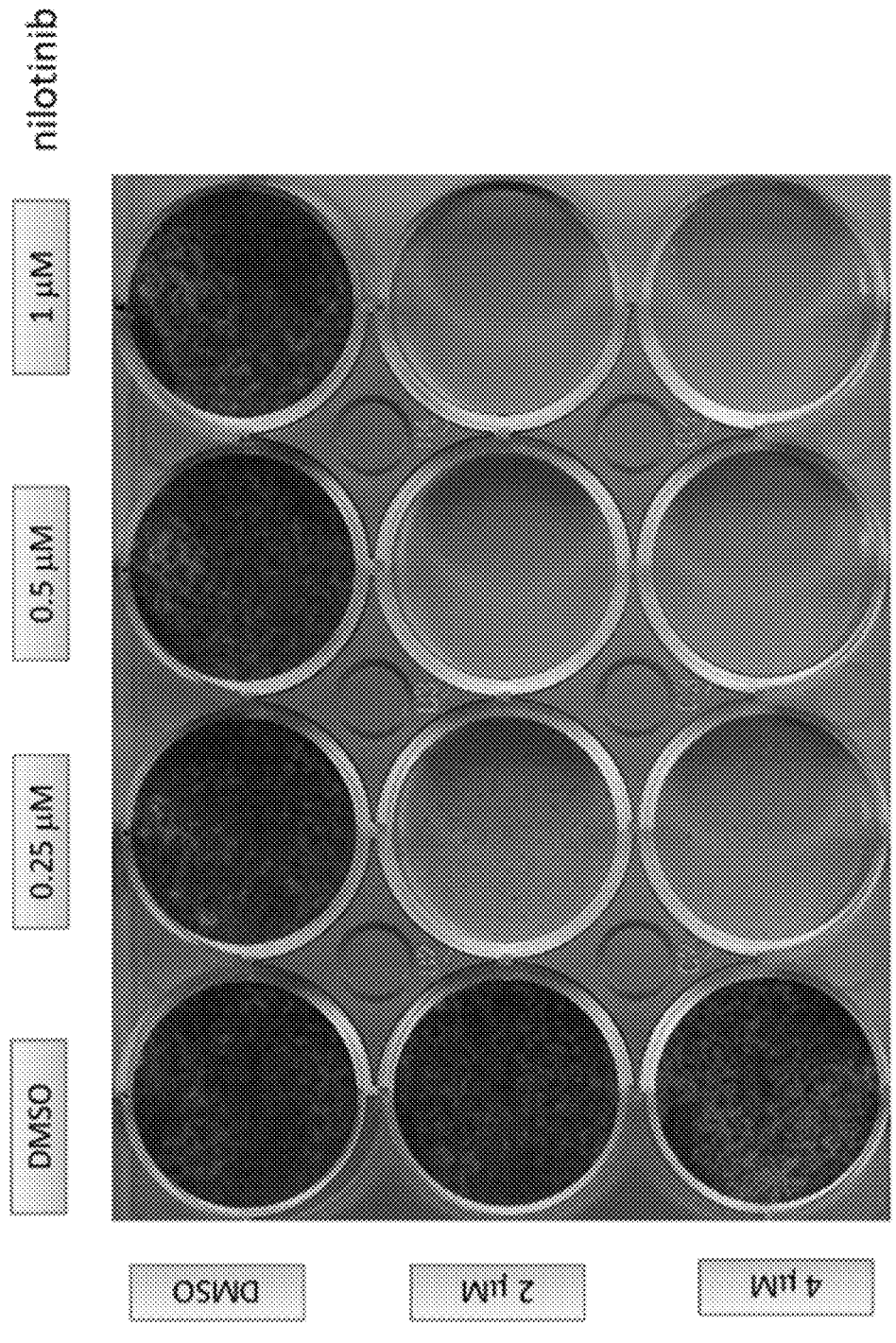
FIG. 8 shows results obtained from Biological Example 8, which shows the effect of the combination of the compound of Example 8 and nilotinib on ARN8 cell growth.

Biological Example 8: Effect of the Combination of the Compound of Example 8 and Nilotinib on ARN8 Cell Growth ARN8 melanoma cells were seeded on to 12 well plates and treated with the indicated concentrations of the compound of Example 8 and nilotinib alone or in combination for 72 hours. At this time point the medium was replaced with fresh drug free medium and cultures were allowed to regrow for 72 hours. At the end of the experiment, cells were fixed in metanol:acetone 50:50 and stained with Giemsa. DMSO is the compound solvent vehicle control. The results obtained are shown in FIG. 8.

Figure 9:
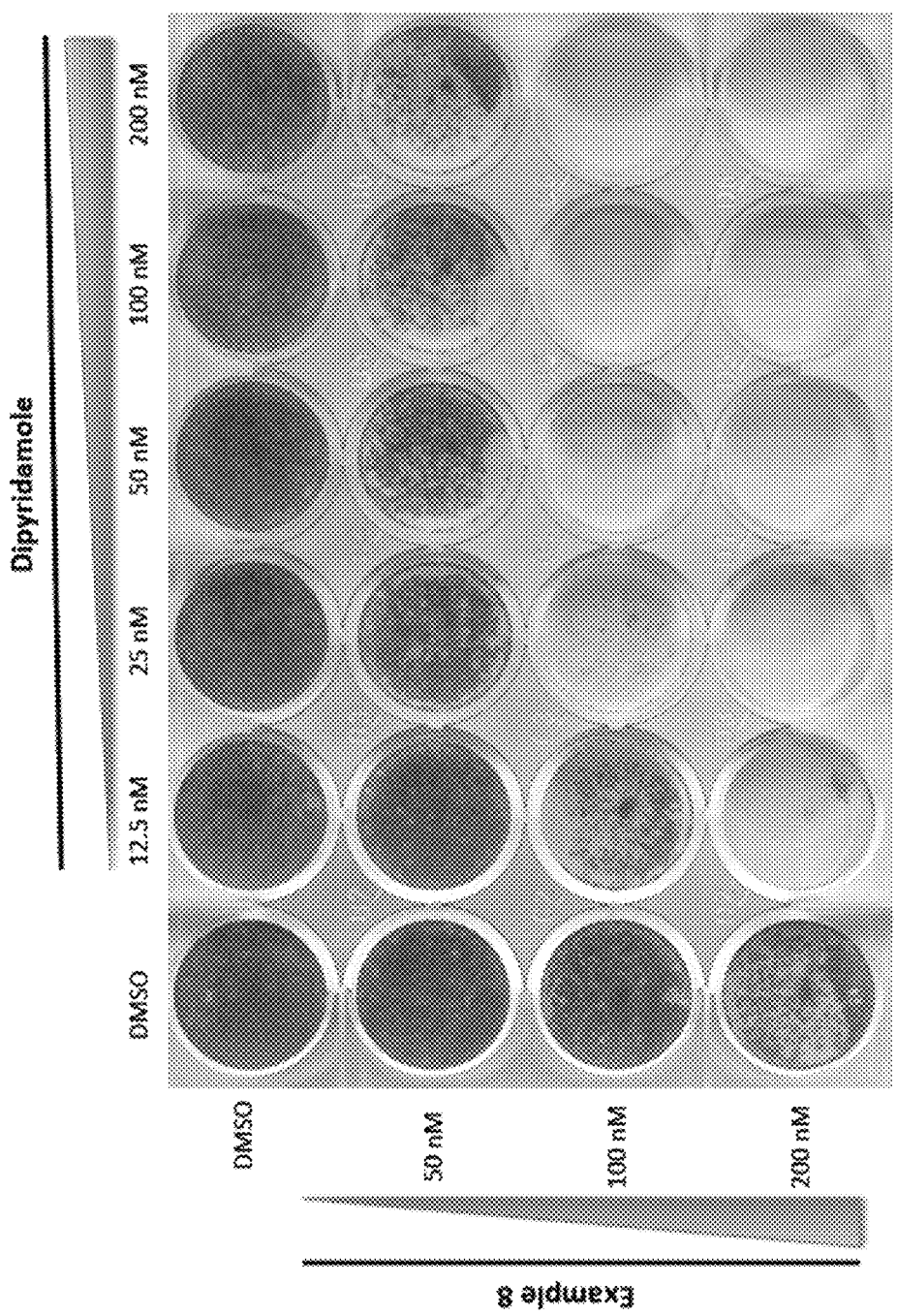
FIG. 9 shows results obtained from Biological Example 9, which shows the effect of the combination of the compound of Example 8 and dipyridamole on ARN8 cell growth.

Biological Example 9: Effect of the Combination of the Compound of Example 8 and Nilotinib on ARN8 Cell Growth ARN8 melanoma cells were seeded on to 24 well plates and treated with the indicated concentrations of the compound of Example 8 and dipyridamole alone or in combination for 72 hours. At this time point the medium was replaced with fresh drug free medium and cultures were allowed to regrow for 72 hours. At the end of the experiment, cells were fixed in metanol:acetone 50:50 and stained with Giemsa. DMSO is the compound solvent vehicle control. The results obtained are shown in FIG. 9.

Figure 10:
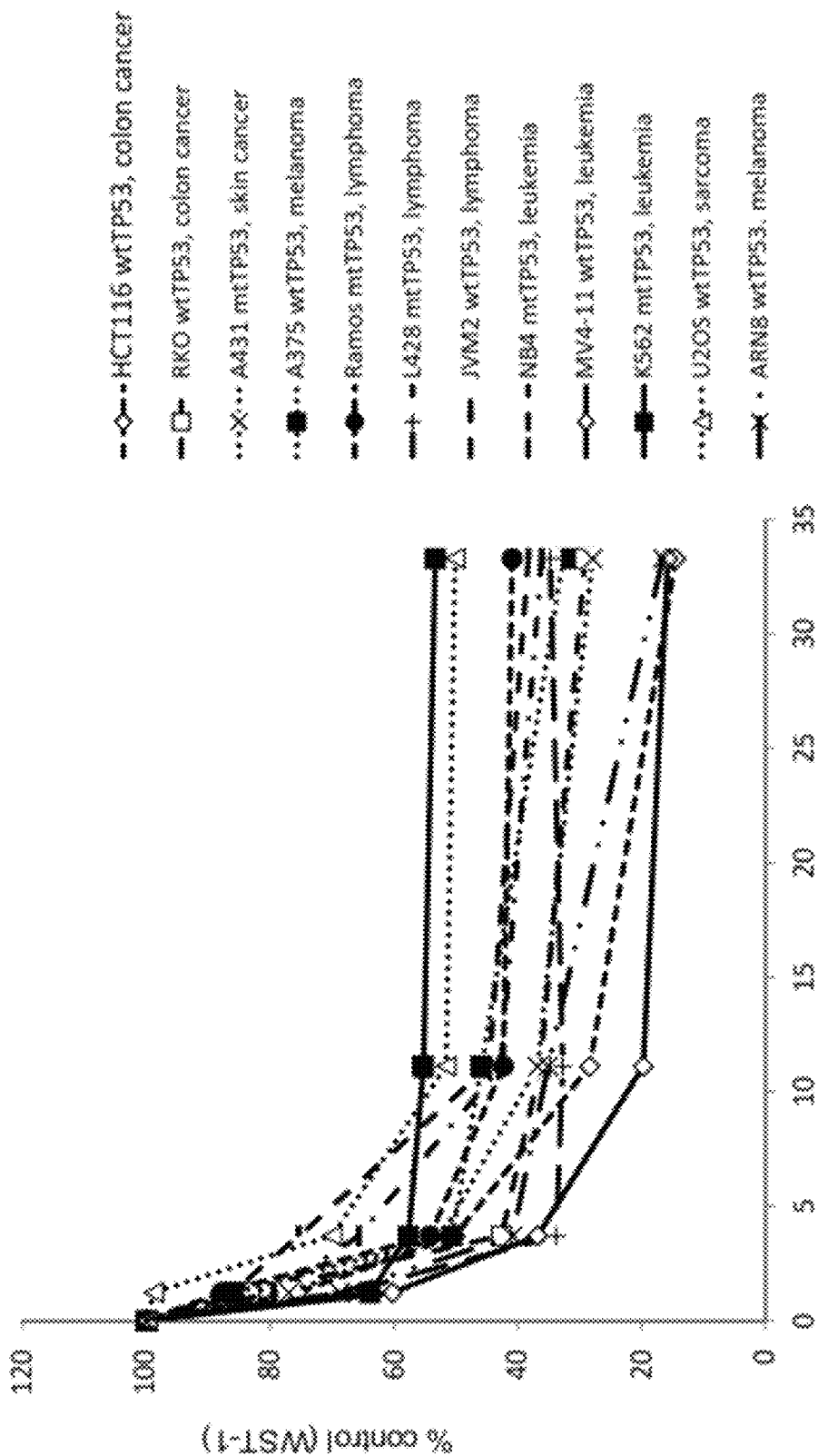
FIG. 10 shows results obtained from Biological Example 10, which show the effect of the compound of Example 1 on the viability and/or growth of a variety of cancer cell lines.

Biological Example 10: Effect of the Compound of Example 1 on the Viability and/or Growth of a Variety of Cancer Cell Lines WST-1 assay (Roche) was used to measure the number of metabolically active cells following 72 hours of exposure to the compound of Example 1 and the percentage relative to the vehicle (DMSO) control calculated. Adherent cell lines were cultured overnight prior to the addition of the compound of Example 1, whereas non-adherent cell lines were treated immediately after seeding. TP53 status in each cell line is indicated. All cells were grown in 10% FBS. p53 wild type or mutant status (wtTP53 or mtTP53) and tumor cell line origin are indicated. The results obtained are shown below and in FIG. 10.

| Example 1 conc. (µM) | 33.30 | 11.11 | 3.70 | 1.23 | 0.00 |
|---|---|---|---|---|---|
| HCT116 wtTP53, colon cancer | 14.51 | 28.40 | 50.13 | 75.69 | 100.00 |
| RKO wtTP53, colon cancer | 29.16 | 36.36 | 42.62 | 83.37 | 100.00 |
| HT29 mtTP53, colon cancer | 12.11 | 25.66 | 23.19 | 70.23 | 100.00 |
| A431 mtTP53, skin cancer | 27.93 | 36.84 | 52.31 | 76.99 | 100.00 |

-continued

| Example 1 conc. (µM) | 33.30 | 11.11 | 3.70 | 1.23 | 0.00 |
|---|---|---|---|---|---|
| A375 wtTP53, melanoma | 32.67 | 45.86 | 50.62 | 85.95 | 100.00 |
| Ramos mtTP53, lymphoma | 40.94 | 42.35 | 54.16 | 87.94 | 100.00 |
| L428 mtTP53, lymphoma | 34.80 | 32.76 | 33.84 | 67.78 | 100.00 |
| JVM2 wtTP53, lymphoma | 38.31 | 44.68 | 75.36 | 86.30 | 100.00 |
| NB4 mtTP53, leukemia | 36.19 | 42.77 | 65.73 | 79.47 | 100.00 |
| MV4-11 wtTP53, leukemia | 15.79 | 19.73 | 36.85 | 60.26 | 100.00 |
| K562 mtTP53, leukemia | 53.35 | 55.28 | 57.69 | 63.91 | 100.00 |
| U2OS wtTP53, sarcoma | 50.16 | 51.63 | 70.03 | 98.88 | 100.00 |
| ARN8s wtTP53, melanoma | 16.60 | 35.13 | 40.86 | 68.69 | 100.00 |

Biological Example 11: Effect of the Compound of Example 16 Alone or in Combination with Nilotinib on the Viability of GFP Expressing Semliki Forest Virus 80,000 HNDF cells per well were seeded on 12-well plates (1.5 mL medium per well). Medium was DMEM (HyClone) supplemented with 10% FBS and 100 U/mL Penicillin/Streptomycin. Next day, cells were infected with SFV virus expressing GFB at a MOI of 10 in the presence of the indicated compound concentrations and combinations thereof. Plates were incubated at 37° C. in a humidified atmosphere containing 5% (v/v) CO$_2$.

Figure 11:
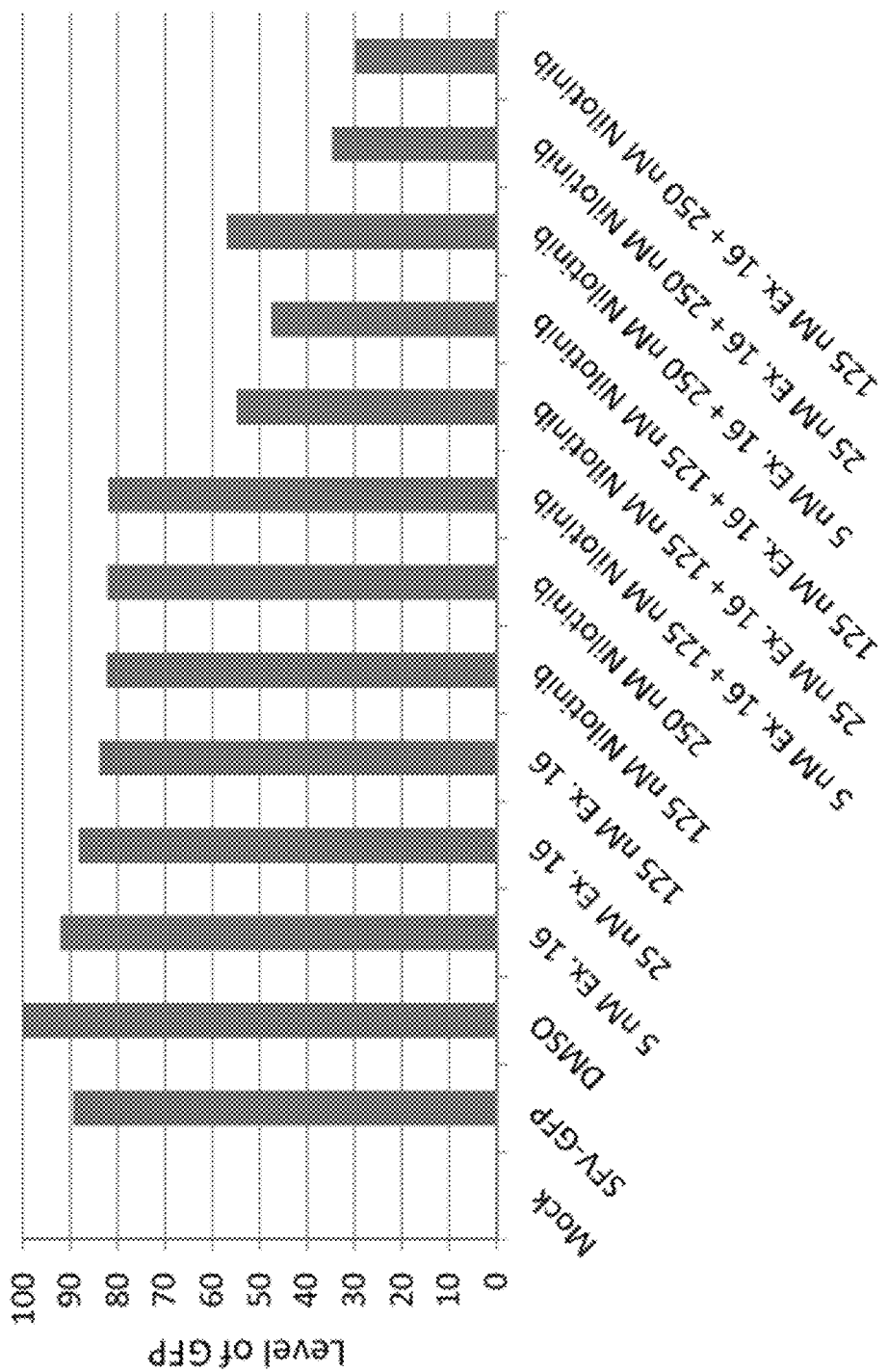
FIG. 11 shows results obtained from Biological Example 11, which show the effect of the compound of Example 16 on the viability of green fluorescence protein (GFP)-labeled Semliki Forest Virus (SFV) in human normal dermal fibroblasts.

24 hpi cells were unlabeled and GF labelled cells were analysed and counted by cell sorting. The results obtained are shown in FIG. 11.

Abbreviations

Abbreviations as used herein will be known to those skilled in the art. In particular, the following abbreviations may be used herein.
aq aqueous
DBU 1,8-diazabicyclo[5.4.0]undec-7-ene
DCM dichloromethane
DIPEA N,N-diisopropylethylamine
DMF dimethylformamide
DMSO dimethyl sulphoxide
EDC 1-ethyl-3-(3-dimethylaminopropyl)carbodiimide
HATU 1-[bis(dimethylamino)methylene]-1H-1,2,3-triazolo[4,5-b]pyridinium 3-oxid hexafluorophosphate
HBTU N,N,N',N'-tetramethyl-O-(1H-benzotriazol-1-yl)uronium hexafluorophosphate
HOBt hydroxybenzotriazole
HPLC high performance liquid chromatography
HRMS high resolution mass spectrometry
NMR nuclear magnetic resonance
r.t. room temperature
TBTU O-(benzotriazol-1-yl)-N,N,N',N'-tetramethyluronium tetrafluoroborate
TFA trifluoroacetic acid
THF tetrahydrofuran

The invention claimed is:
1. A method of treating cancer and/or treating a viral infection comprising administering to a patient in need thereof a therapeutically effective amount of a compound of formula I, or a pharmaceutically acceptable salt thereof, wherein the cancer is selected from the group consisting of: soft tissue cancers, lung cancers, gastrointestinal cancers, genitourinary tract cancers, liver cancers, bone cancers, cancers of the head and/or nervous system, gynecological cancers, haematologic cancers, skin cancers, and neuroblastomas; wherein formula I is:

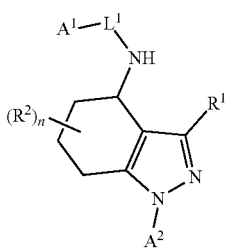

(I)

and wherein:
$A^1$ represents aryl optionally substituted by one or more groups independently selected from $G^1$ or heteroaryl optionally substituted by one or more groups independently selected from $G^2$;
$A^2$ represents aryl optionally substituted by one or more groups independently selected from $G^3$ or heteroaryl optionally substituted by one or more groups independently selected from $G^4$;
$L^1$ represents —C(O)—, —C(O)N($R^3$)—, —C(O)O—, —S(O)$_3$— or —S(O)$_k$N($R^4$)—;
$R^1$ represents H or $C_{1-3}$ alkyl optionally substituted by one or more halo;
$R^2$ represents F;
$R^3$ and $R^4$ each independently represents H or $C_{1-3}$ alkyl optionally substituted by one or more halo;
each $G^1$ independently represents halo, $R^{a1}$, —CN, -$A^{a1}$-C($Q^{a1}$)$R^{b1}$, -$A^{b1}$-C($Q^{b1}$)N($R^{c1}$)$R^{d1}$, -$A^{c1}$-C($Q^{c1}$)O$R^{e1}$, -$A^{d1}$-S(O)$_p$$R^{f1}$, -$A^{e1}$-S(O)$_q$N($R^{g1}$)$R^{h1}$, -$A^{f1}$S(O)$_r$O$R^{i1}$, —N$_3$, —N($R^{j1}$)$R^{k1}$, —N(H)CN, —NO$_2$, —ONO$_2$, —O$R^{l1}$ or —S$R^{m1}$;
each $Q^{a1}$ to $Q^{c1}$ independently represents =O, =S, =N$R^{n1}$ or =N(O$R^{o1}$);
each $A^{a1}$ to $A^{f1}$ independently represents a single bond, —N($R^{p1}$)— or —O—;
each $G^2$ independently represents halo, $R^{a2}$, —CN, -$A^{a2}$-C($Q^{a2}$)$R^{b2}$-$A^{b2}$-(Q^{b2})N($R^{e2}$)$R^{d2}$, -$A^{c2}$-C($Q^{c2}$)O$R^{e2}$, -$A^{d2}$-S(O)$_p$$R^{f2}$, -$A^{e2}$-S(O)$_q$N($R^{g2}$)$R^{h2}$, -$A^{f2}$-S(O)$_r$O$R^{i2}$, —N$_3$, —N($R^{j2}$)$R^{k2}$, —N(H)CN, —NO$_2$, —ONO$_2$, —O$R^{l2}$ or —S$R^{m2}$;
each $Q^{a2}$ to $Q^{c2}$ independently represents =O, =S, =N$R^{n2}$ or =N(O$R^{o2}$);
each $A^{a2}$ to $A^{f2}$ independently represents a single bond, —N($R^{p2}$)— or —O—;
each $G^3$ independently represents halo, $R^{a3}$, —CN, -$A^{a3}$-C($Q^{a3}$)$R^{b3}$, -$A^{b3}$-C($Q^{b3}$)N($R^{c3}$)$R^{d3}$, -$A^{c3}$-C($Q^{c3}$)O$R^{e3}$, -$A^{d3}$-S(O)$_p$$R^{f3}$, -$A^{e3}$-S(O)$_q$N($R^{g3}$)$R^{h3}$, -$A^{f3}$-S(O)$_r$O$R^{i3}$, —N$_3$, —N($R^{j3}$)$R^{k3}$, —N(H)CN, —NO$_2$, —ONO$_2$, —O$R^{l3}$ or —S$R^{m3}$;
each $Q^{a3}$ to $Q^{c3}$ independently represents =O, =S, =N$R^{n3}$ or =N(O$R^{o3}$);
each $A^{a3}$ to $A^{f3}$ independently represents a single bond, —N($R^{p3}$)— or —O—;
each $G^4$ independently represents halo, $R^{a4}$, —CN, -$A^{a4}$-C($Q^{a4}$)$R^{b4}$, -$A^{b4}$-C($Q^{b4}$)N($R^{c4}$)$R^{d4}$, -$A^{c4}$-C($Q^{c4}$)O$R^{e4}$, -$A^{d4}$-S(O)$_p$$R^{f4}$, -$A^{e4}$-S(O)$_q$N($R^{g4}$)$R^{h4}$, -$A^{f4}$-S(O)$_r$O$R^{i4}$, —N$_3$, —N($R^{j4}$)$R^{k4}$, —N(H)CN, —NO$_2$, —ONO$_2$, —O$R^{l4}$ or —S$R^{m4}$;
each $Q^{a4}$ to $Q^{c4}$ independently represents =O, =S, =N$R^{n4}$ or =N(O$R^{o4}$);
each $A^{a4}$ to $A^{f4}$ independently represents a single bond, —N($R^{p4}$)— or —O—;
each $R^{a1}$ and $R^{f1}$ independently represents $C_{1-6}$ alkyl optionally substituted by one or more groups independently selected from $G^{5a}$, heterocycloalkyl optionally substituted by one or more groups independently selected from $G^{5b}$, aryl optionally substituted by one or more groups independently selected from $G^{5c}$, or heteroaryl optionally substituted by one or more groups independently selected from $G^{5d}$;
each $R^{p1}$ independently represents H or $C_{1-6}$ alkyl optionally substituted by one or more halo;
each $R^{b1}$, $R^{c1}$, $R^{d1}$, $R^{e1}$, $R^{g1}$, $R^{h1}$, $R^{i1}$, $R^{j1}$, $R^{k1}$, $R^{l1}$, $R^{m1}$, $R^{n1}$ and $R^{o1}$ independently represents H, $C_{1-6}$ alkyl optionally substituted by one or more groups independently selected from $G^{5a}$, heterocycloalkyl optionally substituted by one or more groups independently selected from $G^{5b}$, aryl optionally substituted by one or more groups independently selected from $G^{5c}$, or heteroaryl optionally substituted by one or more groups independently selected from $G^{5d}$; or
alternatively any of $R^{c1}$ and $R^{d1}$, $R^{g1}$ and $R^{h1}$ and/or $R^{j1}$ and $R^{k1}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl optionally substituted by one or more halo, and =O;
each $R^{a2}$ and $R^{f2}$ independently represents $C_{1-6}$ alkyl optionally substituted by one or more groups independently selected from $G^{6a}$, heterocycloalkyl optionally substituted by one or more groups independently selected from $G^{6b}$, aryl optionally substituted by one or more groups independently selected from $G^{6c}$, or heteroaryl optionally substituted by one or more groups independently selected from $G^{6d}$;
each $R^{p2}$ independently represents H or $C_{1-6}$ alkyl optionally substituted by one or more F;
each $R^{b2}$, $R^{c2}$, $R^{d2}$, $R^{e2}$, $R^{g2}$, $R^{h2}$, $R^{i2}$, $R^{j2}$, $R^{k2}$, $R^{l2}$, $R^{m2}$, $R^{n2}$ and $R^{o2}$ independently represents H, $C_{1-6}$ alkyl optionally substituted by one or more groups independently selected from $G^{6a}$, heterocycloalkyl optionally substituted by one or more groups independently selected from $G^{6b}$, aryl optionally substituted by one or more groups independently selected from $G^{6c}$, or heteroaryl optionally substituted by one or more groups independently selected from $G^{6d}$; or
alternatively any of $R^{c2}$ and $R^{d2}$, $R^{g2}$ and $R^{h2}$ and/or $R^{j2}$ and $R^{k2}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl optionally substituted by one or more halo, and =O;
each $R^{a3}$ and $R^{f3}$ independently represents $C_{1-6}$ alkyl optionally substituted by one or more groups independently selected from $G^{7a}$, heterocycloalkyl optionally substituted by one or more groups independently selected from $G^{7b}$, aryl optionally substituted by one or more groups independently selected from $G^{7c}$, or heteroaryl optionally substituted by one or more groups independently selected from $G^{7d}$;
each $R^{p3}$ independently represents H or $C_{1-6}$ alkyl optionally substituted by one or more F;
each $R^{b3}$, $T^{c3}$, $R^{d3}$, $R^{e3}$, $R^{g3}$, $R^{h3}$, $R^{i3}$, $R^{j3}$, $R^{k3}$, $R^{l3}$, $R^{m3}$, $R^{n3}$ and $R^{o3}$ independently represents H, $C_{1-6}$ alkyl optionally substituted by one or more groups independently selected from $G^{7a}$, heterocycloalkyl optionally substituted by one or more groups independently selected from $G^{7b}$, aryl optionally substituted by one or more groups independently selected from $G^{7c}$, or heteroaryl optionally substituted by one or more groups independently selected from $G^{7d}$; or alternatively any of $R^{c3}$ and $R^{d3}$, $R^{g3}$ and $R^{h3}$ and/or $R^{j3}$ and $R^{k3}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl optionally substituted by one or more halo, and =O;

each $R^{a4}$ and $R^{f4}$ independently represents $C_{1-6}$ alkyl optionally substituted by one or more groups independently selected from $G^{8a}$, or heterocycloalkyl optionally substituted by one or more groups independently selected from $G^{8b}$, aryl optionally substituted by one or more groups independently selected from $G^{8c}$, or heteroaryl optionally substituted by one or more groups independently selected from $G^{8d}$;

each $R^{p4}$ independently represents H or $C_{1-6}$ alkyl optionally substituted by one or more F;

each $R^{b4}$, $R^{c4}$, $R^{d4}$, $R^{e4}$, $R^{g4}$, $R^{h4}$, $R^{i4}$, $R^{j4}$, $R^{k4}$, $R^{l4}$, $R^{m4}$, $R^{n4}$ and $R^{o4}$ independently represents H, $C_{1-6}$alkyl optionally substituted by one or more groups independently selected from $G^{8a}$ or heterocycloalkyl optionally substituted by one or more groups independently selected from $G^{8b}$; or alternatively any of $R^{c4}$ and $R^{d4}$, $R^{g4}$ and $R^{h4}$ and/or $R^{j4}$ and $R^{k4}$ are linked together to form, together with the nitrogen atom to which they are attached, a 3- to 6-membered ring, which ring optionally contains one further heteroatom and which ring optionally is substituted by one or more groups independently selected from halo, $C_{1-3}$ alkyl optionally substituted by one or more halo, and =O;

each $G^{5a}$, $G^{5b}$, $G^{6a}$, $G^{6b}$, $G^{7a}$, $G^{7b}$, $G^{8a}$ and $G^{8b}$ independently represents halo, —CN, —N($R^{b5}$)$R^{c5}$, —OR$^{d5}$, —SR$^{e5}$ or =O;

each $G^{5c}$, $G^{5d}$, $G^{6c}$, $G^{6d}$, $G^{7c}$, $G^{7d}$, $G^{8c}$ and $G^{8d}$ independently represents halo, R$^{a5}$, —CN, —N($R^{b5}$)$R^{c5}$, —OR$^{d5}$, —SR$^{e5}$ or =O;

each $R^{a5}$ independently represents $C_{1-6}$ alkyl optionally substituted by one or more F;

each $R^{b5}$, $R^{c5}$, $R^{d5}$ and $R^{e5}$ independently represents H or $C_{1-6}$ alkyl optionally substituted by one or more F;

or $R^{b5}$ and $R^{c5}$ are linked together to form, along with the nitrogen atom to which they are attached, a 3- to 6-membered ring, which ring optionally contains one further heteroatom and which ring optionally is substituted by one or more groups independently selected from F, $C_{1-3}$ alkyl optionally substituted by one or more F, and =O;

each j independently represents 0, 1 or 2;

each k, p and q independently represents 1 or 2; and n represents 0 to 7.

2. The method of claim 1, wherein the compound is of formula Ib:

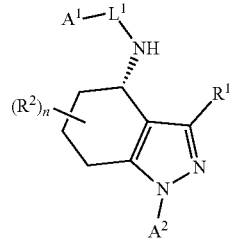

(Ib)

or a pharmaceutically acceptable salt thereof, and wherein $A^1$, $A^2$, $R^1$, $R^2$, $L^1$ and n are as defined in claim 1.

3. The method of claim 2, wherein the compound or a pharmaceutically acceptable salt thereof exists in the substantial absence of compounds of the alternative configuration.

4. The method of claim 1, wherein:
a) $A^1$ represents heteroaryl optionally substituted by one or more groups independently selected from $G^2$;
b) $A^2$ represents phenyl optionally substituted by one or more groups independently selected from $G^3$ or a 5- or 6-membered heteroaryl optionally substituted by one or more groups independently selected from $G^4$;
c) $L^1$ represents —S(O)$_2$— or —C(O)—;
d) $R^1$ represents H or $C_{1-3}$ alkyl substituted by one or more F;
e) n represents 0; or
f) $R^3$ and $R^4$ each independently represents H or $C_{1-3}$ alkyl substituted by one or more F.

5. The method of claim 1, wherein:
a) each $G^1$ independently represents halo, R$^{a1}$, —C(O)OR$^{e1}$, —OR$^{l1}$ or —SR$^{m1}$;
b) each $G^2$ independently represents halo, R$^{a2}$, —C(O)OR$^{e2}$, —OR$^{l2}$ or —SR$^{m2}$;
c) each $G^3$ independently represents halo, R$^{a3}$, —OR$^{l3}$ or —SR$^{m3}$; or
d) each $G^4$ independently represents halo, R$^{a4}$, —OR$^{l4}$ or —SR$^{m4}$.

6. The method of claim 1, wherein:
a) $A^1$ represents a mono- or bi-cyclic heteroaryl optionally substituted by one or two groups independently selected from:
i) halo, R$^{a2}$, —C(O)OR$^{e2}$, —OR$^{l2}$ and —SR$^{m2}$; or
ii) halo, $C_{1-3}$ alkyl optionally substituted by one or more fluoro, —C(O)OH, —C(O)OC$_{1-3}$ alkyl, —OH, —OC$_{1-3}$ alkyl, —SH and —SC$_{1-3}$ alkyl; or
b) the mono- or bi-cyclic heteroaryl representing $A^1$ is:
i) a 5- or 6-membered monocyclic or a 9-membered bicyclic heteroaryl; or
ii) selected from tetrahydro-2,1-benzisoxazolyl, benzoxazoyl, pyrazinyl, indazolyl, quinolinyl, 5H,6H,7H,8H-imidazo[1,5-a]pyridine-3-yl, imidazo[1,5-a]pyridin-3-yl, pyridinyl, thiozolyl, isoxazolyl and tetrahydro-1,2-benzisoxazolyl.

7. The method of claim 1, wherein $A^2$:
a) represents phenyl optionally substituted by one or more groups independently selected from halo, -A$^{a3}$-C(Q$^{a3}$)R$^{b3}$, -A$^{c3}$-C(Q$^{c3}$)OR$^{e3}$, R$^{a3}$ and —OR$^{l3}$;
b) phenyl optionally substituted by one or more groups independently selected from halo, —C(O)-morpholinyl, —C(O)OC$_{1-3}$ alkyl, and $C_{1-4}$ alkyl;
c) is unsubstituted in at least the 2-position; or
d) is phenyl substituted with one or two substitutions which are present at the 3-, 4-, 5- and/or 6-position(s).

8. The method of claim 2, wherein:
a) $A^1$ represents heteroaryl optionally substituted by one or more groups independently selected from $G^2$;
b) $A^2$ represents phenyl optionally substituted by one or more groups independently selected from $G^3$ or a 5- or 6-membered heteroaryl optionally substituted by one or more groups independently selected from $G^4$;
c) $L^1$ represents —S(O)$^2$— or —C(O)—;
d) $R^1$ represents H or $C_{1-3}$ alkyl substituted by one or more F;
e) n represents 0; or
f) $R^3$ and $R^4$ each independently represents H or $C_{1-3}$ alkyl substituted by one or more F.

9. The method of claim 2, wherein:
a) each $G^1$ independently represents halo, $R^{a1}$, —C(O)OR$^{e1}$, —OR$^{l1}$ or —SR$^{m1}$;
b) each $G^2$ independently represents halo, $R^{a2}$, —C(O)OR$^{e2}$, —OR$^{l2}$ or —SR$^{m2}$;
c) each $G^3$ independently represents halo, $R^{a3}$, —OR$^{l3}$ or —SR$^{m3}$; or
d) each $G^4$ independently represents halo, $R^{a4}$, —OR$^{l4}$ or —SR$^{m4}$.

10. The method of claim 2, wherein:
a) $A^1$ represents a mono- or bi-cyclic heteroaryl optionally substituted by one or two groups independently selected from:
i) halo, $R^{a2}$, —C(O)OR$^{e2}$, —OR$^{l2}$ and —SR$^{m2}$; or
ii) halo, $C_{1-3}$ alkyl optionally substituted by one or more fluoro, —C(O)OH, —C(O)OC$_{1-3}$ alkyl, —OH, —OC$_{1-3}$ alkyl, —SH and —SC$_{1-3}$ alkyl; or
b) the mono- or bi-cyclic heteroaryl representing $A^1$ is:
i) a 5- or 6-membered monocyclic or a 9-membered bicyclic heteroaryl; or
ii) selected from tetrahydro-2,1-benzisoxazolyl, benzoxazoyl, pyrazinyl, indazolyl, quinolinyl, 5H,6H,7H,8H-imidazo[1,5-a]pyridine-3-yl, imidazo[1,5-a]pyridin-3-yl, pyridinyl, thiozolyl, isoxazolyl and tetrahydro-1,2-benzisoxazolyl.

11. The method of claim 2, wherein $A^2$:
a) represents phenyl optionally substituted by one or more groups independently selected from halo, -A$^{a3}$-C(Q$^{a3}$)R$^{b3}$, -A$^{c3}$-C(Q$^{c3}$)OR$^{e3}$, R$^{a3}$ and —OR$^{l3}$;
b) phenyl optionally substituted by one or more groups independently selected from halo, —C(O)-morpholinyl, —C(O)OC$_{1-3}$ alkyl, and $C_{1-4}$ alkyl;
c) is unsubstituted in at least the 2-position; or
d) is phenyl substituted with one or two substitutions which are present at the 3-, 4-, 5- and/or 6-position(s).

12. The method of claim 1, wherein the cancer is selected from the group consisting of a skin cancer, a haematologic cancer and malignant melanoma.

* * * * *

UNITED STATES PATENT AND TRADEMARK OFFICE
CERTIFICATE OF CORRECTION

PATENT NO. : 11,795,157 B2
APPLICATION NO. : 17/144673
DATED : October 24, 2023
INVENTOR(S) : Sonia Lain et al.

It is certified that error appears in the above-identified patent and that said Letters Patent is hereby corrected as shown below:

In the Claims

At Column 81, Claim number 1, Line 24, replace "-S(O)$_3$-" with "-S(O)$_j$-".

At Column 81, Claim number 1, Line 36, replace "=NR$^{l1}$" with "=NR$^{n1}$".

At Column 81, Claim number 1, Line 40, replace "C(Q$^{a2}$)R$^{b2}$-A$^{b2}$-(Q$^{b2}$)N(R$^{e2}$)R$^{d2}$," with "C(Q$^{a2}$)R$^{b2}$, -A$^{b2}$-C(Q$^{b2}$)N(R$^{e2}$)R$^{d2}$,".

At Column 82, Claim number 1, Line 63, replace "T$^{c3}$" with "R$^{c3}$".

At Column 85, Claim number 8, Line 8, replace "S(O)$^2$" with "S(O)$_2$".

Signed and Sealed this
Thirtieth Day of January, 2024

Katherine Kelly Vidal
*Director of the United States Patent and Trademark Office*